(12) United States Patent
Nishikawa et al.

(10) Patent No.: US 7,839,508 B2
(45) Date of Patent: Nov. 23, 2010

(54) SURFACE PLASMON RESONANCE SENSOR AND SENSOR CHIP

(75) Inventors: Takeo Nishikawa, Kyotanabe (JP); Tomohiko Matsushita, Kyoto (JP); Hideyuki Yamashita, Daito (JP); Ryosuke Hasui, Nara (JP); Satoshi Fujita, Nara (JP); Yutaro Okuno, Kyoto (JP); Shigeru Aoyama, Kizugawa (JP)

(73) Assignee: OMRON Corporation, Kyoto-shi, Kyoto (JP)

( * ) Notice: Subject to any disclaimer, the term of this patent is extended or adjusted under 35 U.S.C. 154(b) by 317 days.

(21) Appl. No.: 12/042,910

(22) Filed: Mar. 5, 2008

(65) Prior Publication Data

US 2008/0218761 A1    Sep. 11, 2008

(30) Foreign Application Priority Data

Mar. 5, 2007 (JP) .............................. 2007-054226

(51) Int. Cl.
*G01N 21/00* (2006.01)

(52) U.S. Cl. ...................................... 356/445
(58) Field of Classification Search .......... 356/445–448
See application file for complete search history.

(56) References Cited

U.S. PATENT DOCUMENTS

| | | | |
|---|---|---|---|
| 6,891,620 B2 | 5/2005 | Mukai et al. | |
| 2007/0015288 A1 | 1/2007 | Hulteen et al. | |
| 2008/0037022 A1* | 2/2008 | Nishikawa et al. | 356/445 |

FOREIGN PATENT DOCUMENTS

| | | | |
|---|---|---|---|
| EP | 1 808 407 A | 7/2007 | |
| JP | 2000-356587 A | 12/2000 | |
| JP | 2002-357543 A | 12/2002 | |
| JP | 2003-185573 A | 7/2003 | |
| WO | 2006/035859 A | 4/2006 | |

OTHER PUBLICATIONS

European Search Report issued in European Application No. 08 15 2048 mailed Apr. 28, 2008, 11 pages.

Nishikawa T. et al. "A Nanobiosensor Fabricated by Nanoimprinting Technology" Transducers '07 & Eurosensors XXI 2007 14th International Conference on Solid-State Sensors, Actuators and Microsystems IEEE Piscataway, NJ, USA, 2007, pp. 2299-2302, XP002476183 ISBN: 1-4244-0841-5.

Nishikawa T. et al. "Development of New Localized Surface Plasmon Resonance Sensor with Nanoimprinting Technique" 2006 1st IEEE International Conference on Nano/Micro Engineered and Molecular Systems (IEEE Cat No. 06EX1290C) IEEE Piscataway, NJ, USA, 2006, pp. 4 pp., XP002476184 ISBN:1-4244-0140-2.

(Continued)

*Primary Examiner*—Michael P Stafira
(74) *Attorney, Agent, or Firm*—Osha Liang LLP

(57) ABSTRACT

A sensor chip has a metal layer formed on a surface of a substrate, where a plurality of microscopic concave part is formed in a measurement region of the surface of the metal layer. When light of linear polarization is irradiated onto the measurement region, local resonance electric field generates at opposing metal layer surfaces in the concave part. The reflected light thereof is received to measure reflectance. The light of linear polarization is irradiated so that the polarizing surface becomes orthogonal to the longitudinal direction of the concave part.

26 Claims, 55 Drawing Sheets

OTHER PUBLICATIONS

Matsushita Tomohiko et al. "New Localized Surface Plasmon Resonance Sensor Utilizing Nanoimprinting Technology" NSTI Nanotech. Conf. Trade Show Tech. Proc.; 2006 NSTI Nanotechnology Conference and Trade Show—NSTI Nanotech 2006 Technical Proceedings; 2006 NSTI Nanotechnology Conference and Trade Show—NSTI Nanotech 2006 Technical Proceedings 2006, vol. 1, 2006, pp. 58-61, X009098538.

Patent Abstracts of Japan, Publication No. 2003-185573, Publication Date: Jul. 3, 2003, 1 page.

Kyujung Kim et al. "Nanowire-based Enhancement of Localized Surface Plasmon Resonance for Highly Sensitive Detection: A Theoretical Study" Optics Express Opt. Soc. America USA, vol. 14, No. 25, Dec. 2006, XP002476185 ISSN:1094-4087.

Takayuki Okamoto, "Metal Nano-Particle Reaction and Biosensor Related Technology Research Report", Plasmonic Research Society (2002), 10 pages.

N. Felidj et al., "Controlling The Optical Response of Regular Arrays of Gold Particles for Surface-Enhanced Raman Scattering", Physical Review B, vol. 65, 075419 (2002), 9 pages.

* cited by examiner

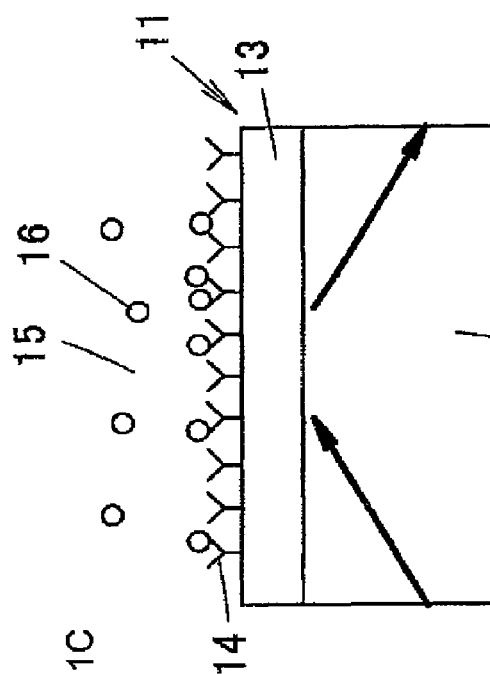
Fig. 1A
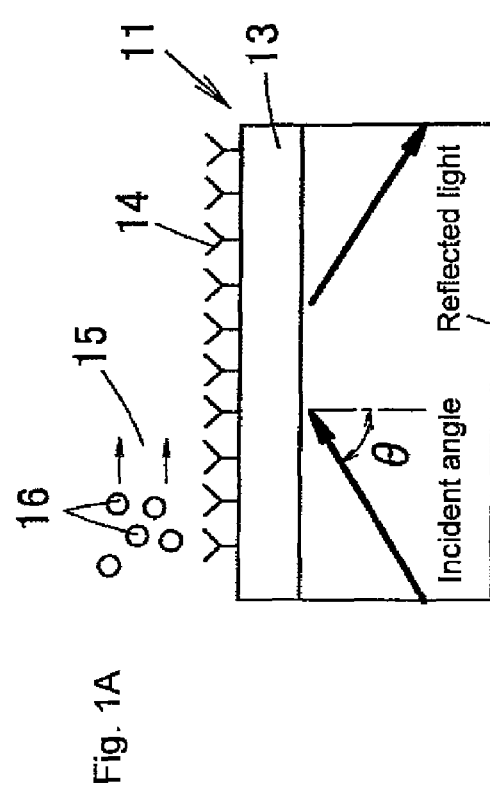
Fig. 1C
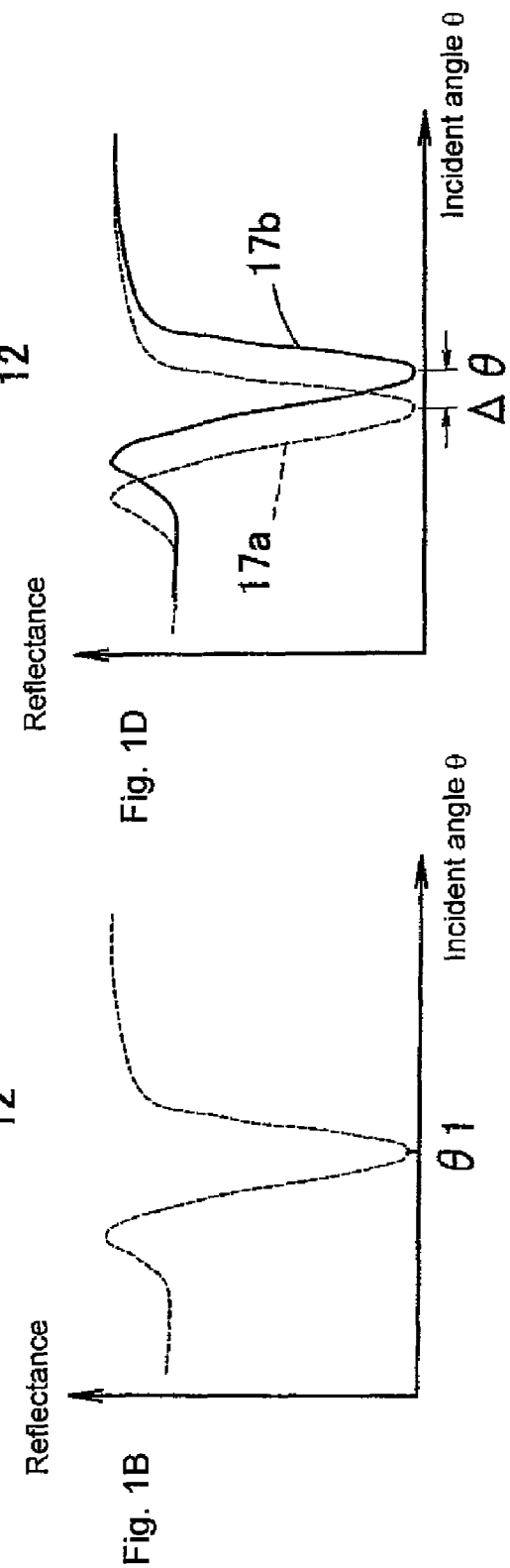
Fig. 1B
Fig. 1D
PRIOR ART

PRIOR ART

Incident light

Transmitted light

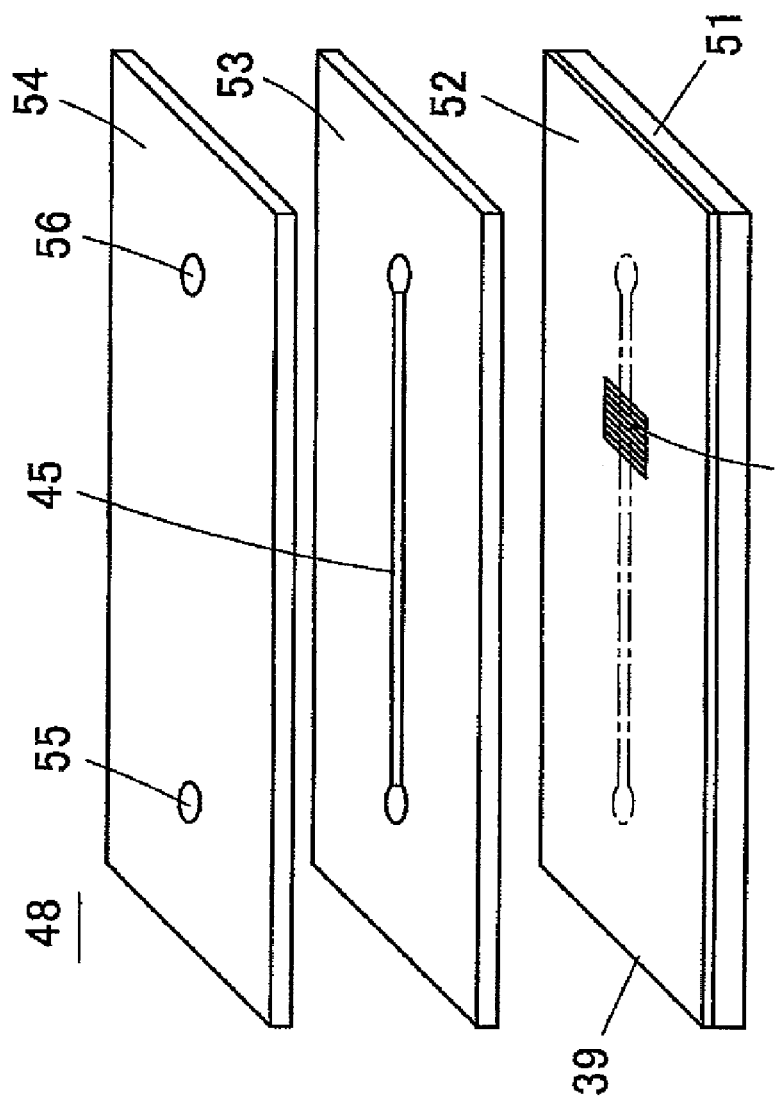
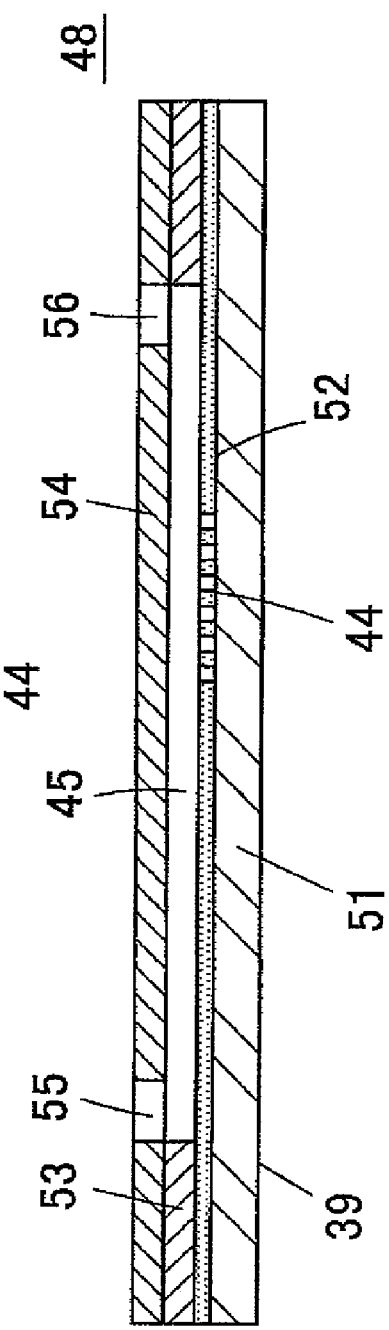
Fig. 10A
Fig. 10B

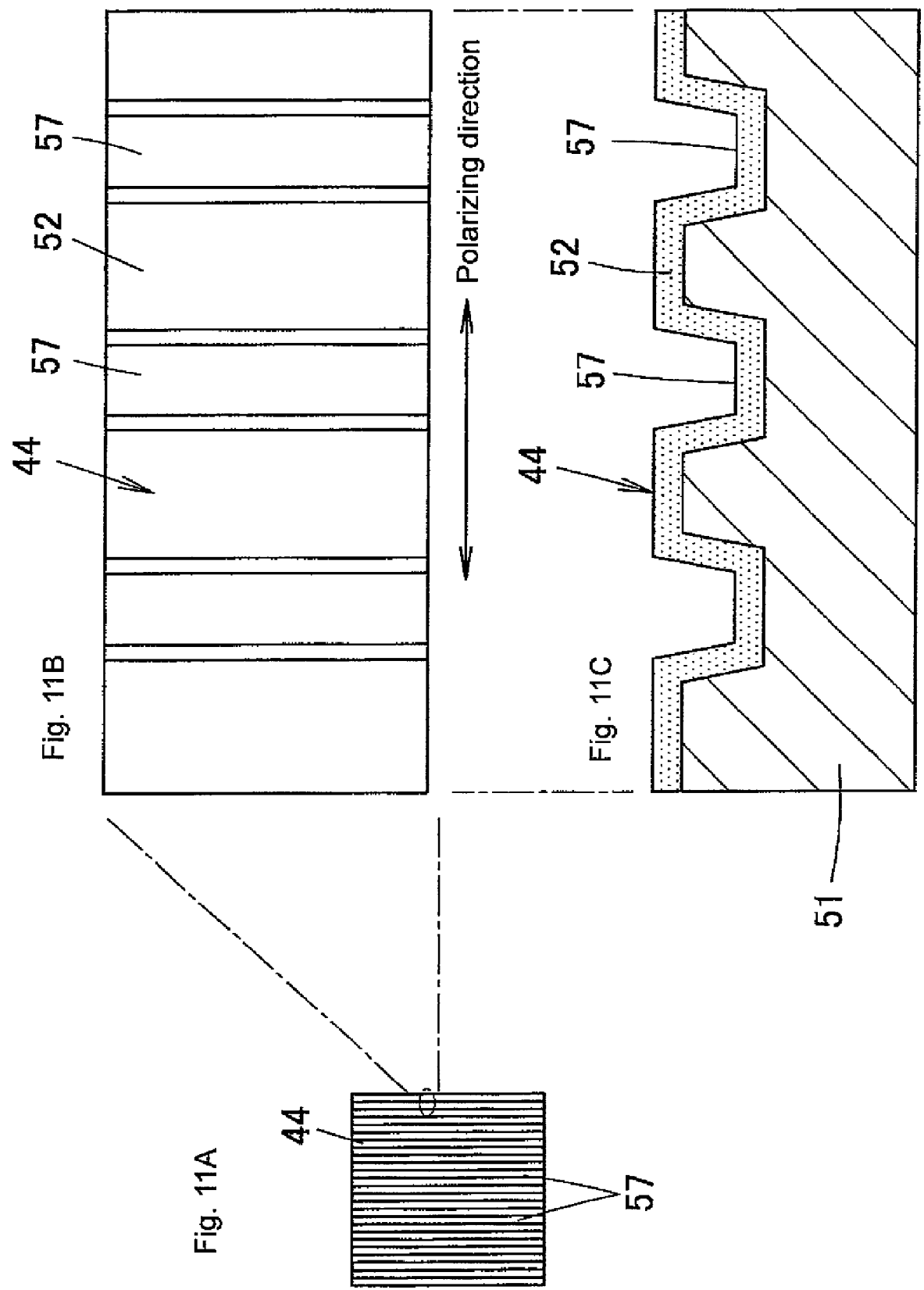

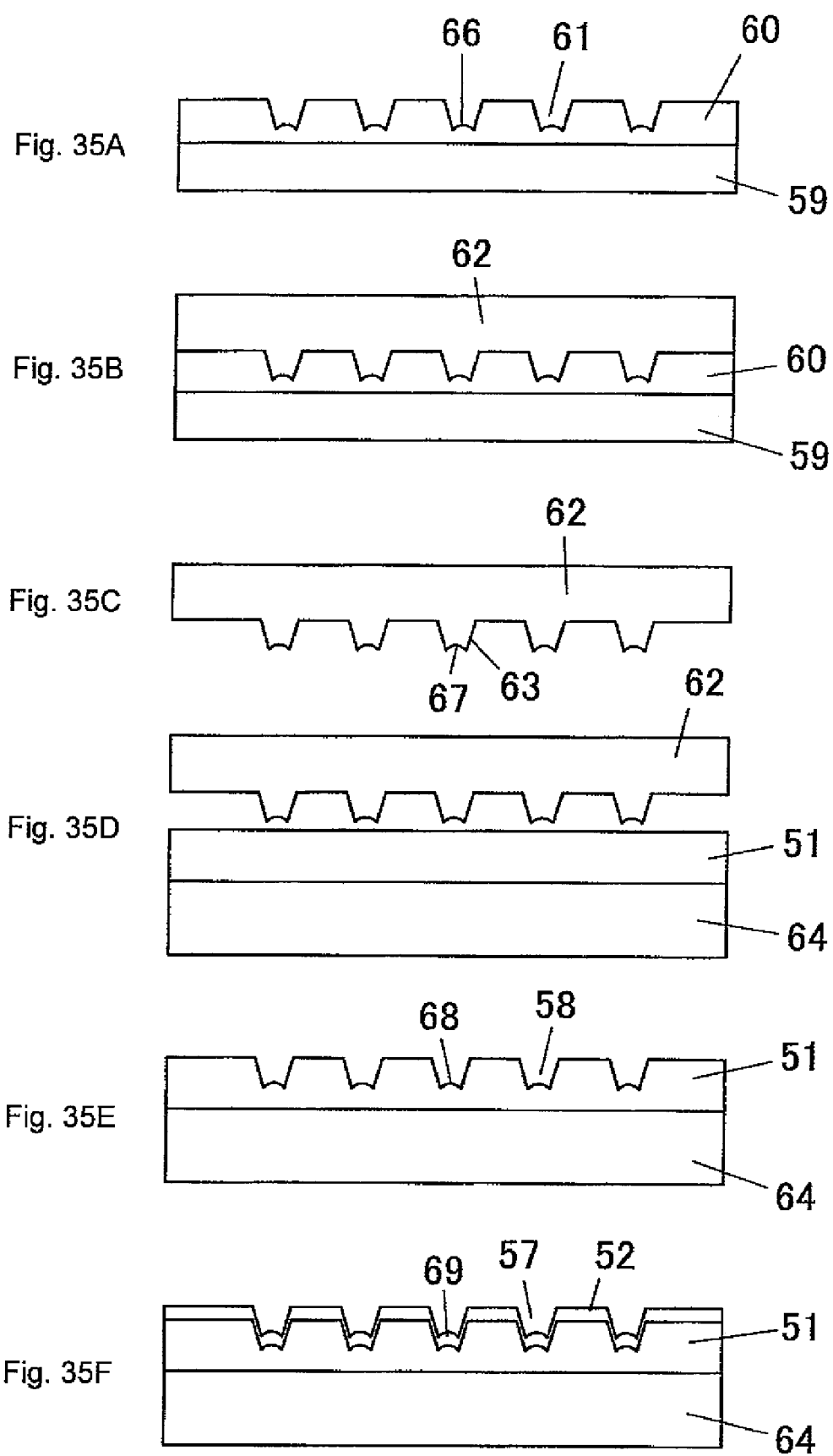

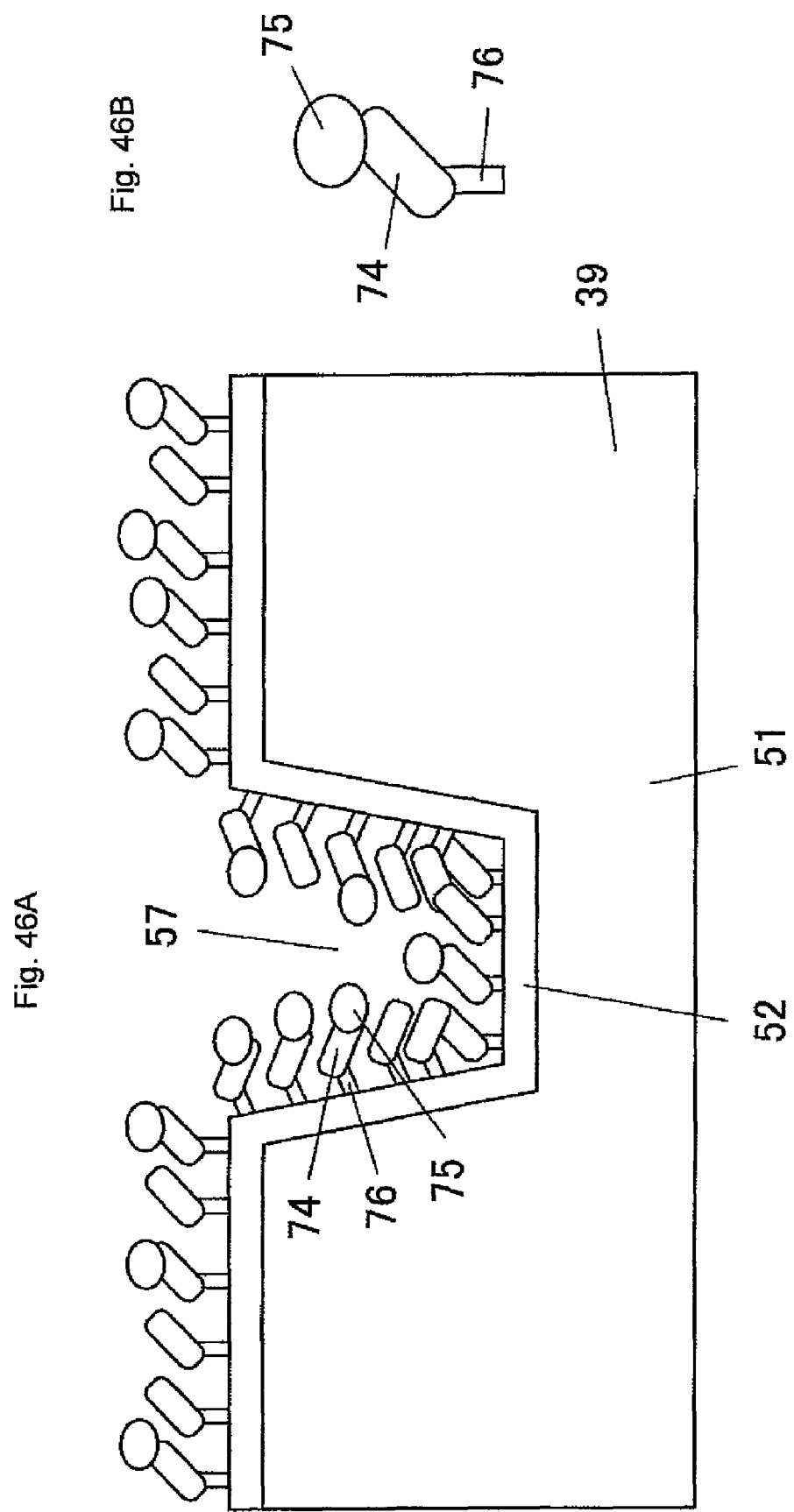

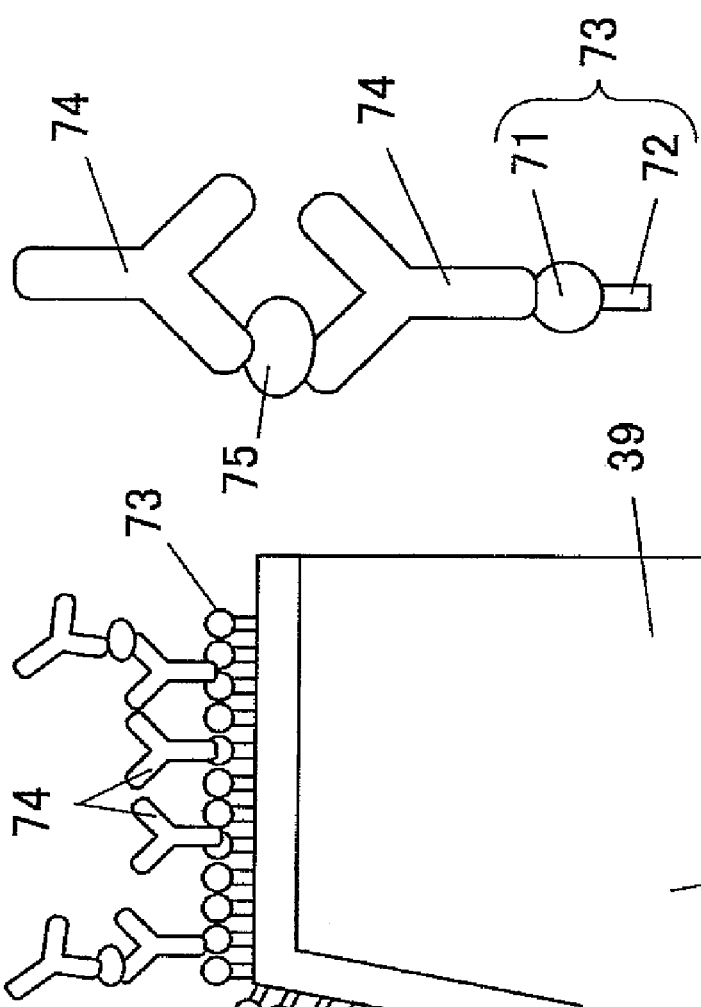
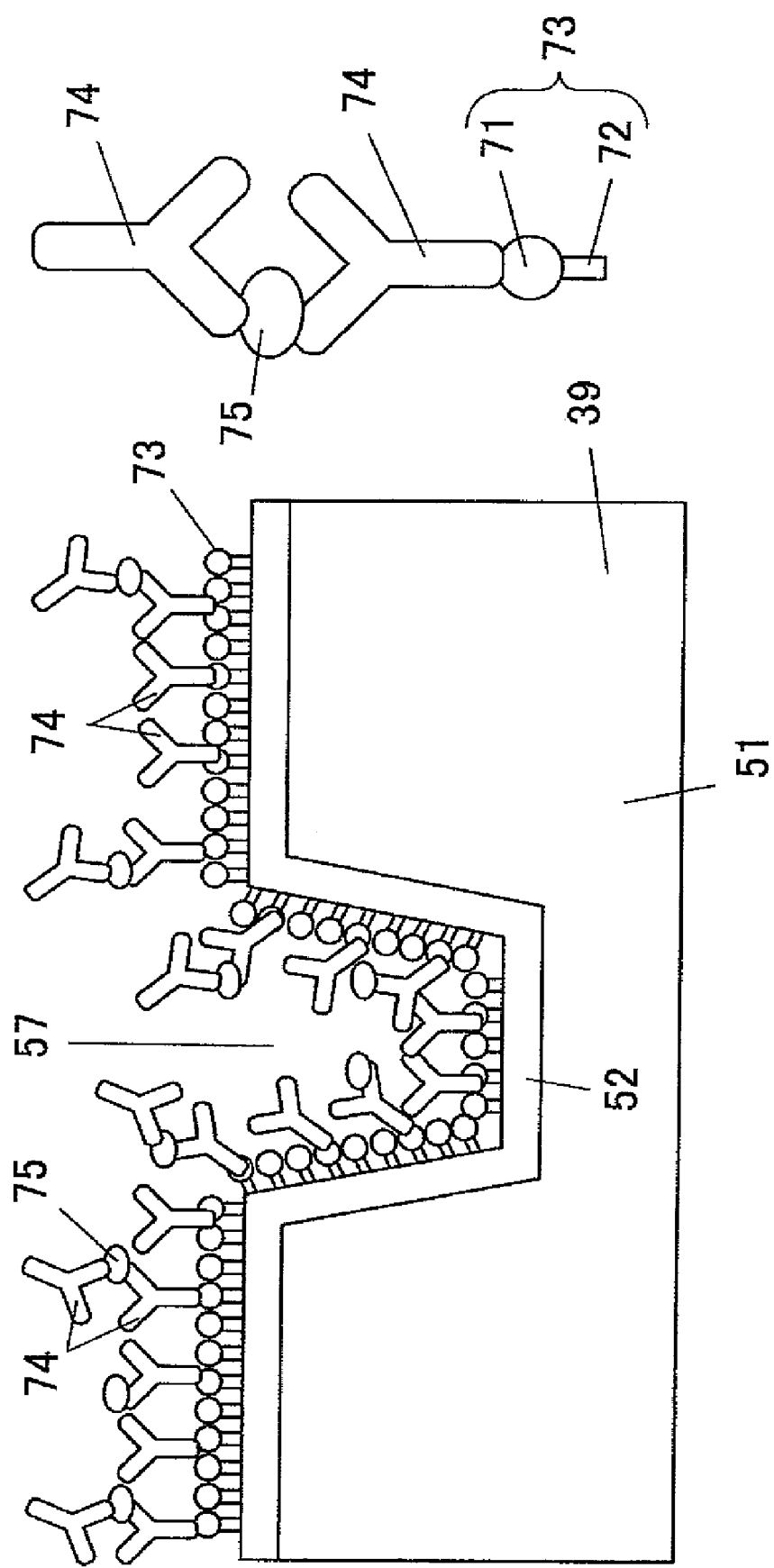

SURFACE PLASMON RESONANCE SENSOR AND SENSOR CHIP

BACKGROUND OF THE INVENTION

1. Technical Field

The present invention relates to a surface plasmon resonance sensor and a sensor chip. In particular, the present invention relates to a surface plasmon resonance sensor that uses a local surface plasmon resonance, and a surface plasmon resonance sensor chip.

2. Related Art

Human body consists of 60% water, and 40% of the remaining half protein, where the majority of the tissues, muscles, and skin of the human body consist of protein. Thus, a correlation is often recognized between the disease and the variation of the protein, where a specific protein increases in the body (e.g., in the blood) with progression of the disease in cancer, influenza, and other diseases.

Therefore, the affected site and the progressing state of the disease can be recognized by monitoring the state of a specific protein (presence, amount, etc. of a specific protein), and currently, a correlation with the disease is recognized for a few tens of types of proteins. For instance, a biological molecule that increases with progression of a tumor (cancer) is referred to as tumor marker, and different tumor markers are specified according to the site of origin of the tumor.

Biological molecules such as protein, DNA, and sugar chain in the living body are often related directly to the occurrence of disorder, and thus the mechanism of the disease can be understood and development of an effective drug can be carried out by analyzing the interaction between the biological molecules.

A tool for easily and conveniently measuring the presence and the quantity of a specific protein including the tumor marker at high accuracy includes a biosensor, and application to false diagnosis prevention, early diagnosis, preventive medical care, and the like is expected in the future.

A method of detecting the interaction of the biological molecules such as protein uses surface plasmon resonance. The surface plasmon resonance (SPR) is a resonance phenomenon that occurs by interaction between free electrons of the metal surface and electromagnetic wave (light), and is given attention as an easy and convenient method since the sample does not need to be labeled with fluorescent substance compared to the fluorescent detecting method. A sensor using surface plasmon resonance includes a propagation surface plasmon resonance sensor and a local surface plasmon resonance sensor.

The principle of the propagation surface plasmon resonance sensor will be briefly described with FIGS. 1A to 1D. As shown in FIGS. 1A and 1C, the propagation surface plasmon resonance sensor 11 has a metal film 13 made of Au, Ag, and the like having a thickness of about 50 nm formed on the surface of a glass substrate 12. The propagation surface plasmon resonance sensor 11 irradiates light from the glass substrate 12 side, and totally reflects the light at an interface of the glass substrate 12 and the metal film 13. The biological molecule or the like is sensed by receiving the totally reflected light, and measuring the reflectance of the light.

In other words, when carrying out reflectance measurement by changing the incident angle θ of the light, the reflecting angle greatly attenuates at a certain incident angle (resonance incident angle) θ1, as shown in FIG. 1B. When the light entering the interface of the glass substrate 12 and the metal film 13 is totally reflected at the relevant interface, evanescent light (near-field light) generated at the relevant interface and the surface plasmon wave of the metal interact. At a specific wavelength or a specific incident angle, the energy of the light is absorbed into the metal film 13 and changed to vibration energy of the free electrons in the metal film 13, whereby the reflectance of the light significantly lowers.

The resonance condition depends on the dielectric constant (index of refraction) of the peripheral substances of the metal film 13, and thus is used for a method of detecting change in characteristics of the peripheral substances at high sensitivity. In particular, when used as a biosensor, an antibody 14 (probe) that uniquely bonds with a specific protein (antigen) is immobilized on the surface of the metal film 13 in advance, as shown in FIG. 1A. If an antigen 16 that acts as a target is present in an introduced test sample 15, the antigen 16 and the antibody 14 uniquely bond, as shown in FIG. 1C. The index of refraction around the metal film 13 changes when the antigen 16 is bonded, and the resonance wavelength and the resonance incident angle change. Therefore, whether or not the antigen 16 is contained in the test sample 15 can be examined by measuring change in the resonance wavelength, change in the resonance incident angle, or temporal change in the resonance wavelength and the resonance incident angle at before and after introducing the test sample 15. At what extent of the concentration the antigen 16 is contained can also be examined.

FIG. 1D shows one example of a result of measuring the dependency of reflectance with respect to the incident angle θ. In FIG. 1D, a broken line shows a reflectance spectrum 17a before the test sample 15 is introduced, and a solid line shows a reflectance spectrum 17b after the test sample 15 is introduced and the antigen 16 is bonded to the antibody 14. Whether or not the test sample 15 contains the antigen 16 can be examined by measuring the change Δθ in resonance incident angle at before and after the test sample 15 is introduced. Furthermore, the concentration of the antigen 16 can also be examined, and the presence of a specific pathogenic agent, presence of disorder, and the like can be examined.

A prism is used to introduce light to the glass substrate in a general propagation surface plasmon resonance sensor. Thus, the optical system of the sensor becomes more complicating and larger, and furthermore, the sensor chip (glass substrate) and the prism need to be closely attached with matching oil. In order to resolve the difficulty in handling, Japanese Laid-Open Patent Publication No. 2002-357543 proposes a propagation surface plasmon resonance sensor that uses diffraction grating.

The propagation surface plasmon resonance sensor disclosed in Japanese Laid-Open Patent Publication No. 2002-357543 has a metal film 19 formed on a substrate 18, and a thin film discretely stacked on the metal film 19 to form a diffraction grating 20 (grating), as shown in FIG. 2.

In such propagation surface plasmon resonance sensor, when light is irradiated onto the diffraction grating 20, the irradiated light is reflected by the diffraction grating 20, and the evanescent light is generated by the diffraction phenomenon. The surface plasmon wave generates at the surface of the diffraction grating 20 when light is irradiated onto the diffraction grating 20. The evanescent light and the surface plasmon wave resonate thereby generating surface plasmon resonance when light of a certain wavelength is irradiated at a specific incident angle. Therefore, a specific antigen can be detected in such propagation surface plasmon resonance sensor by immobilizing the antibody on the diffraction grating 20.

The cross section of the diffraction grating type propagation SPR sensor may be a rectangular shape, but in most cases, the cross section is generally a sinusoidal wave shape.

The concave-convex part in the diffraction grating type propagation SPR sensor serves as diffraction grating, and thus the duty ratio thereof is desirably 1:1.

FIG. 3 shows a diffraction grating of concave-convex shape. Assume the pitch of the diffraction grating 20 is P, that is, the width of the convex part (light reflecting surface) is P/2, the width of the concave part as P/2, the incident angle of the incident light as $\theta$, and the exit angle of the diffracted light is $\phi$. The optical path difference of the light reflected at adjacent convex parts is, as apparent from FIG. 3, $$P \cos \theta - P \cos \phi$$

Therefore, the condition the phases of the reflected lights align and strengthen each other is, $$\cos \theta - \cos \phi = m \cdot \lambda/P$$

where $\lambda$ is the wavelength of the incident light. $m=0, \pm 1, \ldots$ is the diffraction order. The maximum value of the left side of the equation is 2, and thus $(\lambda/P)<2$ is necessary to cause diffraction.

In the diffraction grating type propagation SPR sensor, P>400 nm is a prerequisite as a condition for causing diffraction at the entire visible light region when using the light of visible light region ($\lambda=400\text{-}800$ nm) for a sensor.

In the diffraction grating type propagation SPR sensor, the light is generally entered in a diagonal direction.

Consequently, the diffraction grating type SPR sensor includes a wide sensing area of a few hundred nm.

The local surface plasmon resonance sensor will now be described. The local surface plasmon resonance sensor has the free electron vibration caused by the surface plasmon resonance standing in the local region of the metal nano configuration, and the sensing region thereof is known to be very small of a few dozen nm compared to the propagation surface plasmon resonance sensor.

The local surface plasmon sensor includes that disclosed in Japanese Laid-Open Patent Publication No. 2000-356587. The local surface plasmon resonance sensor 21 realizes the metal nano configuration using metal fine particles (metal nano fine particles) having an average particle diameter of a few dozen nm. In the sensor 21, a glass substrate 22 is immersed in colloidal solution of metal fine particles, and metal fine particles 23 are distributed over the surface of the glass substrate 22. As shown in FIG. 4A, the light is perpendicularly entered from the back surface side of the glass substrate 22, and the intensity of the light transmitted through the glass substrate 22 is measured. The received transmitted light is divided by a spectroscopic means to obtain absorbance at each wavelength, so that a peak of the absorbance is found at a certain wavelength (resonance wavelength), as shown in FIG. 4B.

The resonance phenomenon is such in which the free electrons in the metal fine particles 23 vibrate by alternating current electric field of the light (electromagnetic wave), the light and the free electrons vibrate at a certain vibration frequency so that the free electrons absorb the light energy, and the absorbance peaks at the resonance wavelength.

Since such phenomenon is also influenced by dielectric constant (index of refraction) of the periphery of the metal fine particles 23, the absorbance changes when some kind of dielectric substance (e.g., antigen) attaches to the metal fine particle. For instance, the absorbance characteristic 24a shown with a broken line in FIG. 4B before the dielectric substance attaches to the metal fine particle changes to the absorbance characteristic 24b shown with a solid line in FIG. 4B after attachment. Therefore, the presence of attachment and the quantity of attachment of the dielectric substance can be detected by reading change in peak value of the absorbance.

The surface plasmon resonance sensor includes propagation surface plasmon resonance sensor and local surface plasmon resonance sensor as described above. However, the sensing area is large or a few hundred nm from the surface of the glass substrate compared to the size of the protein (around ten nm) in the propagation surface plasmon resonance sensor. Thus, the sensor is likely to be influenced by temperature change of the test sample and foreign substances (e.g., protein other than the testing target) in the test sample, and is also sensitive to antigen that floats in the test sample without being bonded to the antibody in biosensors. These become the cause of noise, and thus it becomes difficult to manufacture a sensor having small S/N ratio and high sensitivity. In order to manufacture a sensor of high sensitivity, a step of removing foreign substances that become the cause of noise, and a strict temperature controlling means for maintaining the temperature of the test sample constant are required, whereby the device becomes larger and the device cost becomes expensive.

In the local surface plasmon resonance sensor, on the other hand, the near-field that generates at the surface of the metal fine particles (metal nano fine particles) becomes the sensing region, and thus a sensitivity region of a few dozen nm of lower than or equal to a diffraction limit can be achieved. As a result, the local surface plasmon resonance sensor is not sensitive to testing objects that float in the region distant from the metal fine particles, and is sensitive only to the testing object attached to a very narrow region of the surface of the metal fine particle surface, and thus a sensor of high sensitivity can be realized. According to such sensor, a strict temperature controlling means for controlling the temperature of the test sample to a constant temperature is not necessary.

The local surface plasmon resonance sensor using metal fine particles is not sensitive to testing object floating distant from the metal fine particles, and thus the noise component reduces, and high sensitivity is obtained in such regards compared to the propagation surface plasmon resonance sensor. However, in sensors using surface plasmon resonance generated at the metal fine particles such as Au and Ag, the intensity of the signal obtained from the testing object attached to the surface of the metal fine particles is small, and thus the sensitivity is still low or the sensitivity is not sufficient in such regards.

"Investigation Report on Metal Nano Particle Interaction and Biosensor" (FIG. 2) by Takayuki Okamoto, Plasmonic study group, 2002 Grants in Aid for Scientific Research (basic research C), research progress report; (http://www.plasmon.jp/index.html) is a research paper written by the inventor of Japanese Laid-Open Patent Publication No. 2000-356587. FIG. 5 shows a view cited from "Investigation Report on Metal Nano Particle Interaction and Biosensor" (FIG. 2) by Takayuki Okamoto, Plasmonic study group, 2002 Grants in Aid for Scientific Research (basic research C), research progress report; http://www.plasmon.jp/index.html (FIG. 2), showing "absorption spectrum of when the glass substrate deposited with gold nano particles having an average diameter of 20 nm is immersed in a liquid having various indexes of refraction". The change in the sensitivity of the sensor, that is, the resonance wavelength in a case of index of refraction of a medium contacting the sensor changed by one is obtained based on FIG. 5. The sensitivity is about 100 nm/RIU, and a sufficient sensitivity cannot be obtained.

It is noted that from FIG. 5, such sensitivity value was calculated by reading the change in resonance wavelength as 30 nm when the index of refraction of the medium was changed from 1.333 (water) to 1.737 (diiodemethane).

Sensitivity=30/(1.737−1.333)=74 [nm/RIU]

The sensitivity of the sensor was about 100 nm/RIU approximating to be slightly larger than such value.

A method of immobilizing the metal fine particles on the glass substrate by immersing the glass substrate in a colloidal solution is adopted in the local surface plasmon resonance sensor of Japanese Laid-Open Patent Publication No. 2000-356587, where the distribution density of the metal fine particles is not constant even if manufactured with the same process and the variation in the distribution density is large. Furthermore, the metal fine particles can be relatively easily separated if the distribution density of the metal fine particles is small, as shown in FIG. 6A, but the metal fine particles condense as shown within a circle in FIG. 6B if the distribution density of the metal fine particles becomes large, and it becomes difficult to stabilize the quality. Therefore, a problem of mass production arises when commercializing, and in particular, mass productivity becomes worse when the distribution density of the metal fine particles is increased to enhance the sensitivity.

N. Felidj et al. "Controlling the optical response of regular arrays of gold particles for surface-enhanced Raman scattering", Phys. Rev. B 65, 075419 (2002) shows a method of manufacturing a metal nano configuration in which the metal fine particles are evenly arrayed using an electron beam. This method will be described according to FIGS. 7A to 7F. First, as shown in FIG. 7A, a photoresist 26 is coated on the entire surface of a substrate 25. Then, as shown in FIG. 7B, an electron beam 27 is sequentially irradiated onto the photoresist 26 in a metal fine particle forming device on the substrate 25 to solubilize the photoresist 26 at the irradiating position of the electron beam 27. The photoresist 26 is subjected to development process, whereby, the solubilized portion of the photoresist 26 is removed, and a hole 28 is opened at the metal fine particle forming position in the photoresist 26, as shown in FIG. 7C. As shown in FIG. 7D, Cr29 is then deposited from above the photoresist 26, so that Cr29 is also deposited on the surface of the substrate 25 exposed in the hole 28. Thereafter, as shown in FIG. 7E, Au30 is deposited from above the photoresist 26, so that Au30 is also deposited on the Cr29 in the hole 28. The substrate 25 is thereafter immersed in the etchant to strip the photoresist 26, whereby a metal fine particle (Au30) is formed in a desired pattern at the surface of the substrate 25, as shown in FIG. 7F. FIG. 8 shows a view showing a pattern of the metal fine particle obtained in this manner (cited from N. Felidj et al. "Controlling the optical response of regular arrays of gold particles for surface-enhanced Raman scattering", Phys. Rev. B 65, 075419 (2002), where the portion that appears white is the metal fine particle.

According to the method of FIG. 7, the metal fine particle can be formed with an arbitrary arrangement pattern, but it takes a few hours in the step of irradiating the electron beam since the pattern is drawn one at a time with the squeezed electron beam. Therefore, about half a day is required to manufacture one sensor chip, and the manufacturing throughput is very low. Therefore, mass production is difficult with such method, and realization of an inexpensive sensor chip is impossible.

SUMMARY

In accordance with one aspect of the present invention, a surface plasmon resonance sensor of the present invention includes a surface plasmon resonance sensor including a surface plasmon resonance sensor chip; a light source for irradiating light onto the surface plasmon resonance sensor chip; and a photodetector for receiving light reflected by the surface plasmon resonance sensor chip; wherein the surface plasmon resonance sensor chip includes a substrate, and a metal layer formed so as to cover at least one part of a surface of the substrate, a plurality of concave parts being formed at a surface of the metal layer; an inner wall face in the concave part has at least one set of opposing metal layer surfaces, a local resonance electric field being generated at the opposing metal layer surfaces; and the light exit from the light source, entered to the surface of the sensor chip, and reflected at a region including the concave part of the surface of the metal layer is received by the photodetector to measure a reflectance in the sensor chip or a light intensity received at the photodetector. The local resonance electric field refers to that in which a resonance electric field does not propagate along the metal surface, and a region of the electric field enhanced by resonance is smaller than a diffraction limit of the incident light.

In accordance with another aspect of the present invention, a surface plasmon resonance sensor chip of the present invention includes a surface plasmon resonance sensor chip including a substrate; and a metal layer formed so as to cover at least one part of a surface of the substrate; a light being received at a surface of the metal layer; wherein a plurality of concave parts is formed at the surface of the metal layer; an inner wall face in the concave part has at least one set of opposing metal layer surfaces, a local resonance electric field being generated at the opposing metal layer surfaces.

In the surface plasmon resonance sensor chip of the present invention, when light perpendicularly enters the region including a concave part of nano size formed in the metal layer, bonding occurs between the free electrons at the opposing metal side faces in the concave part and the incident light, strong electric field concentrates at the inside of the concave part, and a strong local surface plasmon resonance generates. When surface plasmon resonance generates, the energy of the light is absorbed by the surface plasmon wave of the metal layer, and thus the reflectance of light or the light intensity received by the photodetector lowers at a certain wavelength (resonance wavelength).

In accordance with another aspect of the present invention, a method of manufacturing a surface plasmon resonance sensor of the present invention includes a method of manufacturing the surface plasmon resonance sensor chip according to the present invention, the method includes the steps of manufacturing a stamper having a convex pattern; transferring the convex pattern of the stamper onto a resin by pressing the stamper to a non-cured resin, and curing the resin to mold the substrate and form a depression at a surface of the substrate by an inverted shape of the convex pattern; and depositing metal on the surface of the substrate to form the metal layer, and forming the concave part by a metal layer formed reflecting the shape of the depression.

A method for solving the problems in the present invention has features appropriately combining the components, and thus the present invention allows numerous variations by combining the components.

BRIEF DESCRIPTION OF THE DRAWINGS

FIGS. 1A to 1D show views describing a principle of a propagation surface plasmon resonance sensor in prior art;

FIG. 10A shows an exploded perspective view of a configuration of a flow cell used in the local SPR sensor of FIG. 9, and FIG. 10B shows a cross sectional view of an assembled state;

FIG. 11A shows a plan view of a measurement region of the flow cell, FIG. 11B shows a view enlarging one part of FIG. 11A, and FIG. 11C shows a cross sectional view of FIG. 11B;

FIGS. 35A to 35F show views describing the manufacturing steps of a sensor chip of a second embodiment;

FIG. 46A shows a partial cross sectional view of a sensor chip immobilized with an antigen using a protein in which a self-organized film formation site and a single chain part of the antibody are fused; FIG. 46B shows a view of a state in which the antigen is uniquely bound to the antibody in which the self-organized film formation site and the single chain part are fused;

FIG. 47A shows a partial cross sectional view showing a sensor chip immobilized with an antibody and an antigen through a sandwich method; FIG. 47B shows a view of a state in which two antibodies are bound with the antigen in between;

DETAILED DESCRIPTION

In view of the above technical problems, it is an object of the present invention to provide a local surface plasmon resonance sensor having higher sensitivity than the conventional local surface plasmon resonance sensor and a surface plasmon resonance sensor chip. It is another object of the present invention to provide a local surface plasmon resonance sensor chip capable of realizing stability of the manufacturing process and low cost.

The embodiments of the present invention will be described in detail below with reference to the drawings.

First Embodiment

Figure 9:
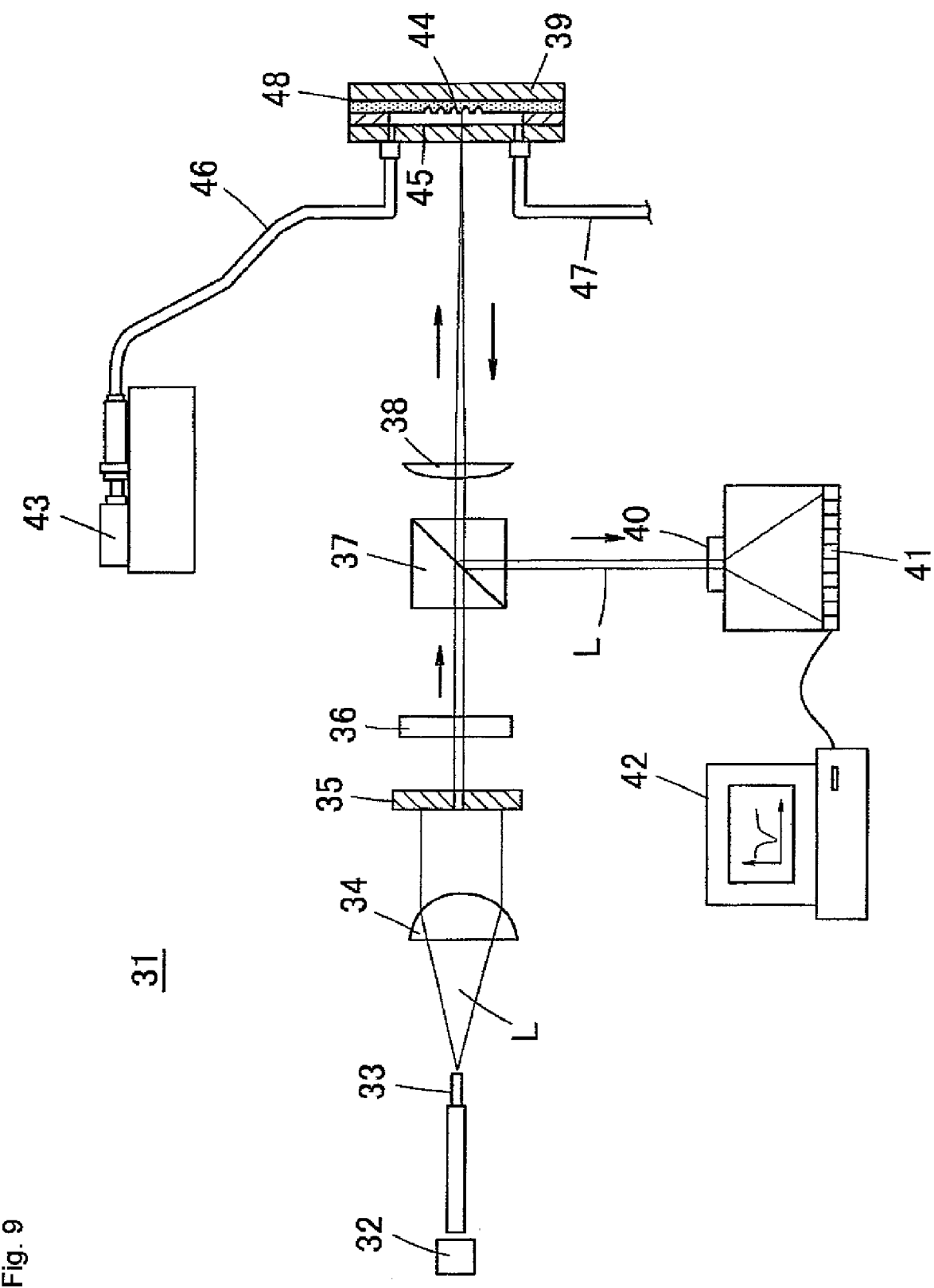
FIG. 9 shows a view of a configuration of a local surface plasmon resonance sensor according to a first embodiment of the present invention.

FIG. 9 shows a schematic view of a basic configuration of a local surface plasmon resonance sensor (hereinafter referred to as local SPR sensor) 31 according to a first embodiment of the present invention. The local SPR sensor 31 is configured by a light source 32 such as halogen lamp, an optical fiber 33, a collimator lens 34, a collimator plate 35 with pin holes, a polarization plate 36, a beam splitter 37 (or half mirror), an objective lens 38, a flow cell 48, a spectroscope 40, a photodetector 41, a data processing device 42, and a syringe pump 43.

The light source 32 is desirably that which irradiates a white light such as a halogen lamp, but may be of any type as long as it has light of a wavelength region used for measurement. Light L exit from the light source 32 is guided to the collimator lens 34 by the optical fiber 33. The collimator lens 34 collimates the light L exit from the distal end of the optical fiber 33, and passes the light as parallel beam. The light L collimated in the collimator lens 34 is passed through the pin holes of the collimator lens 35 to become a narrowed parallel beam. Of the parallel beam that has passed through the pin holes, only a linear polarization having a certain polarizing surface (e.g., polarizing surface parallel to the plane of drawing of FIG. 9) passes through the polarization plate 36. In the present invention, the vibration surface of the electric field of the light (electromagnetic wave) is defined as the polarizing surface, and the direction of such electric field is defined as the polarizing direction.

The light L of linear polarization that has passed through the polarization plate 36 enters the beam splitter 37, and only the light of about ½ of the incident light quantity straightly transmits through the beam splitter 37. The parallel beam that has transmitted through the beam splitter 37 is passed through the objective lens 38, and collected on a measurement region 44 (region formed with concave structure) in the flow cell 48 by the objective lens 38.

A flow path 45 for passing a test sample solution is formed in the flow cell 48, and the measurement region 44 is arranged facing the flow path 45. The test sample solution is supplied to the flow path 45 by the syringe pump 43 through a liquid feeding tube 46, and the test sample solution passing through the flow path 45 is collected through a collecting tube 47.

The light L irradiated on the measurement region 44 of the flow cell 48 is reflected by the measurement region 44, and returned in the original direction. The measurement light returned in the original direction passes through the objective lens 38 and again becomes a parallel beam, and then enters the beam splitter 37. Of the measurement light that has entered the beam splitter 37, only about ½ of such light quantity is reflected in a direction of 90 degrees at a laminated surface in the beam splitter 37. The objective lens 38 used has a sufficient opening diameter to be able to collect the light reflected in each direction at the measurement region 44.

The light L reflected by the beam splitter 37 is passed through the spectroscope 40 and divided into lights of each wavelength, and then received by the photodetector 41. The photodetector 41 is configured by a photodiode array, a CCD, and the like having a plurality of light receiving surfaces, where the light receiving surfaces are lined parallel to the light dividing direction. The light divided by the spectroscope 40 is received by the photodetector 41, so that the light intensity for each wavelength can be detected.

The data processing device 42 is provided with light intensity of each wavelength of the light irradiating the flow cell 48 as data in advance. Therefore, the spectroscopic characterization (reflectance spectrum) etc. of the reflectance of each wavelength at the flow cell 48 can be obtained by comparing the data provided in advance and the light intensity of each wavelength detected by the photodetector 41 in the data processing device 42.

The configuration of the flow cell 48 will now be described in detail. FIG. 10A shows an exploded perspective view of a configuration of the flow cell 48, and FIG. 10B shows a cross sectional view of an assembled state. The flow cell 49 has a three-layer configuration in which a spacer 53 and a cover 54 are stacked on a surface plasmon resonance sensor chip (hereinafter referred to as sensor chip) 39. The sensor chip 39 has a metal layer 52 made of metal thin-film of Au, Ag, or the like formed on the entire surface of a substrate 51, and has the measurement region 44 formed at one part of the metal layer 52. The substrate 51 is preferably a slide glass or a glass plate but may be nontransparent. The metal layer 52 does not need to be arranged on the entire surface of the substrate 51, and may be formed only at a small region including the measurement region 44, or may be formed only at the measurement region 44.

The flow path 45 for passing the test sample solution is formed in the spacer 53, where the flow path 45 is arranged so as to pass the upper surface of the measurement region 44. A supply port 55 and a discharge port 56 are opened in the cover 54 at positions facing both ends of the flow path 45. The liquid feeding tube 46 is connected to the supply port 55, from which the test sample solution is supplied into the flow path 45. The collecting tube 47 is connected to the discharge port 56, from which the test sample solution that has passed through the flow path 45 is discharged and collected in the collecting tube 47. The cover 54 and the spacer 53 are desirably transparent or semi-transparent so that non-used and used flow cells 48 can be distinguished.

FIG. 11A shows a plan view of the measurement region 44 in an enlarged manner, FIG. 11B shows a view enlarging one part of FIG. 11A, and FIG. 11C shows a cross sectional view of FIG. 11B. In the measurement region 44, a plurality of microscopic concave parts 57 (concave structure by metal thin-film) is formed at the surface of the metal layer 52. The concave part 57 is formed to a square groove shape, and is linearly extended from end to end of the measurement region 44. The plurality of concave parts 57 are arranged parallel to each other. In particular, the concave parts 57 are desirably formed on a periodic basis at a constant pitch. The inside of the concave part 57 is surrounded by the metal layer 52 excluding the opening, and in particular, the metal layers 52 face each other at the inner wall faces on both sides. The metal layer 52 at the bottom surface of the concave part 57 is formed flat.

The direction of the measurement region 44 in the flow cell 48 is not particularly limited from optical reasons. For instance, the longitudinal direction of the concave part 57 may be formed so as to be orthogonal to the liquid feeding direction of the flow path 45 as in FIG. 10, or the longitudinal direction of the concave part 57 may be formed so as to be parallel to the liquid feeding direction of the flow path 45.

Figure 12:
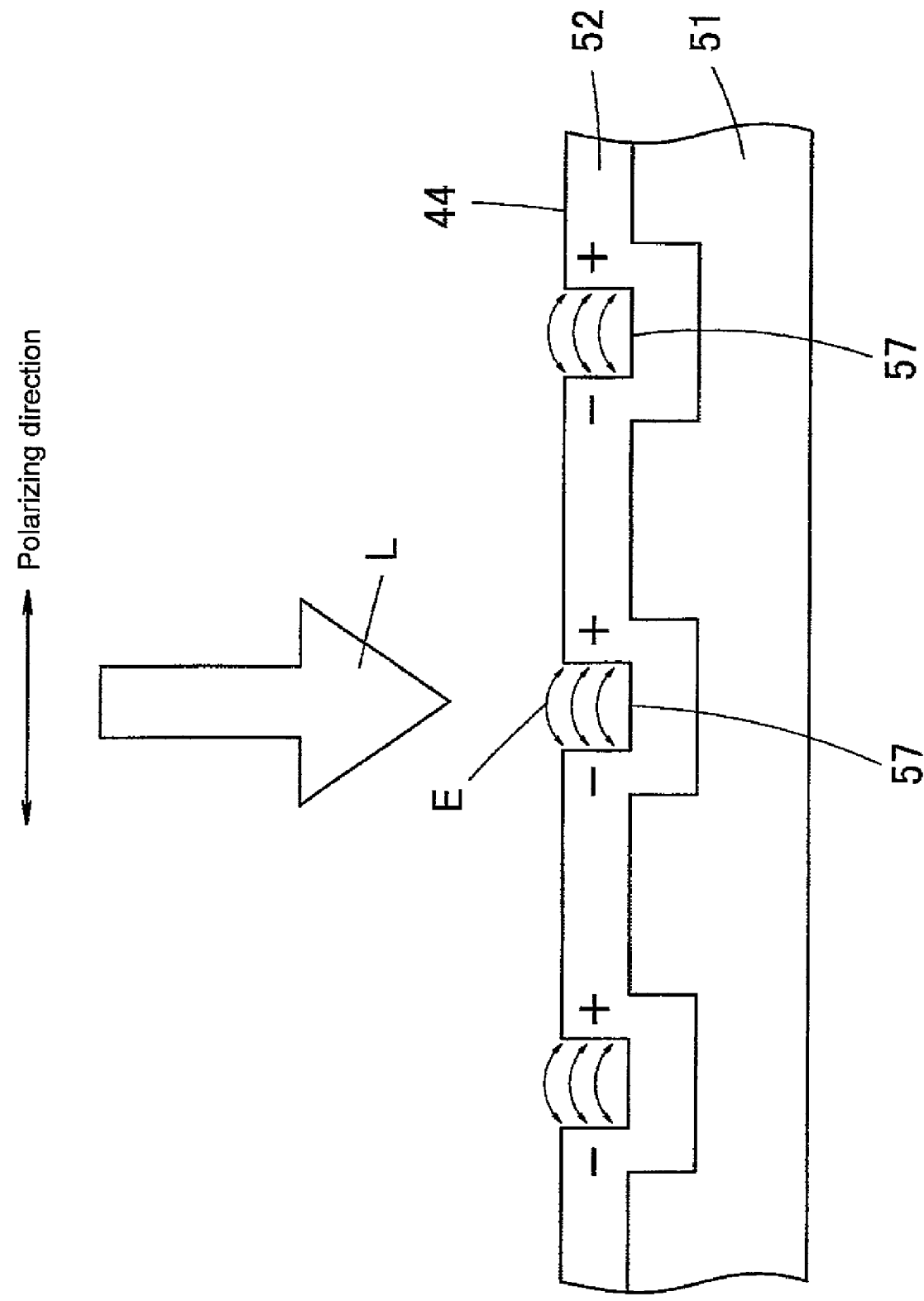
FIG. 12 shows a cross sectional view showing a relationship between a polarizing surface of the light entering the measurement region and a longitudinal direction of a concave part.

As shown in FIG. 12, the flow cell 48 is arranged in the local SPR sensor 31 so that the light L of linear polarization that has transmitted through the polarization plate 36 enters perpendicular to the measurement region 44 and so that the polarizing surface of the light L of linear polarization becomes orthogonal to the longitudinal direction of the concave part 57.

Figure 13:
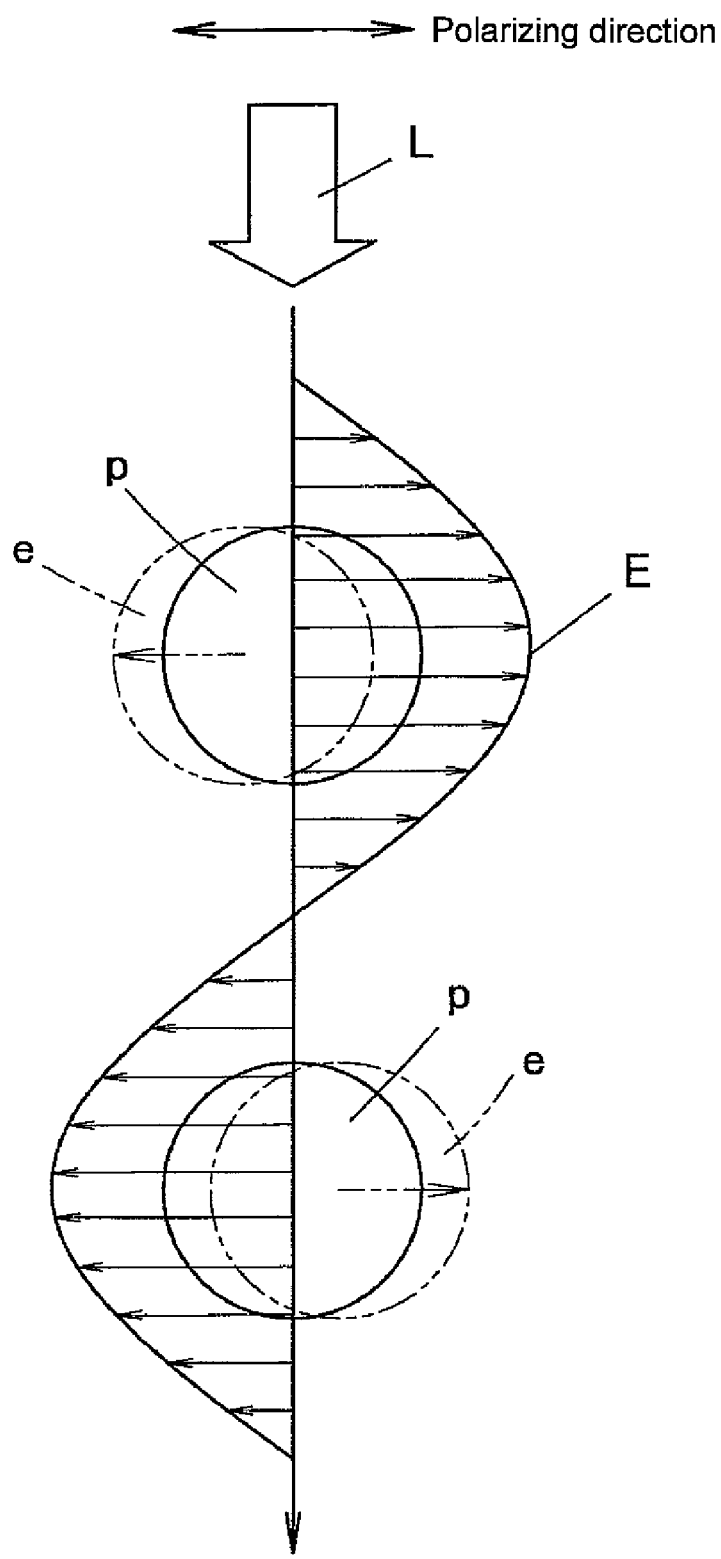
FIG. 13 shows a schematic view of an electric field of the light that has entered a metal fine particle.

When the light L of linear polarization perpendicularly enters the measurement region 44 in such arrangement, an electric field E generates between both side wall faces of the concave part 57 as shown in FIG. 12 due to the light entered into the concave part 57. "+" and "−" in FIG. 12 represent positive and negative of the electric field at the surface of the metal layer 52, which change with time according to the direction of the electric field component of the light. FIG. 13 shows a schematic view of the electric field E of the light L that has entered the metal fine particles of the metal layer 52. When the light L enters the metal fine particles, an electron cloud e of the metal fine particle p is influenced thereby, and displaces and vibrates, whereby surface plasmon wave generates at both side wall faces of the metal fine particle. The light that has entered the metal layer 52 with the concave part 57 generates the electric field E at both ends of the concave part 57, where the vibration of the electric field and the natural vibration of the free electrons in the metal layer 52 bond to generate the local SPR. Therefore, the energy of the light that has entered the metal layer 52 concentrate at the concave part 57 due to the SPR, and one part of the light that has entered the metal layer 52 is absorbed.

As a result, the reflectance obtained from the light received by the photodetector 41 becomes small at a certain specific wavelength (resonance wavelength). Since such specific wavelength changes by the index of refraction of the test sample solution, the index of refraction, the type, and the like of the dielectric substance contained in the test sample solution can be tested by examining the wavelength of the minimum point of the reflectance or its change. As hereinafter described, the presence and the content of a specific protein contained in the test sample solution can be tested by using an antibody etc. for uniquely bonding the specific protein.

In order to contribute all the incident electric field to the same resonance mode in such local SPR sensor 31, a configuration that is considered efficient has each concave part 57 formed so that the respective longitudinal direction becomes parallel to each other, and the light of linear polarization entered so that the polarizing surface becomes orthogonal to the longitudinal direction of each concave part 57, so that the entire incident light contributes to resonance.

In such sensor chip 39, the width of the minimum point (low peak) of the reflectance becomes wide if the width and the depth of the concave part 57 are uneven, and thus the width and the depth of each concave part 57 are desirably the same. The pitch at which the concave parts 57 are arrayed is desirably constant. Therefore, the concave part 57 having the same cross sectional shape is desirably periodically formed.

(Relationship of the Shape and Size of the Concave Part and the Characteristics of the Chip Sensor)

Reports have been conventionally made that when the metal fine particles are brought close to each other, enhancement in a very strong electric field occurs at the gap portion between the metal fine particles. Thus, in the sensor chip 39 of the present invention as well, a strong polarization occurs between the side wall faces and a strong resonance electric field generates in the concave part 57 by providing an appropriate interval between the side wall faces on both sides in the concave part 57 (hereinafter also referred to as concave structure) formed at the surface of the metal layer 52, whereby sensing of higher sensitivity than the conventional local surface plasmon resonance sensor in which the metal fine particles are dispersed can be realized.

First, a prototype of the sensor chip 39 was manufactured, and then the reflectance spectrum was measured, but prior to this, a simulation model same as the prototype had been manufactured, and the reflectance spectrum was obtained through computer simulation.

Figure 14:
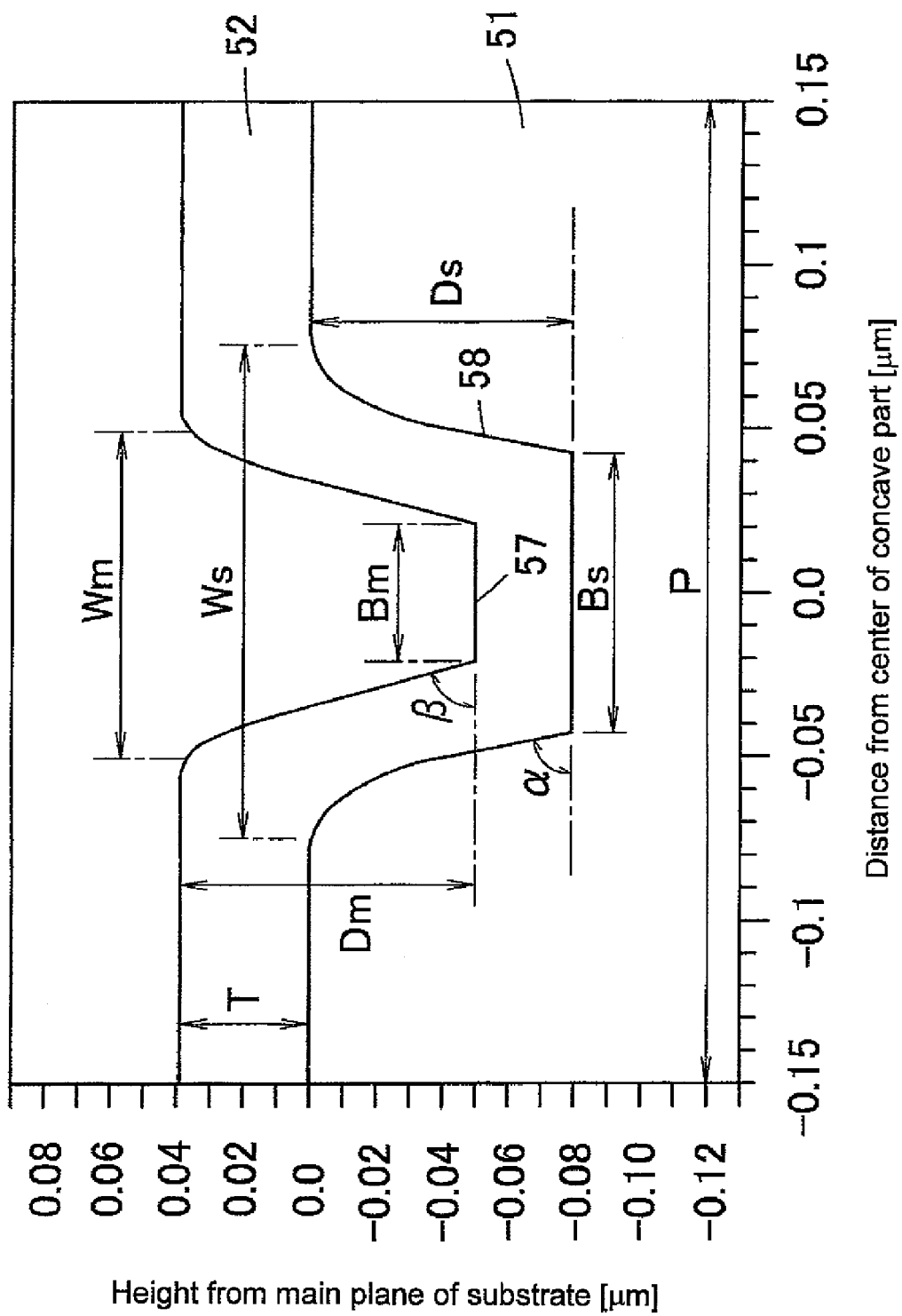
FIG. 14 shows a view of a cross sectional shape of one concave part in a prototype of the first embodiment.

FIG. 14 shows a cross sectional view of the concave part 57 of one unit in the prototype. In such prototype, a depression 58 formed in the substrate 51 made of resin has a width at the bottom surface of $B_s=85$ nm, a width of an opening of $W_s=156$ nm, a depth of $D_s=79$ nm, and an inclination angle of the side wall face of $\alpha=79$ degrees. The metal layer 52 (Au thin-film) having a film thickness of $T=39$ nm was deposited on the surface of the substrate 51, where the concave part 57 formed in the depression 58 by the metal layer 52 has a width at the bottom surface of $B_m=42$ nm, a width of an opening of $W_m=113$ nm, a depth of $D_m=89$ nm, and an inclination angle of the side wall face of $\beta=74.5$ degrees. The depression 58 and the concave part 57 are arrayed in parallel at a constant pitch of $P=300$ nm. Furthermore, the index of refraction of the substrate 51 is 1.49, where the test sample solution contacting the metal layer 52 has an index of refraction of $n=1.00$, $n=1.33$, or $n=1.36$.

Figure 15:
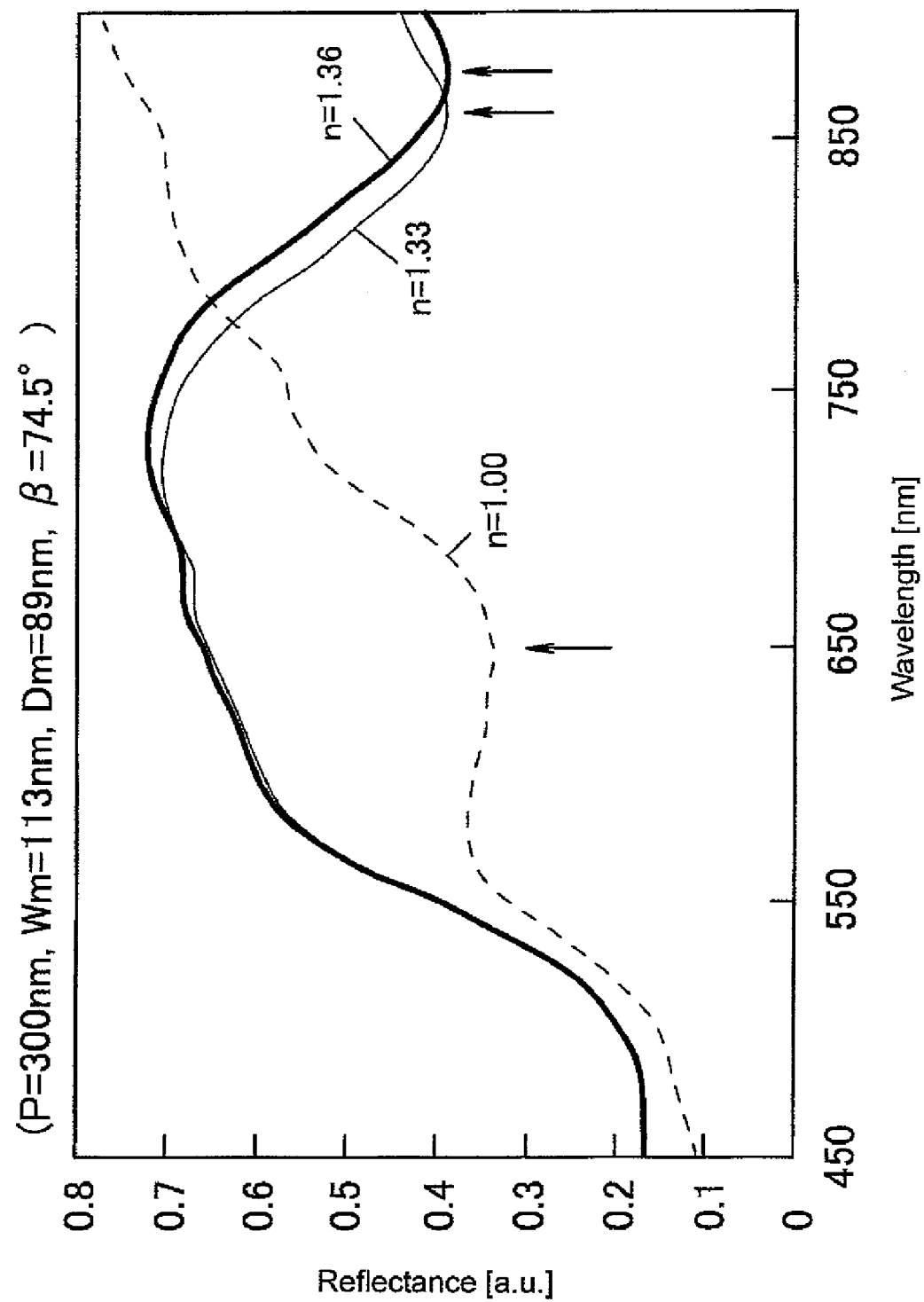
FIG. 15 shows a view of reflectance spectrum obtained by simulating a prototype of FIG. 14.

The reflectance spectrum of when the light of linear polarization was perpendicularly entered so that the polarizing surface became orthogonal to the longitudinal direction of the concave part 57 based on the simulation model same as the prototype was analyzed through the RCWA (Rigorous Coupled Wave Analysis) method. FIG. 15 shows the result of the simulation. The reflectance becomes a minimum at a wavelength of 648.8 nm in the test sample solution having an index of refraction of $n=1.00$, the reflectance becomes a minimum at a wavelength of 859.4 nm in the test sample solution having an index of refraction of $n=1.33$, and the reflectance becomes a minimum at a wavelength of 875.1 nm in the test sample solution having an index of refraction of n=1.36. The lowering in reflectance from the wavelength of the ultraviolet light to around 550 nm in the reflectance spectrum shown in FIG. 15 is caused by inter-band transition of the Au (same in FIG. 16).

The resonance wavelength was shifted by 15.7 nm between cases where the index of refraction of the test sample solution was n=1.33 and n=1.36, and thus when sensitivity was calculated therefrom, the sensor sensitivity became, 15.7/(1.36−1.33)=522.3 nm/RIU.

This is a value of about five times the sensitivity (about 100 nm/RIU) of the conventional local surface plasmon resonance sensor using Au fine particles. This result indicates a possibility of a very highly sensitive sensing, and is assumed to be because a strong resonance occurs between the metal side wall faces facing each other in the concave part 57.

The reflectance spectrum was then measured using the prototype of the sensor chip 39 that was actually manufactured. The prototype was manufactured through a manufacturing method to be hereinafter described (FIG. 29). The measurement was performed using the local SPR sensor 31 as shown in FIG. 9, where three types of measurement sample solution each having an index of refraction of n=0.00 (air), n=1.33 (water), and n=1.36 (ethanol) were used.

Figure 16:
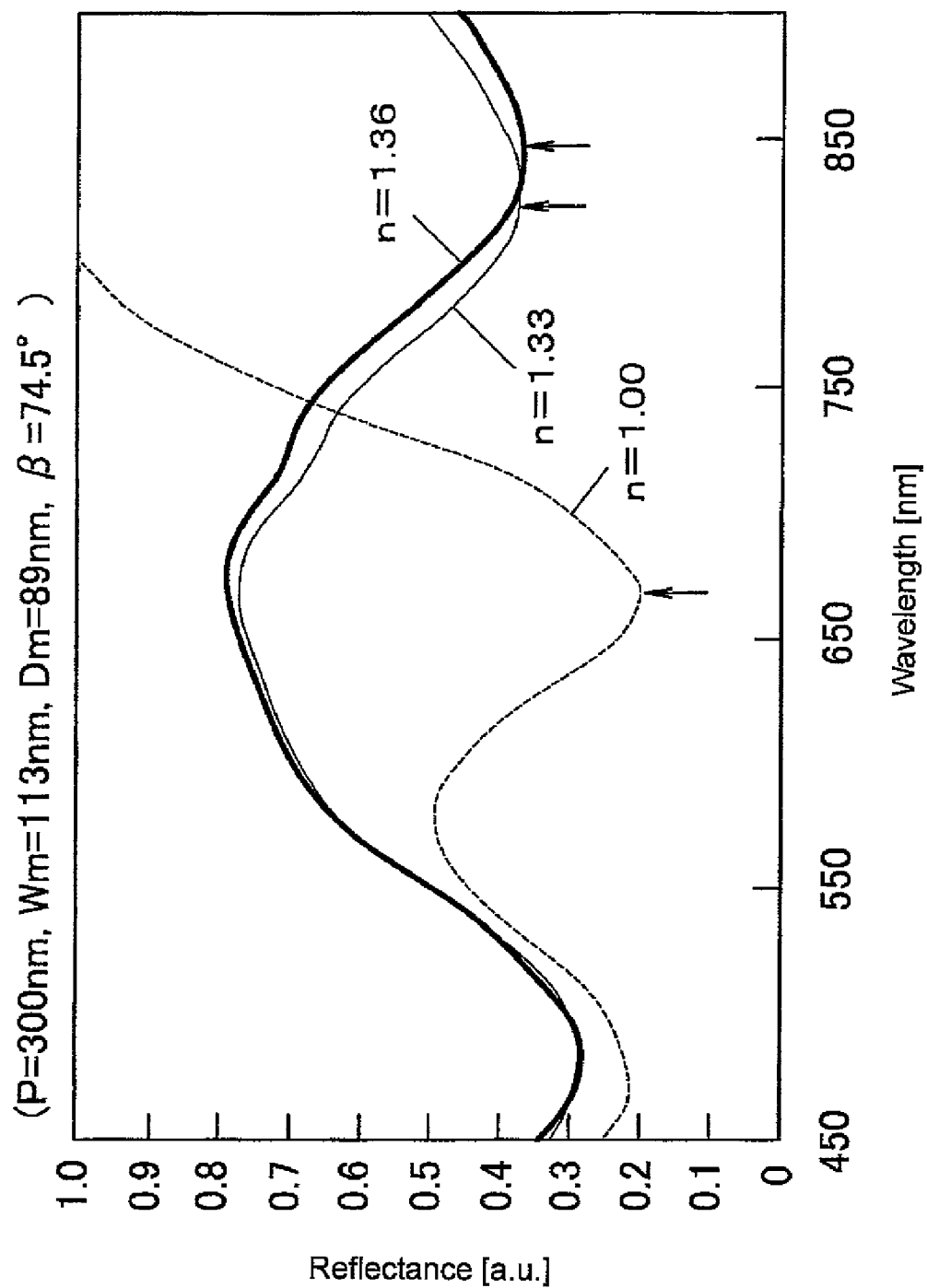
FIG. 16 shows a view of reflectance spectrum actually measured using the prototype of FIG. 14.

FIG. 16 shows a measurement result of the reflectance spectrum using the prototype. In this measurement, the reflectance became a minimum at a wavelength of 666.8 nm in the test sample solution having an index of refraction of n=1.00, the reflectance became a minimum at a wavelength of 828.0 nm in the test sample solution having an index of refraction of n=1.33, and the reflectance became a minimum at a wavelength of 844.2 nm in the test sample solution having an index of refraction of n=1.36.

The resonance wavelength was shifted by 16.2 nm between cases where the index of refraction of the test sample solution was n=1.33 and n=1.36, and thus when sensitivity was calculated therefrom, the sensor sensitivity became, 16.2/(1.36−1.33)=540 nm/RIU.

The reflectance spectrum and the sensor sensitivity of FIG. 16 for the case of prototype and the reflectance spectrum and the sensor sensitivity of FIG. 15 for the case of simulation greatly match, and the sensor sensitivity (540 nm/RIU) was recognized to have a very high sensitivity compared to the conventional local surface plasmon resonance sensor. The validity of the simulation is also supported from such measurement result.

Figure 17:
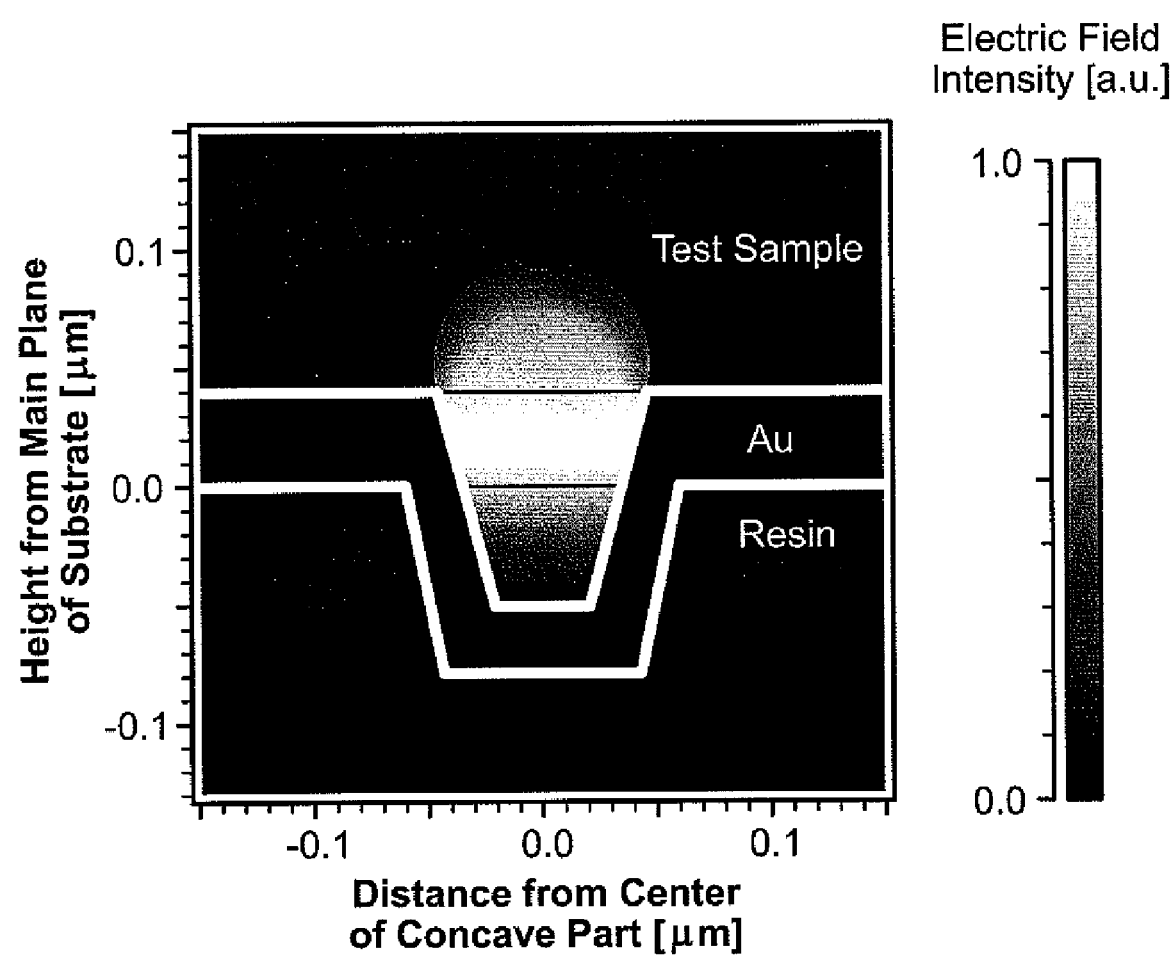
FIG. 17 shows a view of the result of simulating the electric field distribution in the concave part and the vicinity thereof.

FIG. 17 shows a view of the result of simulating the electric field distribution in the concave part 57. The electric field distribution was obtained through detailed calculation with FDTD (Finite Difference Time Domain) with the index of refraction of the test sample solution as 1.33 and the wavelength of the incident light as 859.4 nm. The model used is a simplified type for a matter of convenience of calculator memory, and the incident electric field intensity is 0.05. It was found that according to FIG. 17, since the electric field intensity exceeded 1.0 at between the side wall faces inside the concave part 57, the electric field intensity was enhanced to greater than or equal to 20 times, and a local SPR in which a very large region of the electric field intensity was concentrated at a space of smaller than or equal to a few dozen nm was generated. It is noted that the electric field intensity described herein and the electric field intensity shown in FIG. 17 are in arbitrary units, and have the incident electric field intensity as a reference value 0.05.

However, the concave part 57 cannot be of any shape of size to cause the local SPR in the concave part 57 of the metal layer 52. When assumed to be actually used as a biosensor, various restrictions are imposed in terms of property of the light source, light absorption characteristics of object to be measured, detection system, and the like. Thus, even if the concave structure is simply arranged on the surface of the metal layers it cannot be used as it is as a local surface plasmon resonance sensor. Not many cases have been proposed where analysis is performed on the local SPR generated inside the metal concave structure. Since there is no case where it is used in a sensor, it is not known what kind of concave structure can be used as the sensor to obtain a high sensitivity sensor.

In the reports that have been made, the characteristics (resonance wavelength, sharpness of the peak, sensitivity, and the like) of the local SPR are known to change by shape, size, material, and the like of the metal fine particles. In the concave structure of the present invention as well, the correlation between the shape, size, and the like and the resonance characteristic needs to be understood to consider application to the actual sensor.

The relationship between the width Wm, the depth Dm, and the inclination angle β of the side wall faces of the concave part 57 and the resonance wavelength was examined from such standpoints. Analysis was performed using Au for the type of metal layer 52 used herein, which caused local SPR in the visible light region, which was chemically stable, and which was a most common material as a local surface plasmon resonance sensor.

Figure 18:
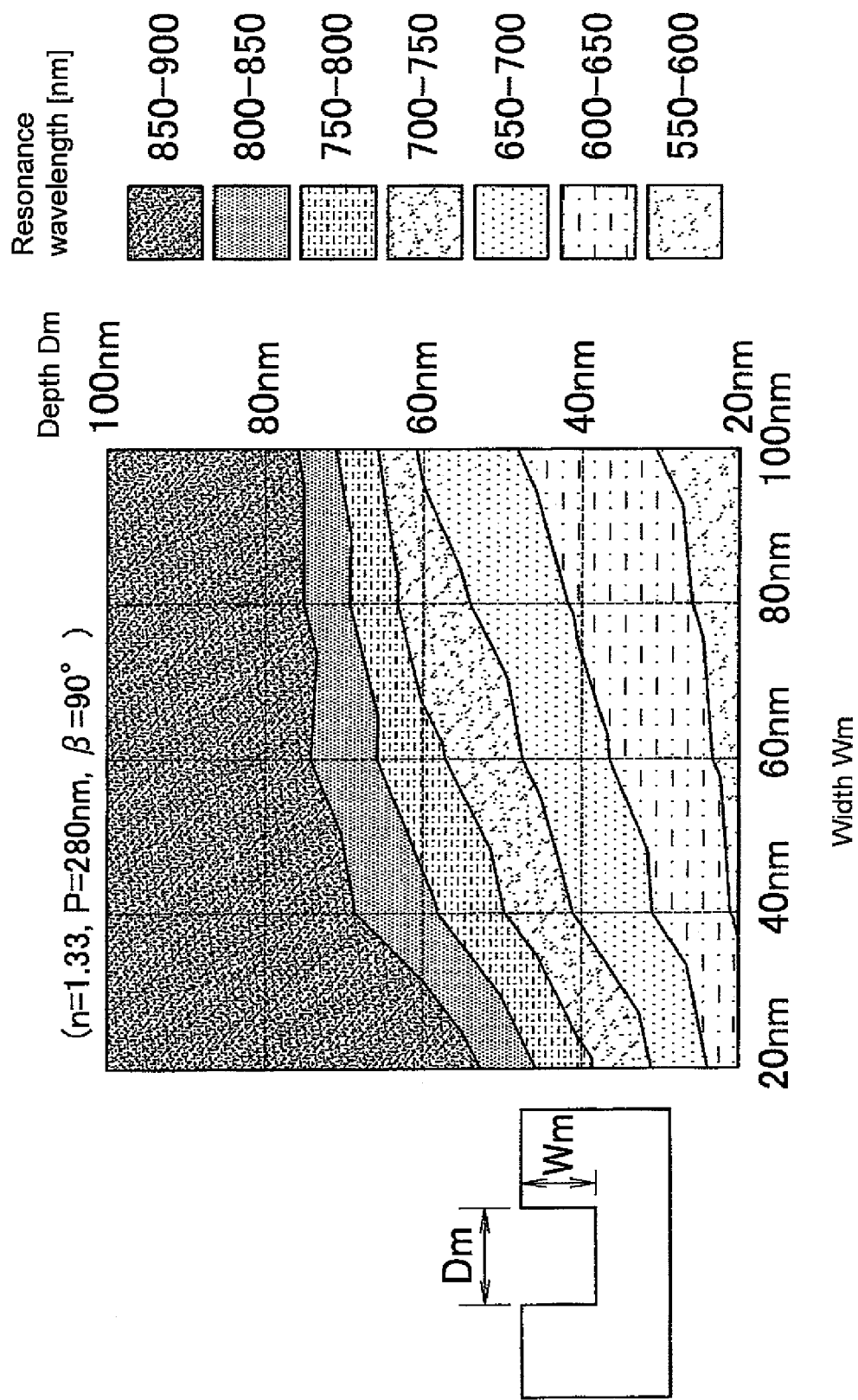
FIG. 18 shows a view of change in resonance wavelength of when the width Wm and the depth Dm of the concave part are changed.

First, the change in resonance wavelength in a case where the width and the depth of the concave part 57 were changed was examined. FIG. 18 shows a view of change in resonance wavelength when the width Wm and the depth Dm of the concave part 57 are respectively changed from 20 nm to 100 nm. The resonance wavelength is expressed by regions sectionalized every 50 nm. This is the result of analysis by simulation through the RCWA with the inclination angle of the side wall face of the concave part 57 as β=90 degrees, the pitch as P=280 nm, and the index of refraction of the test sample solution as n=1.33.

Figure 19:
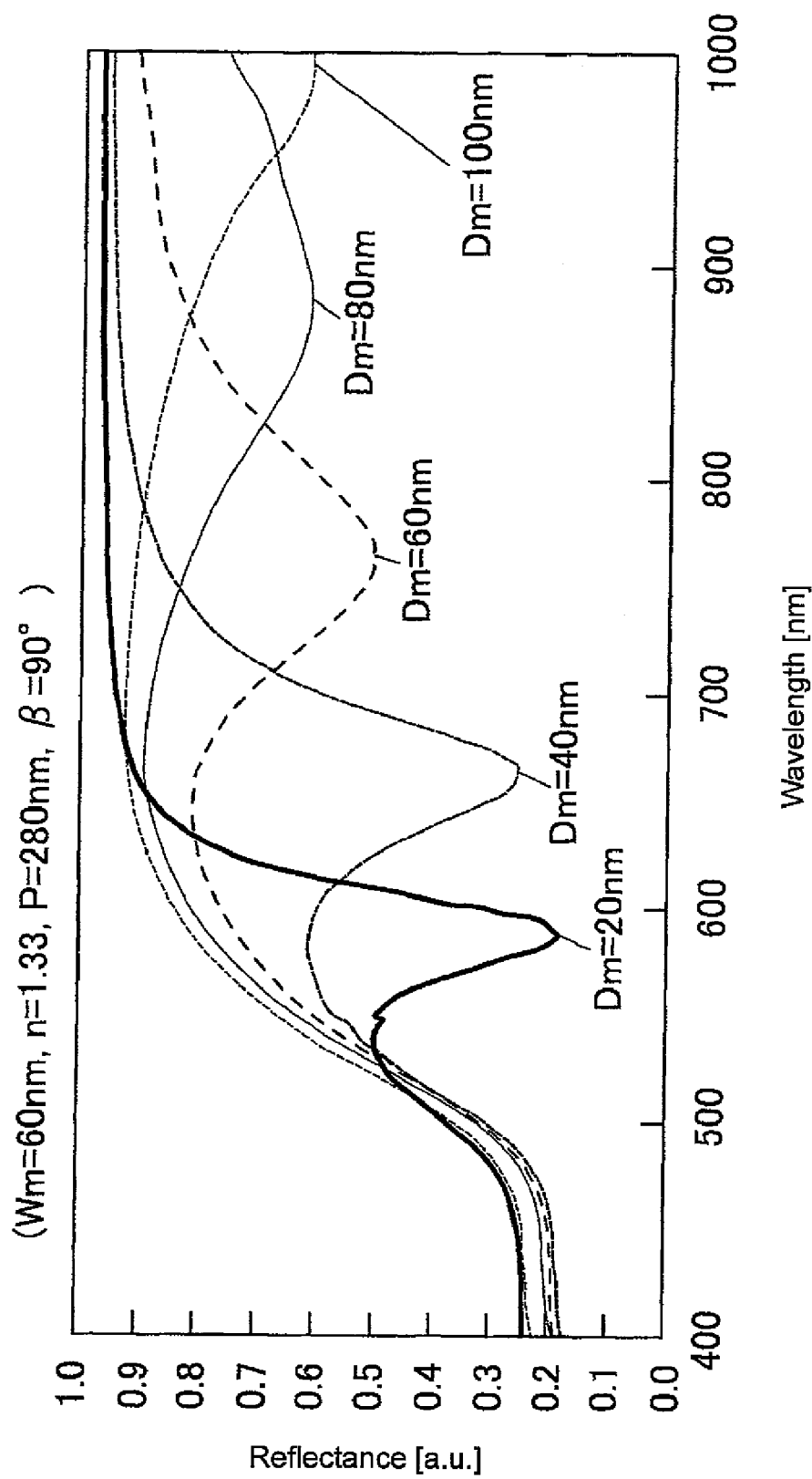
FIG. 19 shows a view of the reflectance spectrum of when the width of the concave part is fixed at 60 nm, and the depth Dm is changed.

FIG. 19 shows a view of the reflectance spectrum of when the width of the concave part 57 is fixed, and the depth Dm is changed to 20 nm, 40 nm, 60 nm, 80 nm, and 100 nm.

As apparent from FIGS. 18 and 19, the resonance wavelength has correlation particular with the depth Dm of the concave part 57, where the resonance wavelength shifts towards the long wavelength side at a large rate of change as the depth Dm becomes deeper. It is considered that since the depth of the concave part 57 becomes larger, the influence of the multipolar mode occurs, and the shift towards the long wavelength side occurs. The resonance wavelength also has correlation with the width Wm of the concave part 57, although not as much as with the depth Dm, where the resonance wavelength shifts towards the long wavelength side as the width Wm becomes narrower.

When used as a biosensor, the resonance absorption must occur at the region from the visible light to the near-infrared light to eliminate the influence of absorption spectrum of the water. When the depth Dm of the concave part 57 becomes greater than or equal to 100 nm, the resonance absorption occurs at a wavelength of greater than or equal to 1000 nm at which absorption by water is strong, and thus the depth Dm of the concave part 57 must be smaller than or equal to 100 nm to generate resonance in the region from the visible light to the near-infrared light.

Figure 20:
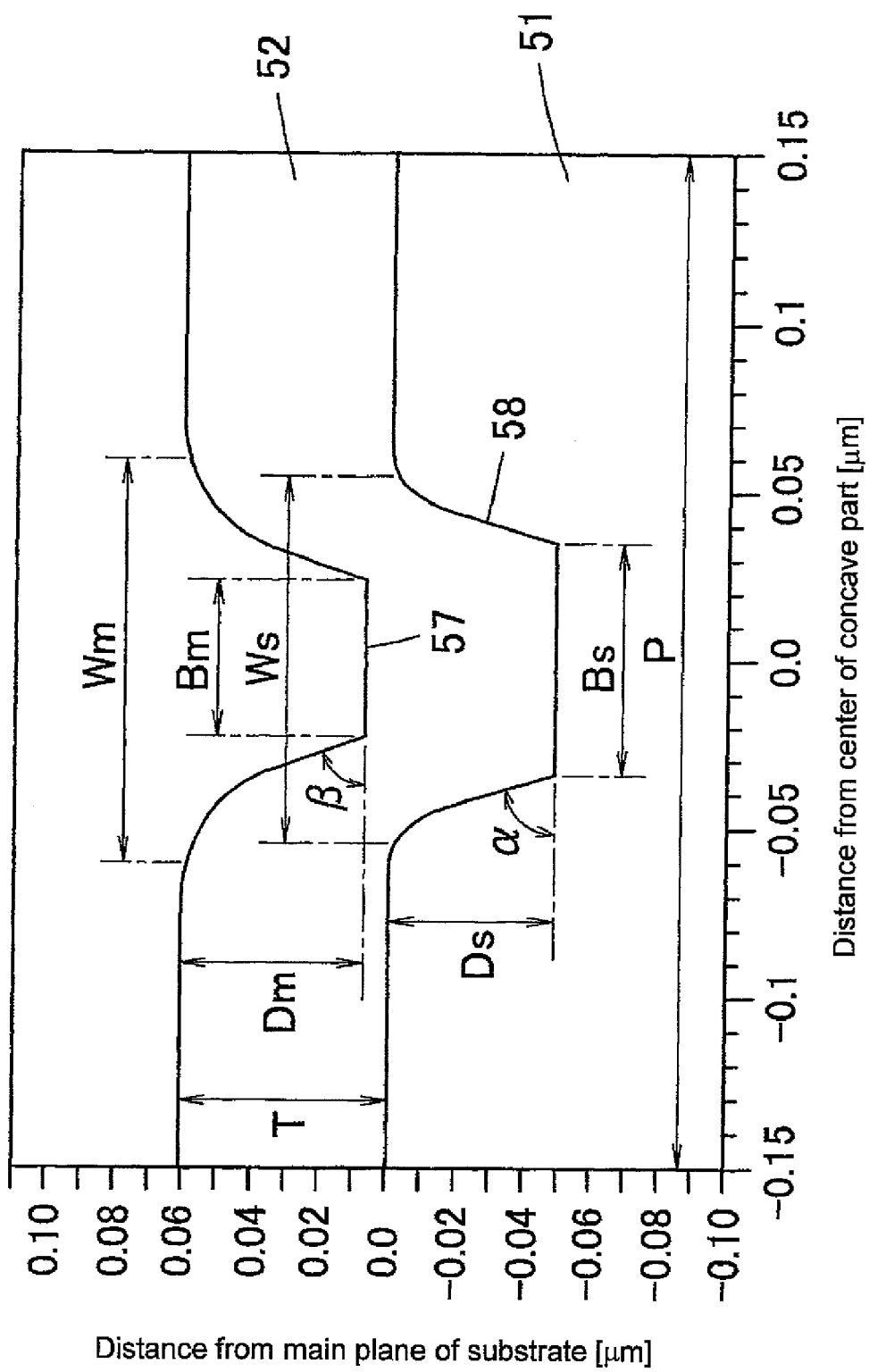
FIG. 20 shows a view of a cross sectional shape of one concave part in a prototype of the first embodiment having different depth.

Subsequently, a prototype in which the depth Dm of the concave part 57 was actually changed was experimentally formed, and the correlation with the depth Dm was examined. FIG. 20 shows a view of the cross sectional shape of the concave part 57 of a prototype in which the depth is changed. In this prototype, the depression 58 formed in the substrate 51 made of resin has a width at the bottom surface of Bs=70 nm, a width of an opening of Ws=121 nm, a depth of Ds=47 nm, and an inclination angle of the side wall face of α=73 degrees. The metal layer 52 (Au thin-film) having a film thickness of T=60 nm is deposited on the surface of the substrate 51, where the concave part 57 formed in the depression 58 by the metal layer 52 has a width at the bottom surface of Bm=47 nm, a width of an opening of Wm=138 nm, a depth of Dm=54 nm, and an inclination angle of the side wall face of β=70 degrees. The depression 58 and the concave part 57 are arrayed in parallel at a constant pitch of P=300 nm. Furthermore, the index of refraction of the substrate 51 is 1.49, where the test sample solution contacting the metal layer 52 has an index of refraction of n=1.00, n=1.33, or n=1.36. In the prototype of FIG. 20, the depth of the concave part 57 is shallow or Dm=54 nm, as opposed to the depth Dm of the concave part 57 of Dm=89 nm in the prototype of FIG. 14.

Figure 21:
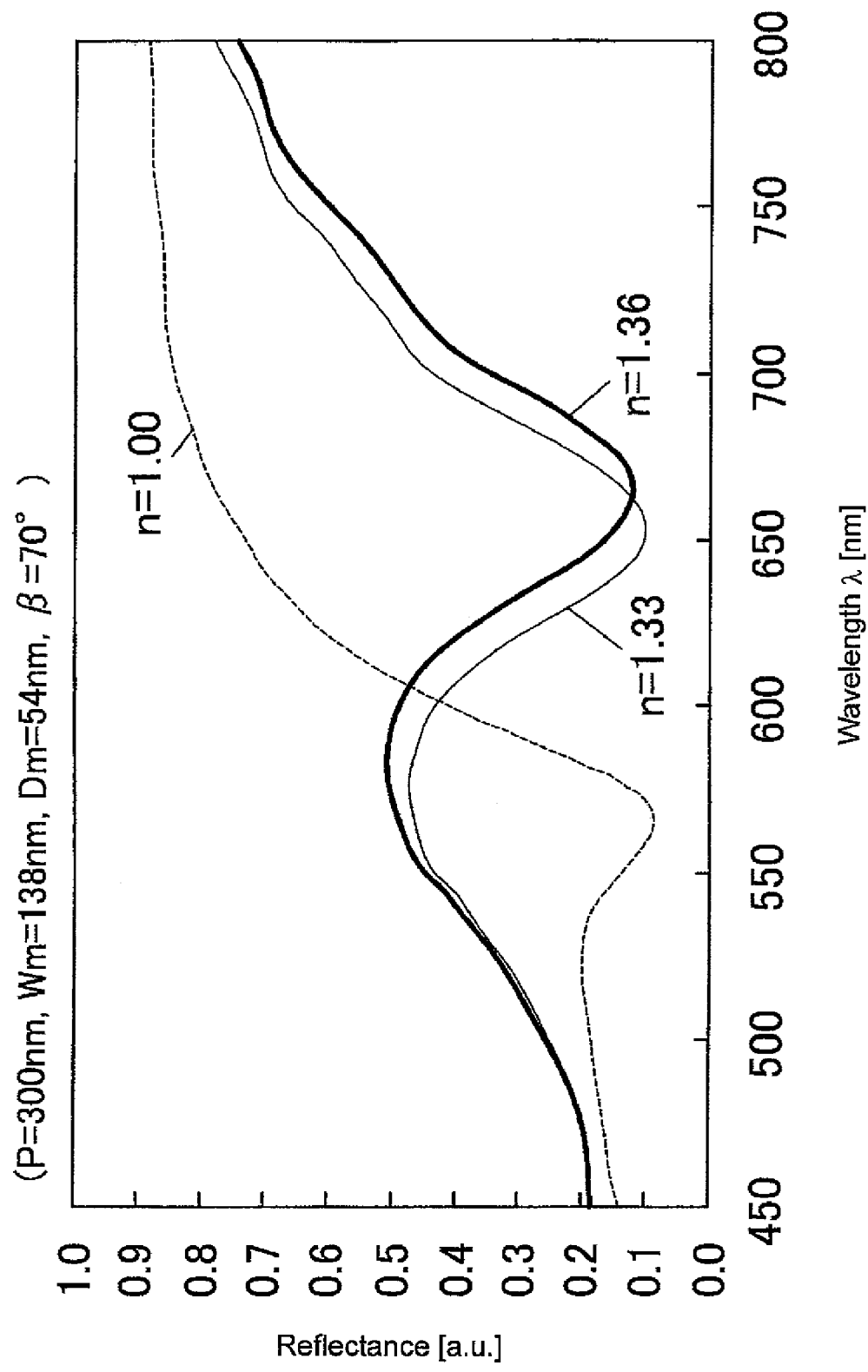
FIG. 21 shows a view of reflectance spectrum obtained by simulating a prototype of FIG. 20.
Figure 22:
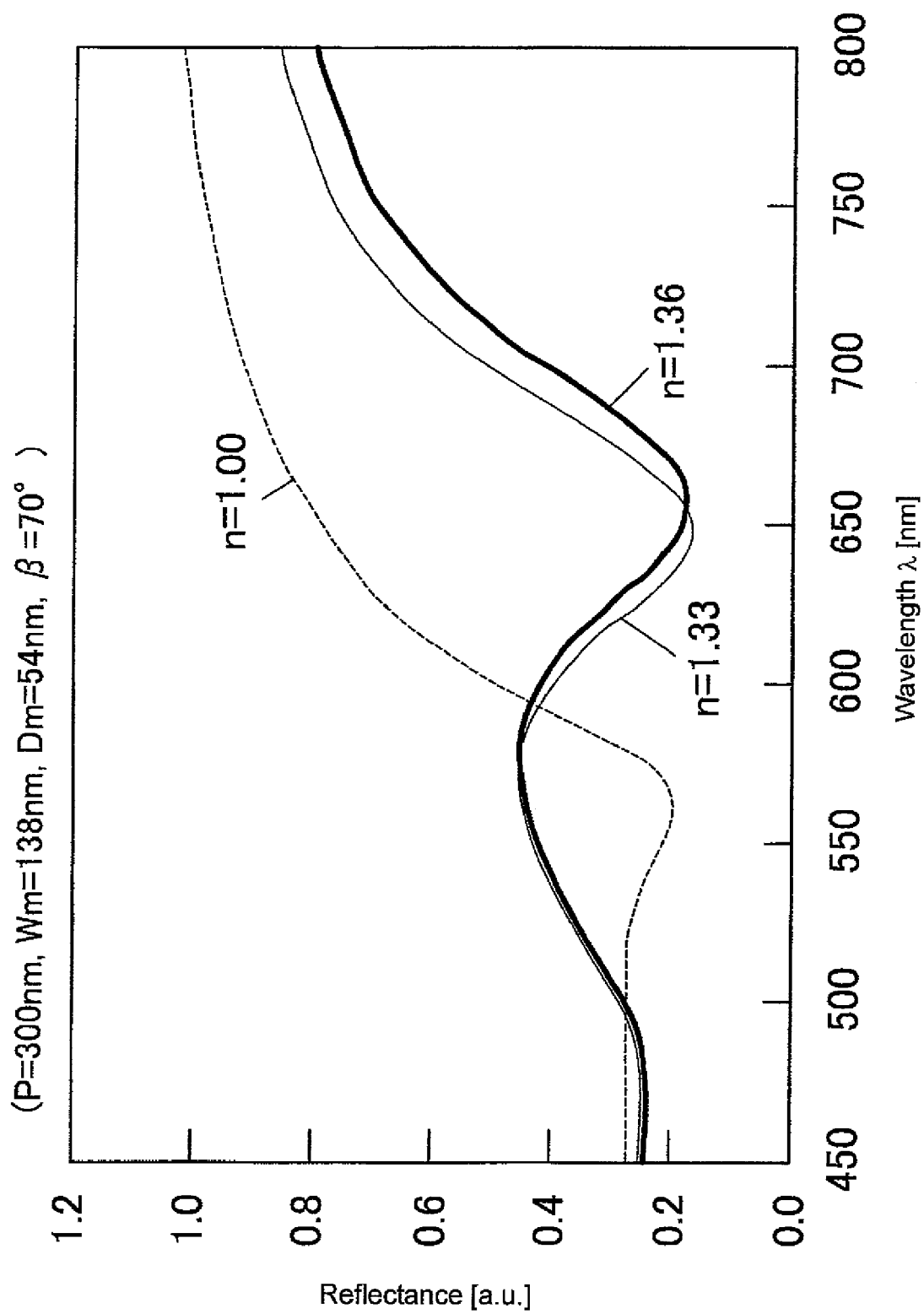
FIG. 22 shows a view of reflectance spectrum actually measured using the prototype of FIG. 20.

FIG. 21 shows a view of the result of obtaining the reflectance spectrum through simulation (RCWA method) using the model same as the prototype of FIG. 20. FIG. 22 shows a view of the result of when the reflectance spectrum is actually measured using the prototype of FIG. 20. The prototype is manufactured through a manufacturing method to be hereinafter described (FIG. 29). The measurement was performed using the local SPR sensor 31 as shown in FIG. 9, where three types of measurement sample solution each having an index of refraction of n=1.00 (air), n=1.33 (water), and n=1.36 (ethanol) were used.

According to the simulation result of FIG. 21, the resonance wavelength is 561.5 nm when the index of refraction of the test sample solution is n=1.00, the resonance wavelength is 653.2 nm when the index of refraction of the test sample solution is n=1.33, and the resonance wavelength is 665.1 nm when the index of refraction of the test sample solution is n=1.36. According to the actual measurement result of FIG. 22, the resonance wavelength is 557.5 nm when the index of refraction of the test sample solution is n=1.00, the resonance wavelength is 647.6 nm when the index of refraction of the test sample solution is n=1.33, and the resonance wavelength is 656.2 nm when the index of refraction of the test sample solution is n=1.36. A satisfactory match between the simulation result and the actual measurement result was recognized.

Comparing FIG. 15, which is the simulation result using the model of the prototype of FIG. 14, and FIG. 21, which is the simulation result using the model of the prototype of FIG. 20, it is found that the resonance wavelength changes to the short wavelength side as the depth Dm of the concave part 57 becomes shallow. Similarly, comparing FIG. 16, which is the actual measurement result using the model of the prototype of FIG. 14, and FIG. 22, which is the actual measurement result using the model of the prototype of FIG. 20, it is found that the resonance wavelength changes to the short wavelength side as the depth Dm of the concave part 57 becomes shallow. For instance, comparing the cases where the index of refraction of the test sample solution is 1.33 in the actual measurement result of FIG. 16 and FIG. 22, the resonance wavelength greatly changes to the short wavelength side from 828.0 nm to 647.6 nm as the depth of the concave part 57 becomes shallow from 89 nm to 54 nm.

Figure 23:
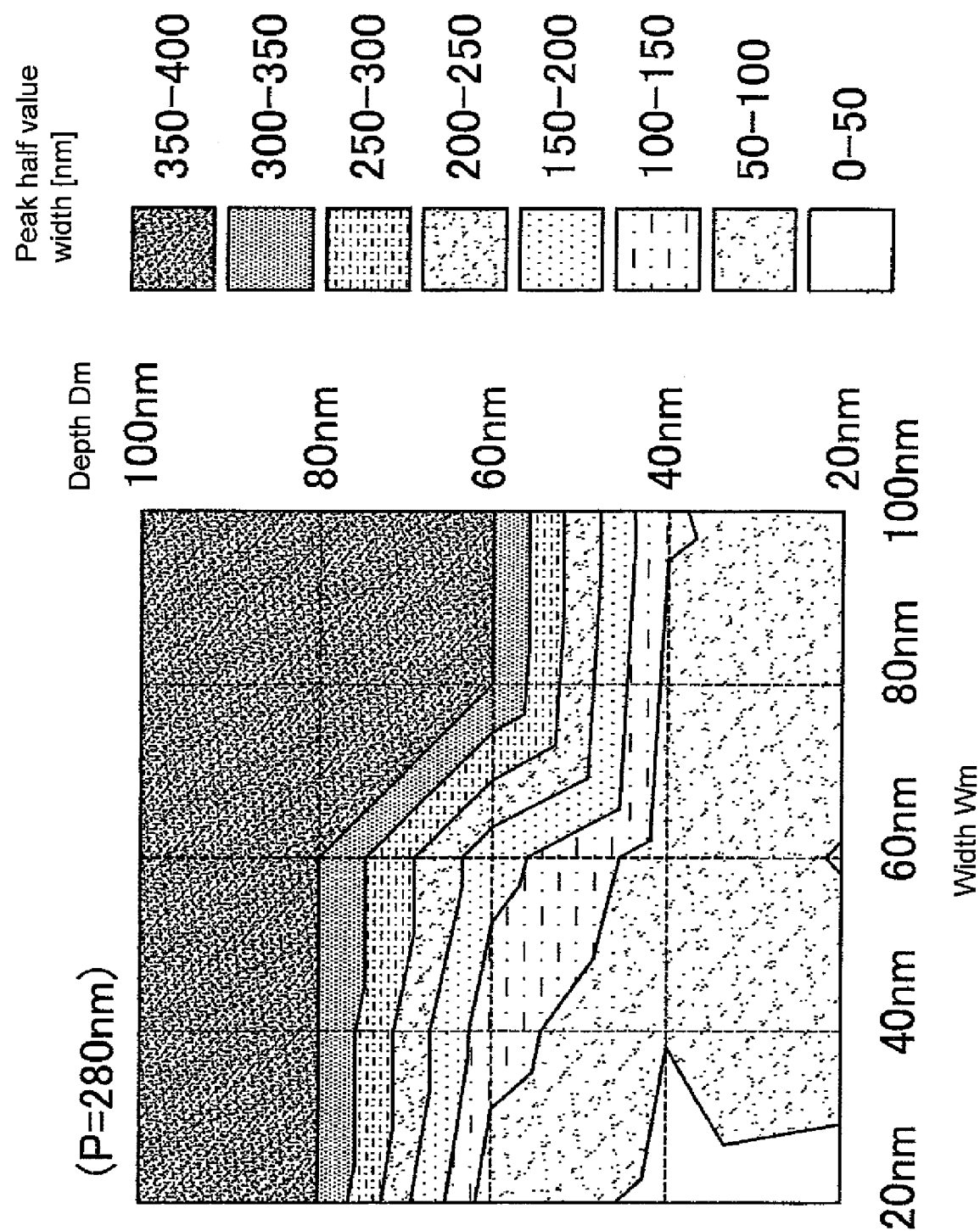
FIG. 23 shows a view of change in a peak half value width of when the width Wm and the depth Dm of the concave part are changed.
Figure 24:
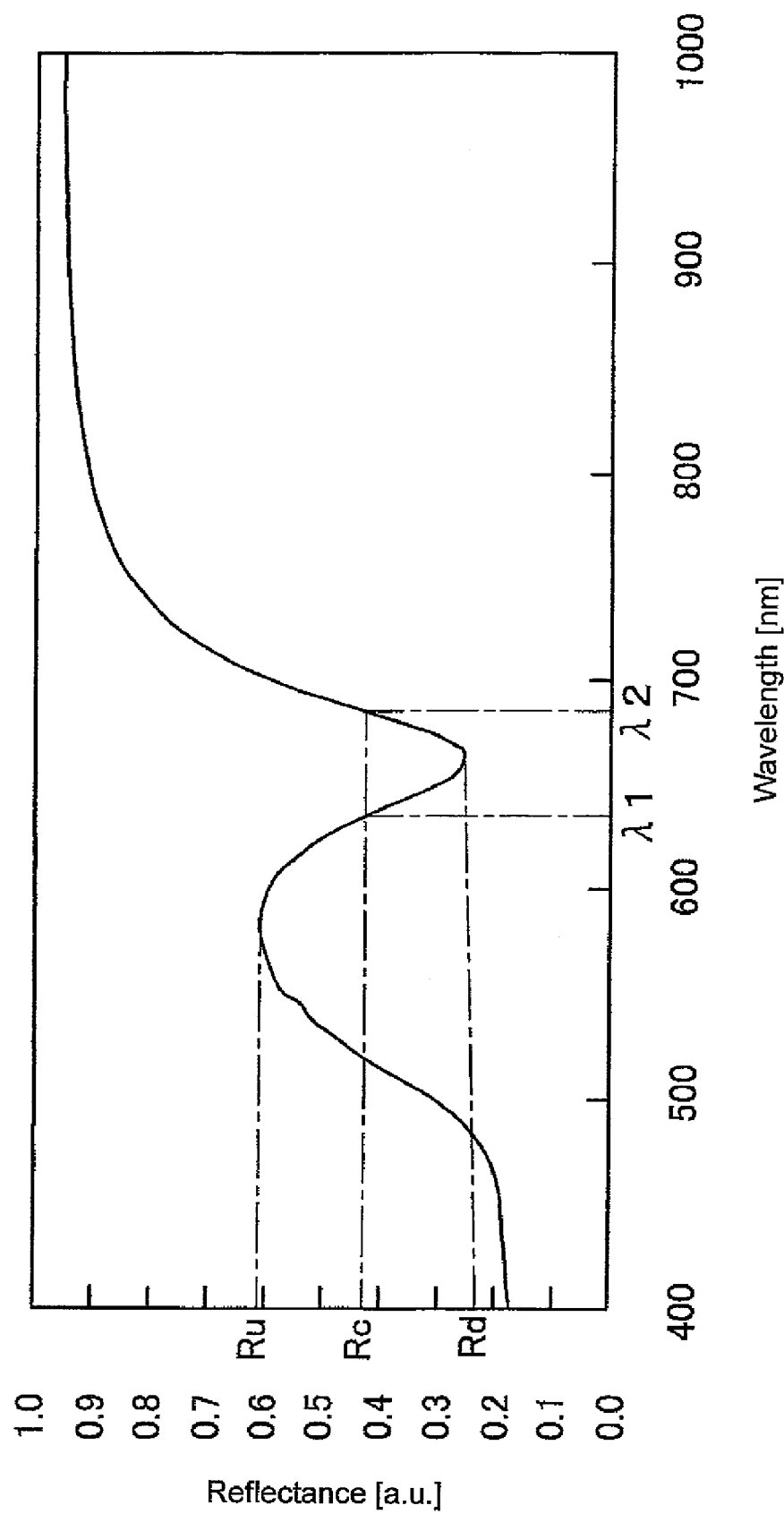
FIG. 24 shows a view describing the definition of the peak half value width.

Subsequently, the relationship between the width Wm and the depth Dm of the concave part 57 and the half value width of the peak was examined. FIG. 23 shows the result. FIG. 23 shows the result of analyzing the magnitude of the peak half value width of when the width Wm and the depth Dm of the concave part 57 are changed through simulation. The peak half value width at the minimum value is defined as below. As shown in FIG. 24, the reflectance at the minimum point is Rd, the reflectance at the maximum point positioned on the short wavelength side from the minimum point is Ru, and the wavelengths of the points at where the reflectance equal to the average value Rc=(Ru+Rd)/2 is obtained on both sides of the minimum point is $\lambda 1$, $\lambda 2$ (where, $\lambda 1 < \lambda 2$).

The amount defined by $$\lambda 2 - \lambda 1 / \{(Ru-Rd)/2\}$$

is referred to as peak half value width. Since the peak at the minimum value becomes sharper the smaller the peak half value width, the detection of the resonance point can be performed at high accuracy.

According to FIG. 23, the peak half value width is recognized to significantly widen the deeper the depth Dm of the concave part 57. This is assumed to be because as the depth of the concave part 57 becomes deeper, the isolation from quasi electrostatic model becomes larger, and the influence of shift in the phase of the incident light in the concave part 57 cannot be ignored, whereby the peak half value width widens. Regarding the width Wm of the concave part 57, the peak half value width becomes narrower the narrower the width Wm.

Figure 25:
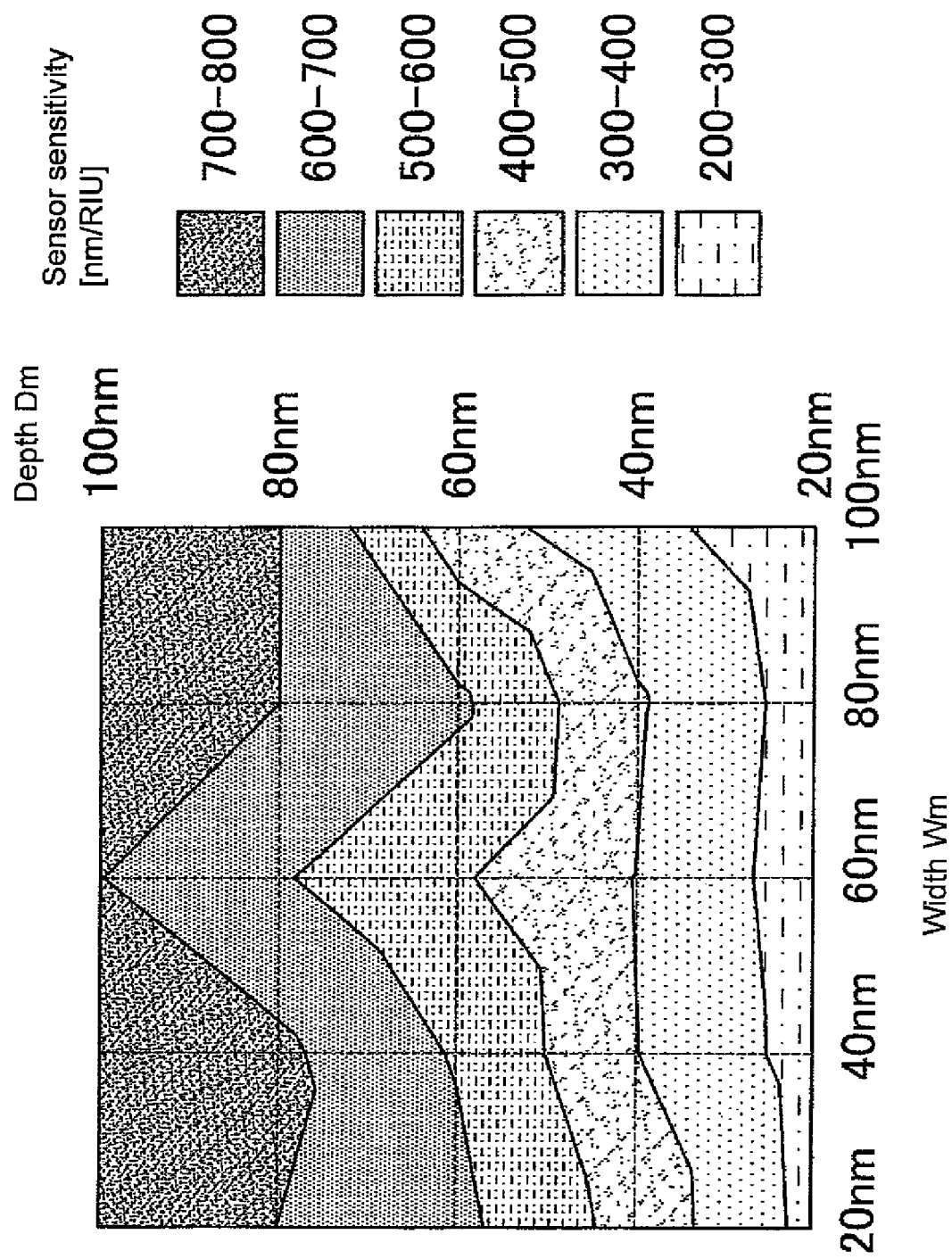
FIG. 25 shows a view of change in sensor sensitivity of when the width Wm and the depth Dm of the concave part are changed.

The relationship between the width Wm and the depth Dm of the concave part and the sensitivity was then examined. FIG. 25 shows a view of the result of analyzing the magnitude of the sensor sensitivity of when the width Wm and the depth Dm of the concave part 57 are changed through simulation.

Accordingly to FIG. 25, the sensor sensitivity significantly lowers the shallower the depth Dm of the concave part 57. Since the region of the resonance electric field generated by surface plasmon becomes small when the depth Dm of the concave part 57 is shallow, the energy of the incident light cannot be effectively used, and sensitivity lowers. When the width Wm of the concave part 57 becomes narrow, the region of the resonance electric field becomes narrow, but the opposing side wall faces of the metal layer 52 approach by the relevant amount and the enhancement of the electric field becomes larger. Thus, the influence of the width Wm of the concave part 57 on the sensitivity is not as significant as the depth Dm.

Considering the results described above, the depth Dm of the concave part 57 needs to be smaller than or equal to 100 nm. However, in terms of sensitivity, the sensitivity significantly lowers the shallower the depth Dm as shown in FIG. 25. Thus, the depth Dm of the concave part 57 is realistically about 20 to 100 nm to be effective for the sensor.

The width Wm of the concave part 57 is desirably smaller than or equal to 100 nm at an intermediate point of the depth Dm considering the sharpness of the peak at the resonance point. However, when used as a biosensor, a gap of at least about 20 nm needs to be created between the side wall faces since the size of a general protein is about 10 nm taking into consideration that a probe layer of the protein, an antibody, and the like are formed on the surface. Thus, the width Wm of the concave part 57 is ideally about 20 to 100 nm as a biosensor.

Figure 26:
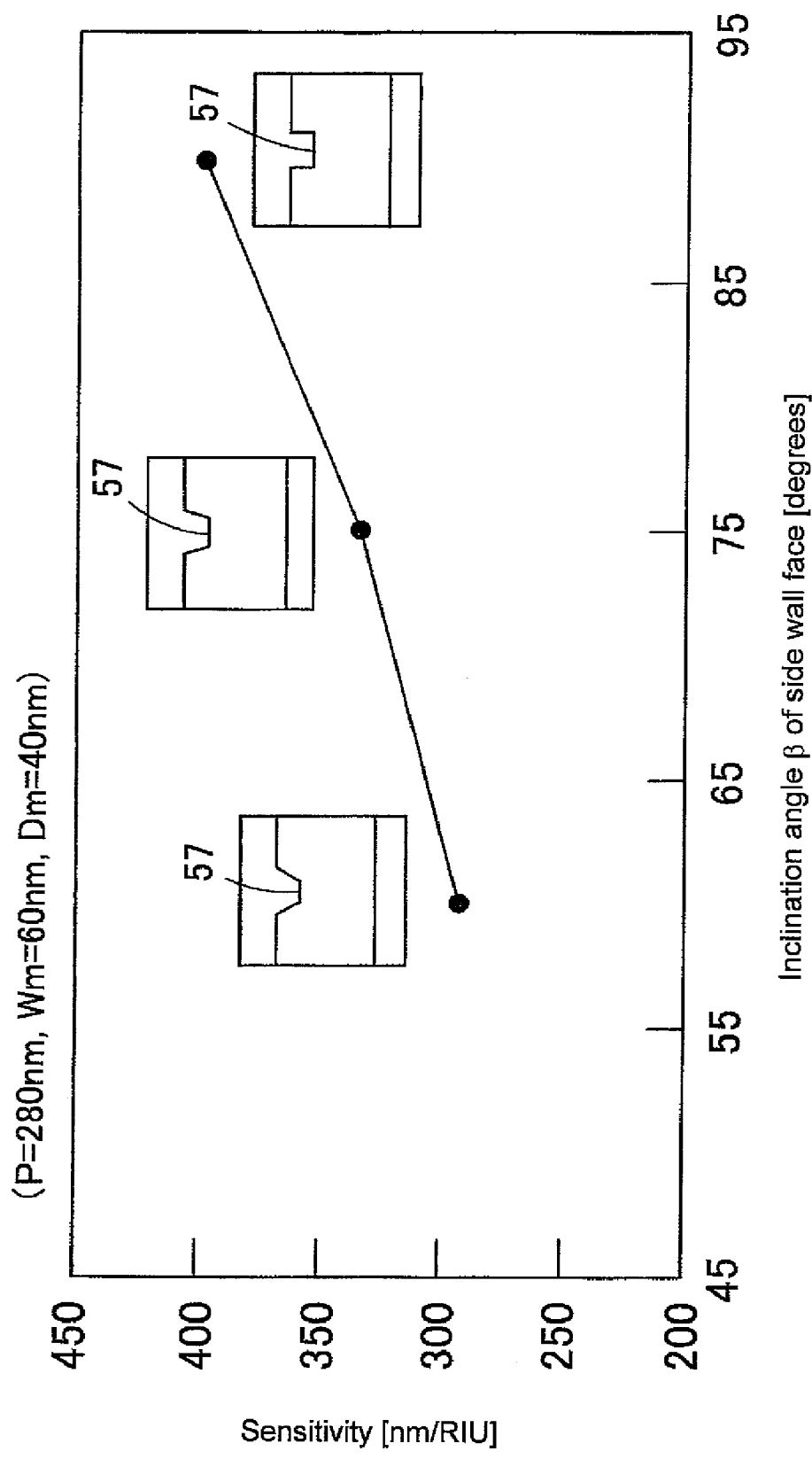
FIG. 26 shows a view of a relationship between an inclination angle of the side wall face of the concave part and the sensor sensitivity.

The correlation between the inclination angle β of the side wall face of the concave part 57 and the sensor sensitivity was then examined. To this end, the concave part 57 having a width of Wm=60 nm, a depth of Dm=40 nm, and a pitch of P=280 nm was formed, and the sensitivity was measured while changing the inclination angle β of the side wall face from 60 degrees to 90 degrees. This result is shown in FIG. 26. As apparent from the figure, the sensitivity becomes higher the closer the side wall face of the concave part 57 is to perpendicular. The reason therefore is assumed to be because if the inclination angle β of the side wall face is small, the SPR is spread towards the opening side of the concave part 57, whereby the closing effect of the electric field lowers and as a result the enhancement of the electric field lowers and the sensitivity lowers. Therefore, in order to achieve high sensitivity with the local SPR sensor 31 of the present invention, the inclination angle β of the side wall face is desirably brought as close as possible to 90 degrees.

Regarding the pitch P for arraying the concave part 57, diffraction may occur depending on the angle of the incident light if an interval of greater than or equal to 400 nm is formed, and may coexist with the resonance peak of the local SPR. In order to prevent diffraction, the pitch P is set to smaller than or equal to 400 nm. In the sensor chip 39 of the present invention, a large correlation as when the depth Dm and the width Wm are changed is not found between the pattern structure of the concave part 57 and the resonance characteristic if the pitch P is between 200 and 400 nm due to the local plasmon resonance generated inside the concave part 57.

The required region of the metal film in the concave part 57 was then examined. First, as shown in FIG. 27A, the metal layer 52 having a film thickness of 40 nm was formed on the substrate 51 having an index of refraction of 1.49, and the concave part 57 having a depth of Dm=40 nm and a width of Wm=60 nm was formed therein. The concave part 57 has only both side wall faces covered with the metal layer 52, where the metal layer 52 is not formed at the bottom surface of the concave part 57, and the substrate 51 is exposed. The reflectance spectrum was measured with the upper surface of the prototype filled with water (n=1.33) or ethanol (n=1.36), and the result shown in FIG. 27B was obtained.

Figure 28A:
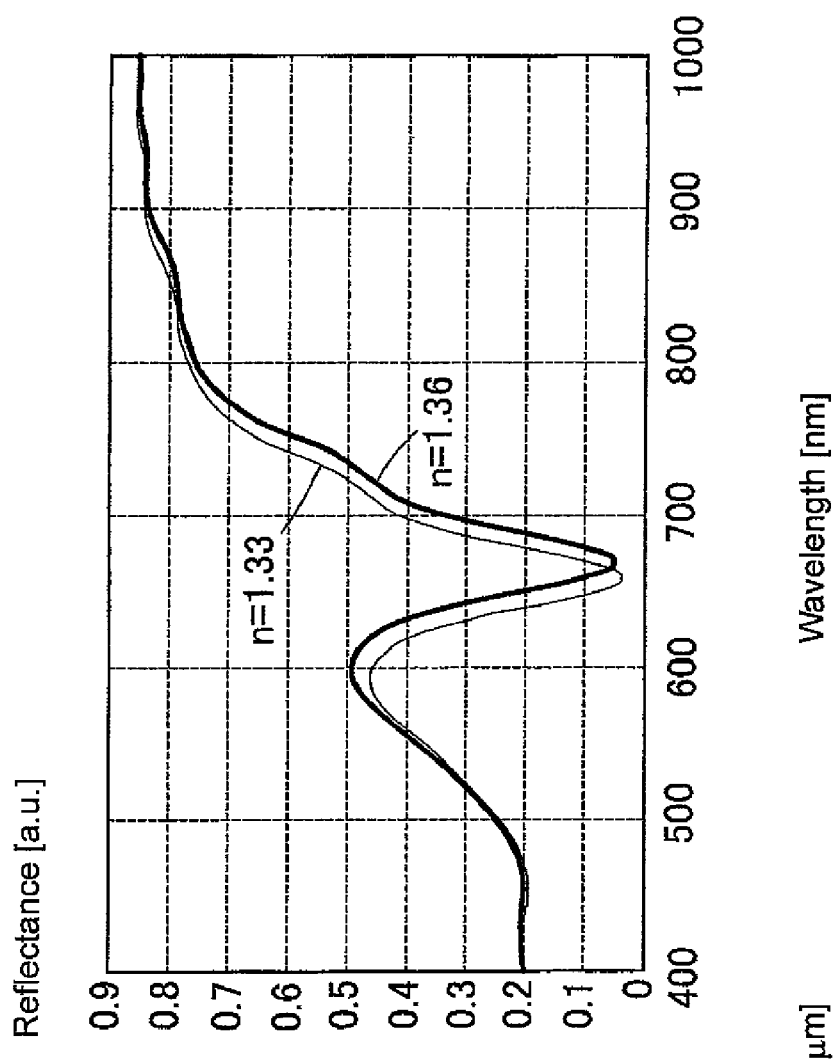
FIG. 28A shows a cross sectional view of a concave part with a metal layer at the bottom surface.

As shown in FIG. 28A, the depression 58 was formed in the surface of the substrate 51 having an index of refraction of 1.49, the metal layer 52 having a film thickness of 40 nm is formed on the substrate 51, and the concave part 57 having a depth of Dm=45 nm and a width of Wm=60 nm was formed therein. The concave part 57 has both side wall faces and the bottom surface covered with the metal layer 52. The reflectance spectrum was measured with the upper surface of the prototype filled with water (n=1.33) or ethanol (n=1.36), and the result shown in FIG. 28B was obtained.

Figure 27B:
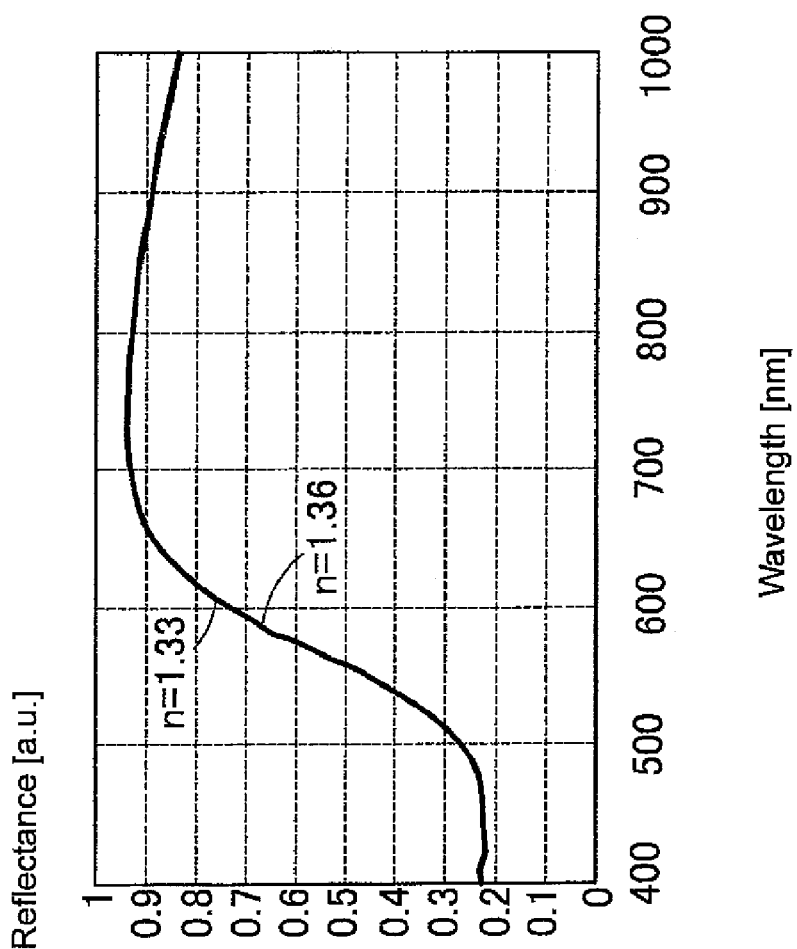
FIG. 27A shows a cross sectional view of a concave part without a metal layer at the bottom surface, and 27B shows a view of the reflectance spectrum thereof.
Figure 27A:
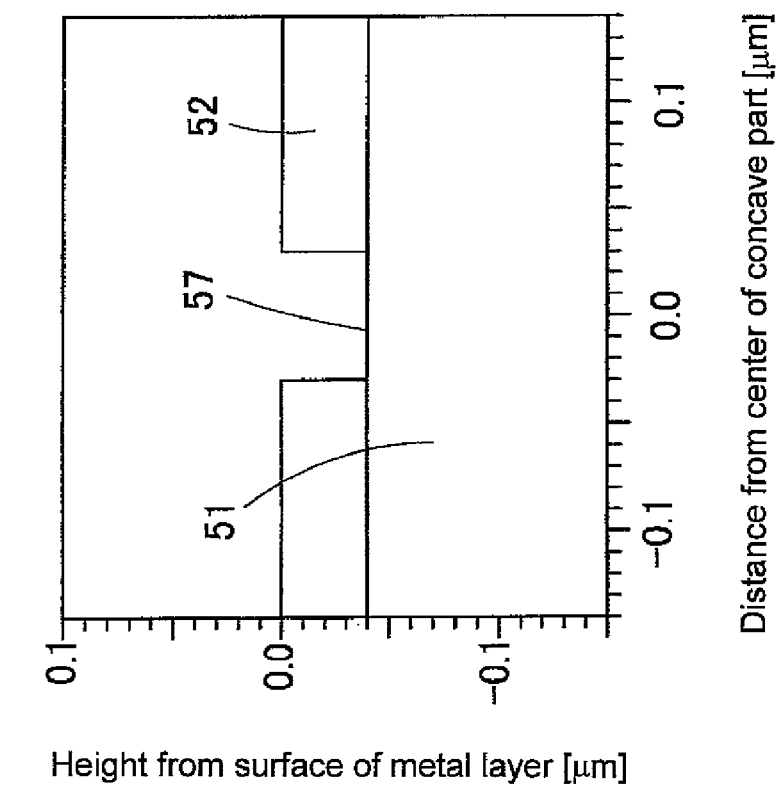
Figure 28B:
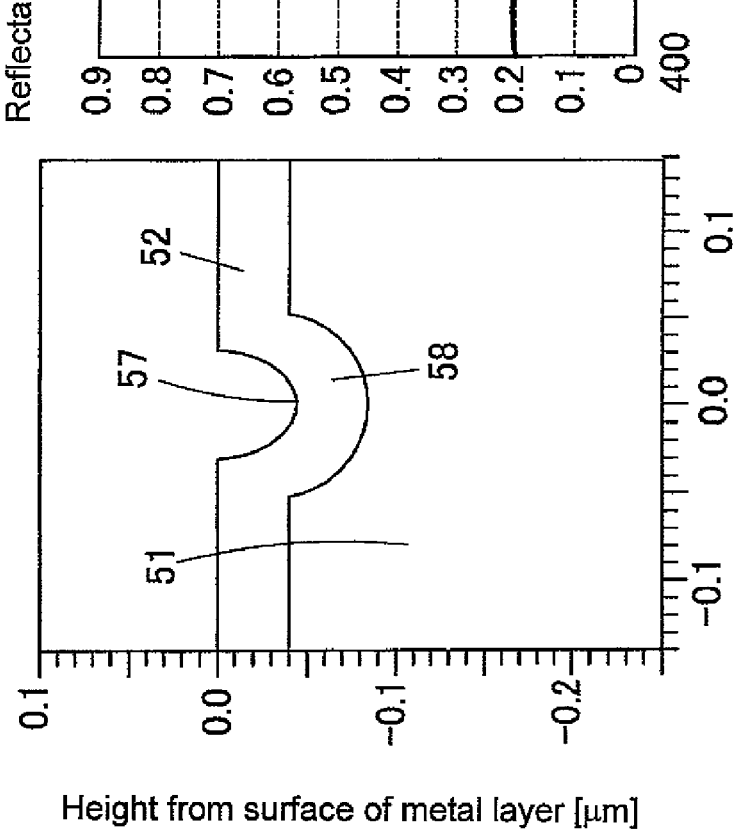
FIG. 28B shows a view of the reflectance spectrum thereof.

Comparing FIG. 27B and FIG. 28B, the minimum point by SPR is recognized when the wavelength is around 660 nm in FIG. 28B, but the minimum point by SPR is not recognized in FIG. 27B. Therefore, when the metal layer 52 is not formed on the bottom surface of the concave part 57 as in FIG. 27A, SPR does not occur, and thus the bottom surface of the concave part 57 also needs to be covered with the metal layer 52 to serve as a sensor.

Experiments and simulations have been carried out using Au for the metal layer in the present embodiment, but both Au and Ag generate SPR in the visible light region, and the resonance wavelengths differ only by about 100 nm, and thus the shape and the size of the concave part 57 are also applicable to Ag.

(Manufacturing Method)

The manufacturing steps of the sensor chip 39 according to the present embodiment will be described with reference to FIG. 29. First, a photoresist 60 is applied on an Si substrate 59 through spin coating, and the like. A concave pattern 61 of the same shape as the depression of the substrate is formed in the photoresist 60 using a semiconductor manufacturing process, thereby manufacturing a master including a great number of concave patterns as shown in FIG. 29A. In this case, X-ray lithography, electron lithography, DRIE (Deep Reactive Ion Etching), and the like are used for the semiconductor manufacturing process. A die 62 (stamper) is manufactured on the master by applying electroforming technique. That is, as shown in FIG. 29B, Ni is deposited on the master to manufacture the die 62. An inverted shape 63 of the master is formed at the lower surface of the die 62 stripped from the master, as shown in FIG. 29C.

A depression is then formed on a resin using nanoimprinting technique. That is, as shown in FIG. 29D, PMMA (polymethylmethacrylate), which is a thermoplastic resin, is applied on a glass substrate 64, the PMMA is pressed down with the die 62 while being heated to higher than or equal to 120° C. and then returned to normal temperature in such state to cure the PMMA. The resin to be used may be ultraviolet curable. Consequently, a concave pattern same as the master is transferred to the surface of the substrate 51 molded by the PMMA, as shown in FIG. 29E, thereby molding a depression 58 in the surface of the substrate 51. The advantage of using nanoimprinting as a method of molding the depression 58 in the substrate 51 is that great amount of duplicate copies can be obtained by manufacturing one die 62 and thus mass productivity is very high, and that a pattern same as the master is obtained at high accuracy and satisfactory reproducibility. If the master used has high resistance property, a new die 62 can be manufactured from the master when the die 62 wears.

Figures 29A, 29B, 29C, 29D, 29E, 29F:
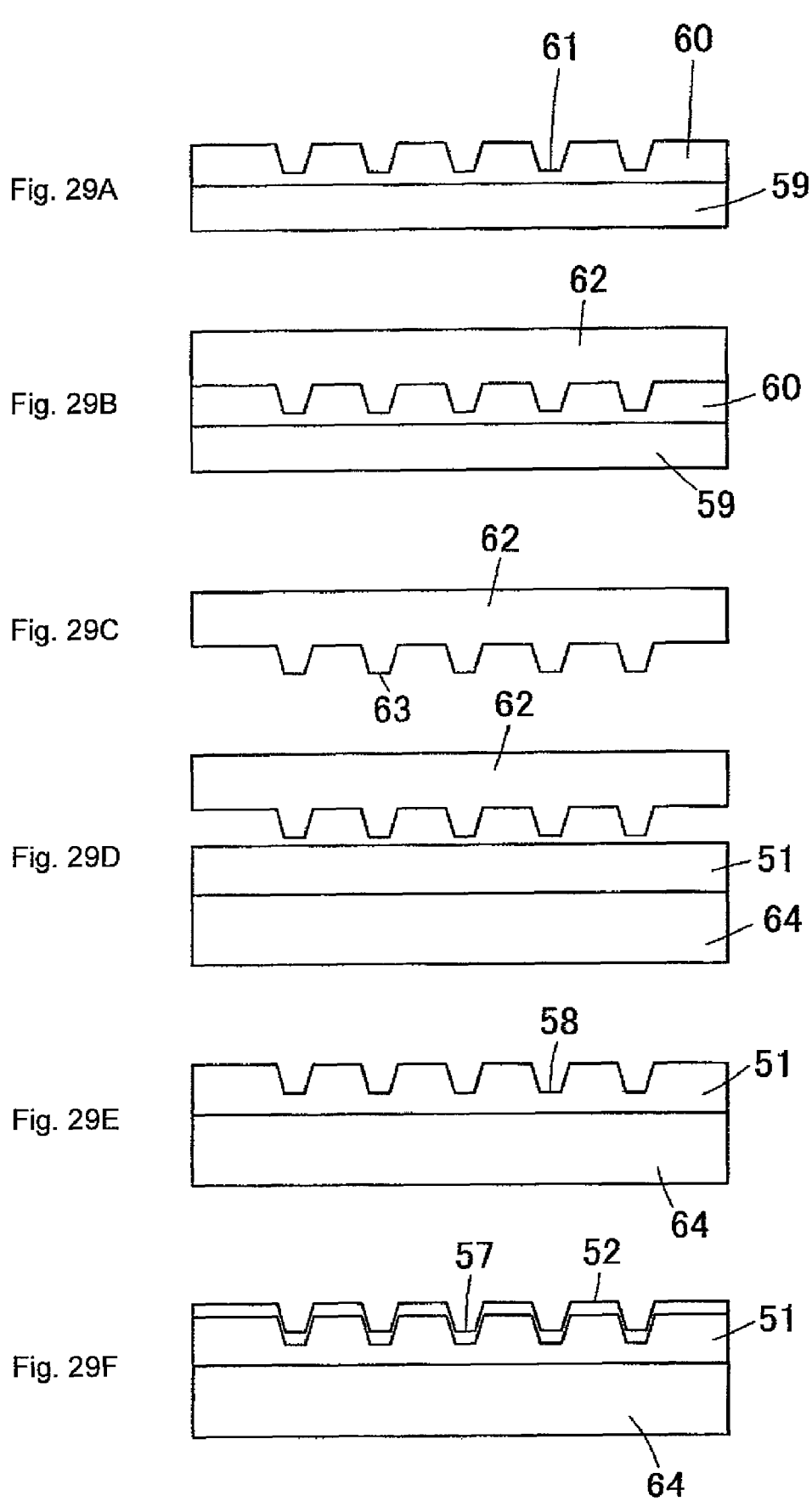
FIGS. 29A to 29F show views describing the manufacturing steps of the sensor chip of the first embodiment.
Figure 30:
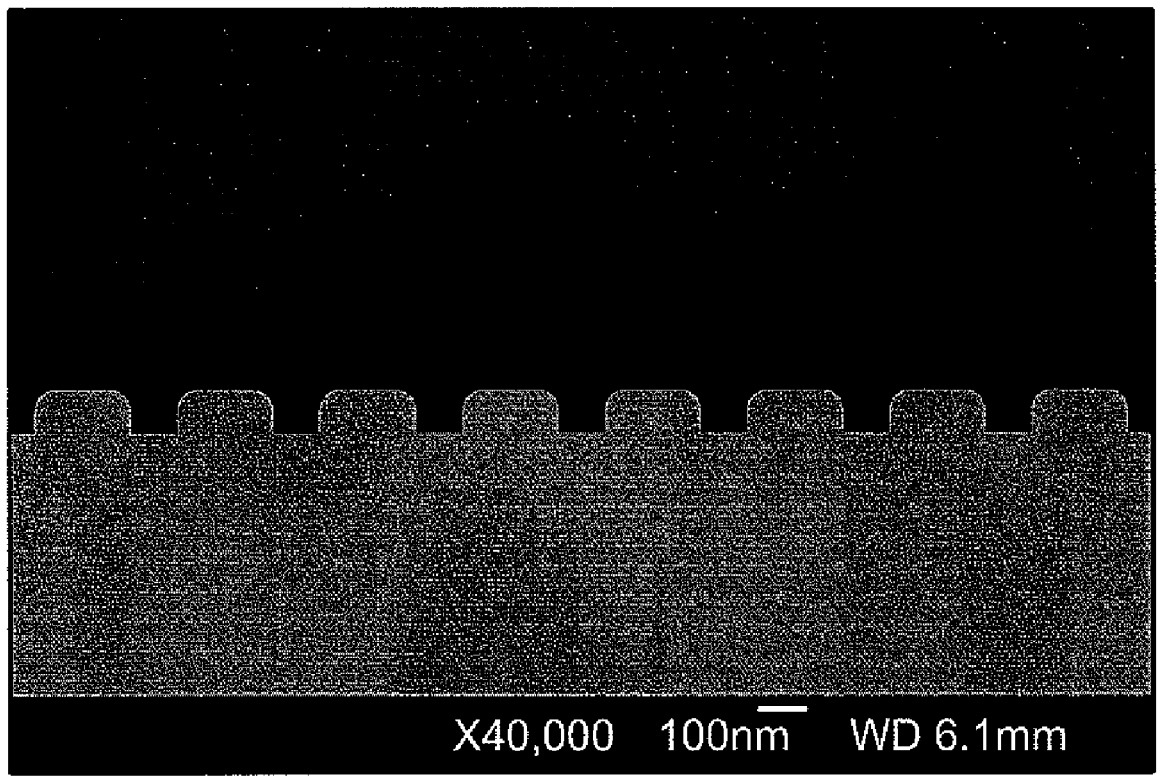
FIG. 30 shows a view of a cross section of the sensor chip manufactured through the steps FIGS. 26A to 26F.

Metals such as Au and Ag were then deposited on the surface of the substrate 51 of the duplicate copy obtained in this manner through sputtering to form a metal layer 52 reflecting the shape of the depression 58, thereby obtaining a substrate portion of the sensor chip 39 as shown in FIG. 29F. If the adherence between the surface of the substrate 51 and the metal layer 52 is not sufficient, an adherence layer such as Ti, Cr may be arranged between the substrate 51 and the metal layer 52. The thickness of the metal layer 52 is desirably greater than or equal to 40 nm in order to obtain sufficient light quantity of the reflected light. However, since the cost and the manufacturing throughput are not satisfactory if the metal layer 52 is too thick, a film thickness of about 40 to 100 nm is realistically desired. A picture of a cross section of the substrate portion of the sensor chip 39 manufactured in this manner (obtained by taking the cross sectional structure through an AFM, an SEM) is shown in FIG. 30.

As shown in FIG. 26, the inclination angle β of the side wall faces of the concave part 57 is preferably 90 degrees. In order to obtain such concave part 57, the side wall face of the concave pattern 61 formed in the master must be processed so that the inclination angle becomes 90 degrees. In order to process the concave pattern 61 having high perpendicularity in the master, a substrate having a wafer surface of 110 plane is used for the Si substrate 59, the surface of the Si substrate 59 is covered with a protective film such as $SiO_2$, and thereafter, the protective film is opened at a concave pattern forming position through dry etching, and the like. The Si substrate 59 is then subjected to anisotropic wet etching using etchant such as KOH and TMAH through the opening, thereby manufacturing the concave pattern 61 which inclination angle of the side wall face is substantially 90 degrees in the Si substrate 59. A relatively perpendicular concave pattern can be manufactured by using Cr etc. for the mask and dry etching the Si substrate with the DRIE and the like.

Since the sensor chip 39 of the present invention merely has a configuration in which the concave part 57 is arranged on the surface of the metal layer 52, the sensor chip 39 can be easily and conveniently manufactured using the nanoimprinting technique, and the sensor chip 39 can be mass produced inexpensively and at high accuracy. That is, the manufacturing efficiency is not satisfactory since the sensor chip has an island configuration in which the metal parts of metal fine particles etc. are discretely distributed in the conventional local surface plasmon resonance sensor, whereas the sensor chip 39 of the present invention has a continuous configuration in which the metal is formed without discontinuing, and thus the sensor chip 39 is efficiently manufactured by simply forming the metal layer 52 on the concave part 57 formed on the substrate.

Therefore, according to the present invention, the sensor chip 39 can be mass produced inexpensively and at high accuracy, and the sensor chip 39 having a very high sensitivity can be manufactured, and thus problems of sensitivity and mass productivity, which are problems caused by metal fine particles in the conventional local surface plasmon resonance, are solved according to the present invention.

(Comparison with Diffraction Grating Type Propagation Surface Plasmon Resonance Sensor)

Figure 2:
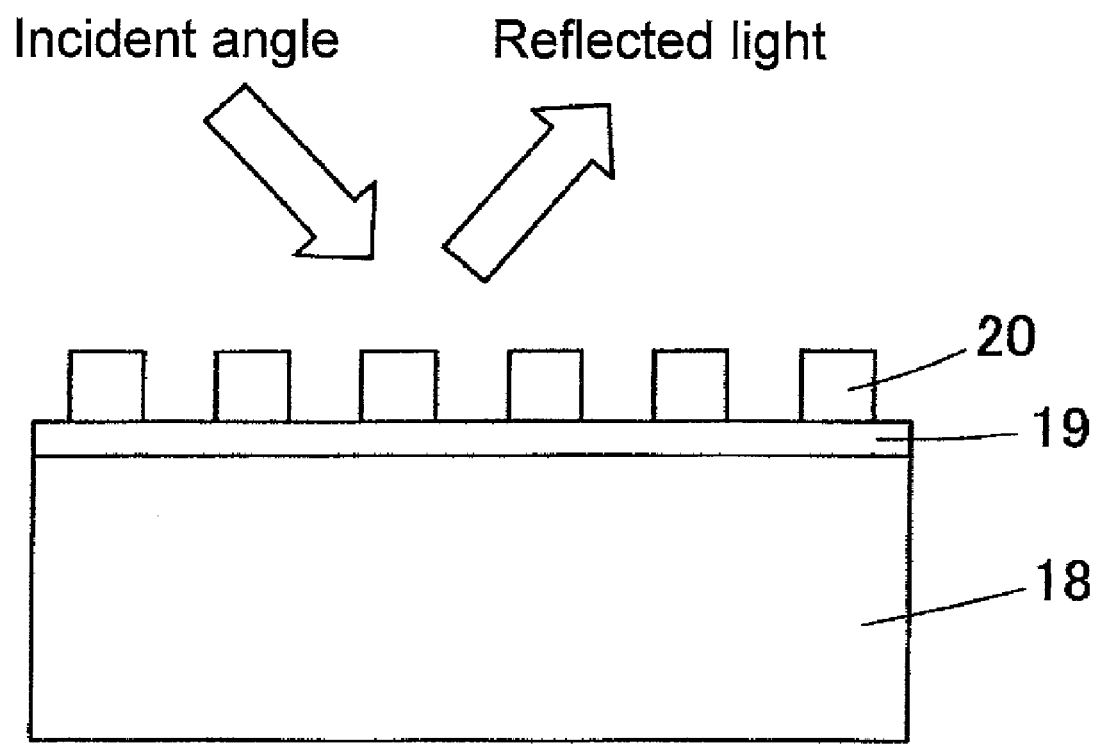
FIG. 2 shows a schematic view of a configuration of the propagation surface plasmon resonance sensor using a diffraction grating in prior art.
Figure 3:
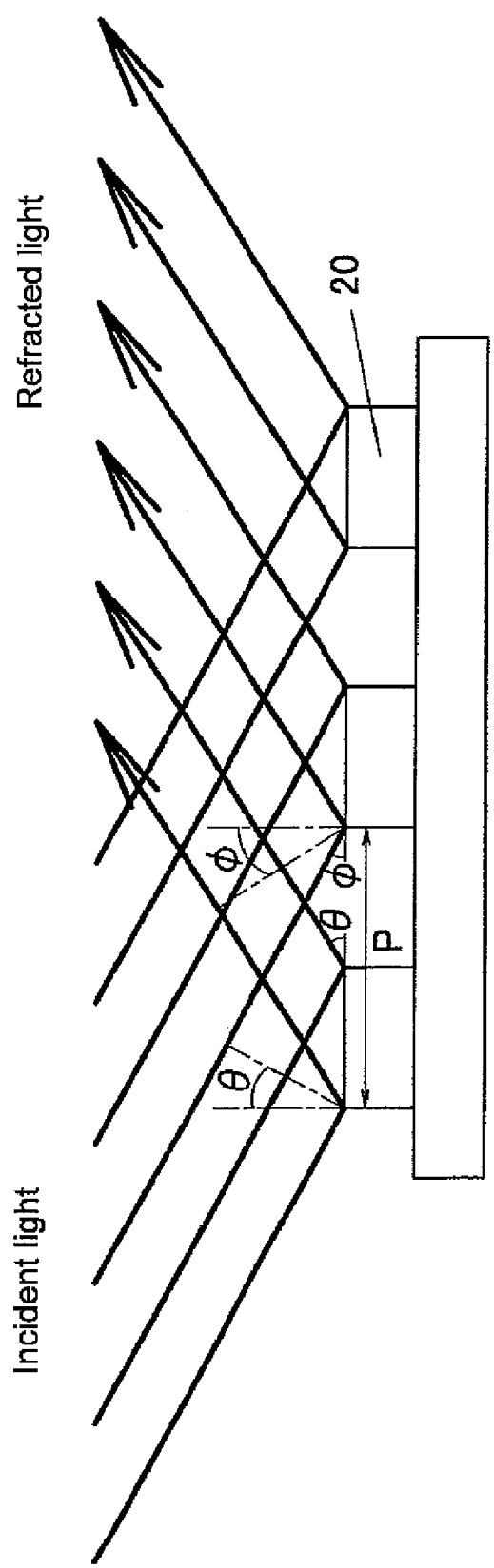
FIG. 3 shows a view of a state where an incident light causes diffraction in the propagation surface plasmon resonance sensor using the diffraction grating in prior art.
Figure 4A:
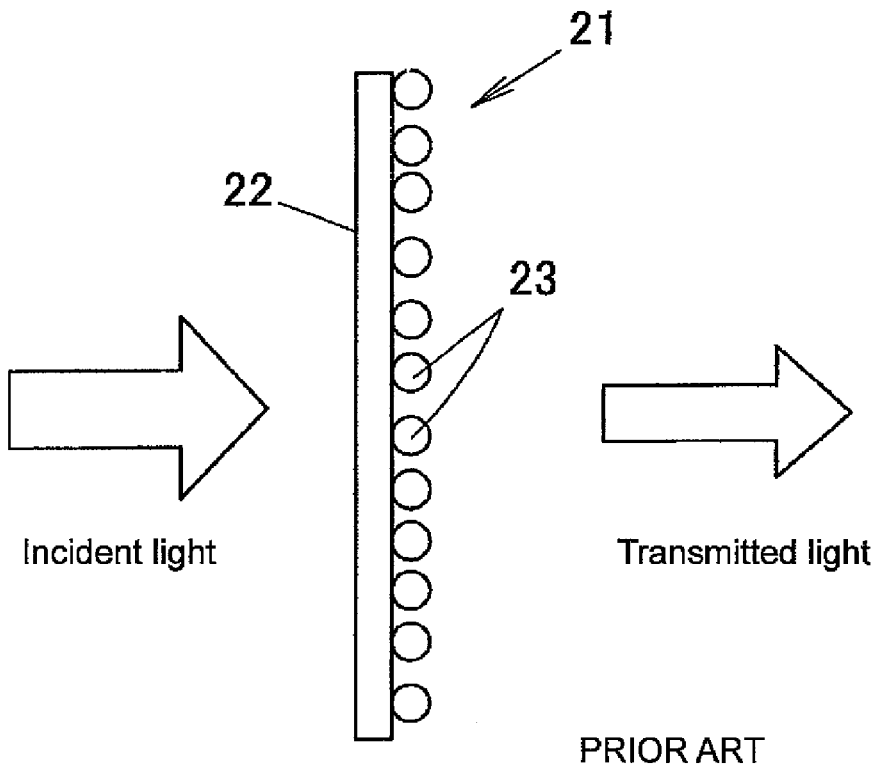
FIG. 4A shows a schematic view of a configuration of a local surface plasmon resonance sensor in prior art.
Figure 4B:
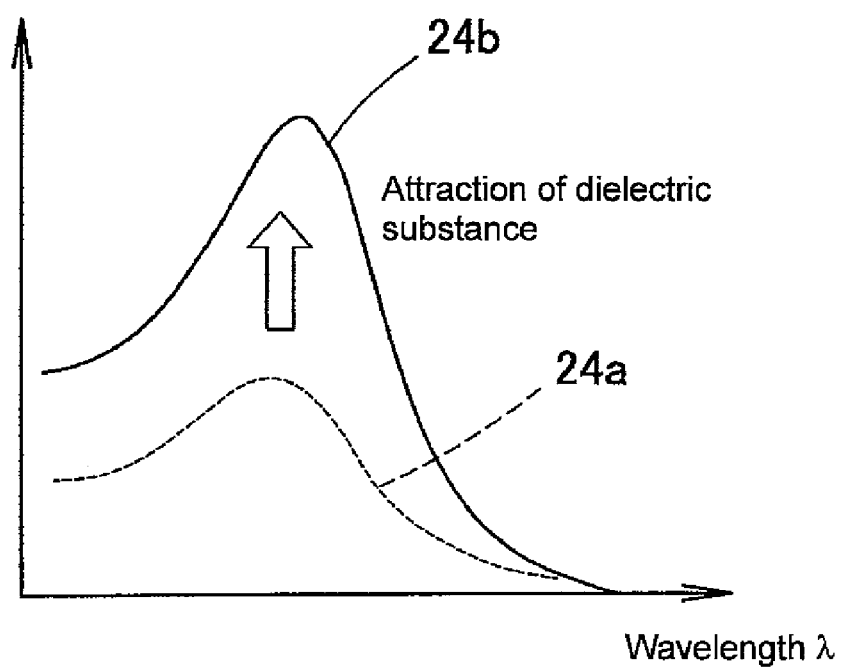
FIG. 4B shows a view of an example of absorbance characteristic measured by the local surface plasmon resonance sensor of FIG. 4A.
Figure 5:
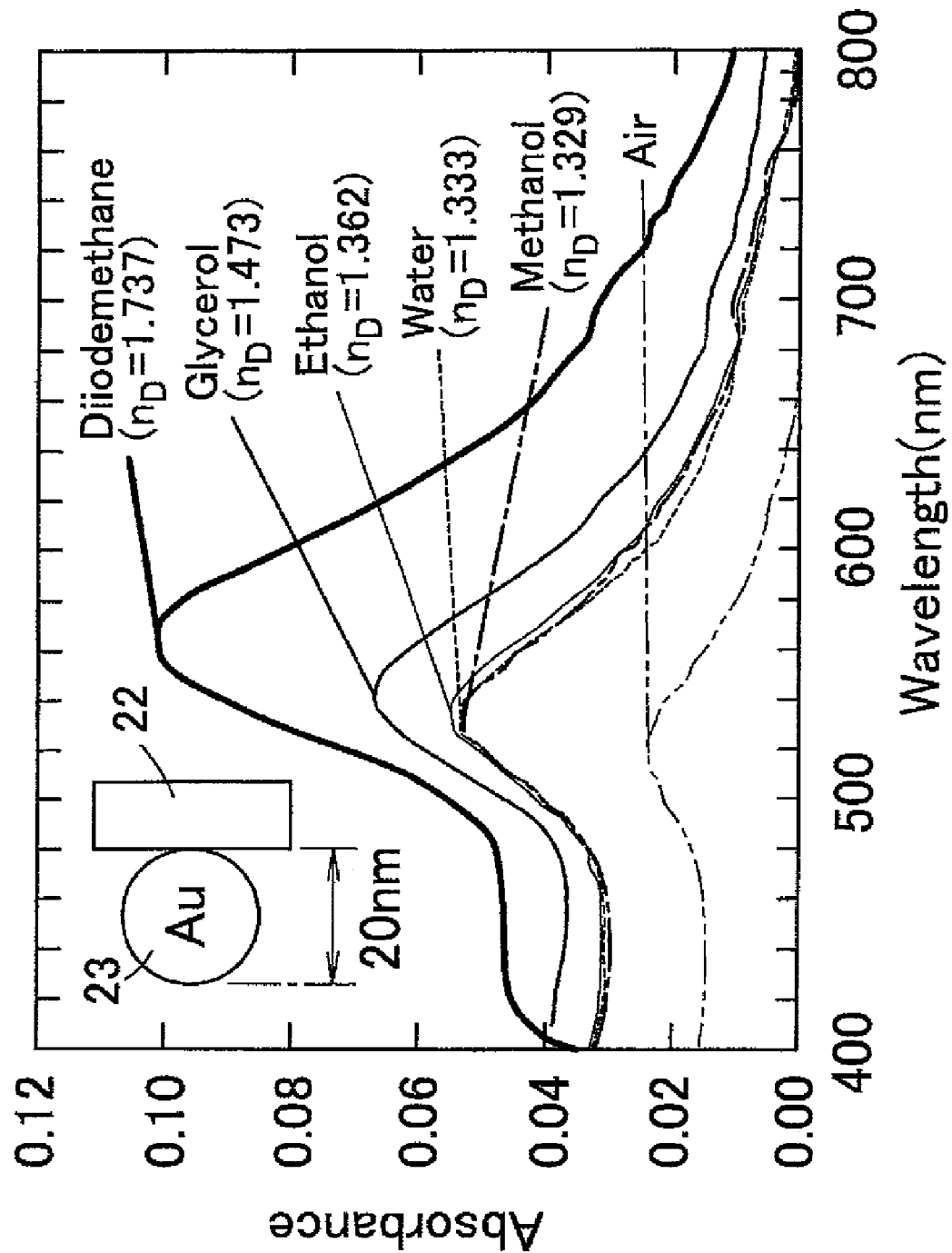
FIG. 5 shows a view of "absorbance spectrum of when a glass substrate deposited with gold nano particle having an average diameter of 20 nm is immersed in a liquid having various indexes of refraction" measured by the local surface plasmon resonance sensor of FIG. 4.
Figure 6B:
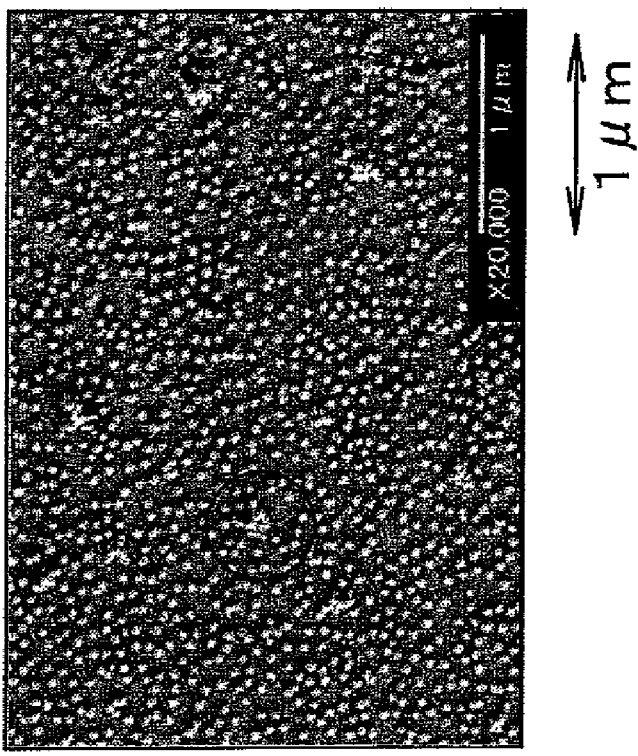
FIG. 6B shows a view of a state in which the metal fine particles are immobilized on the substrate at a relatively large distribution density according to a method of immobilizing the metal fine particles on the glass substrate by immersing the glass substrate in a colloidal solution.
Figure 6A:
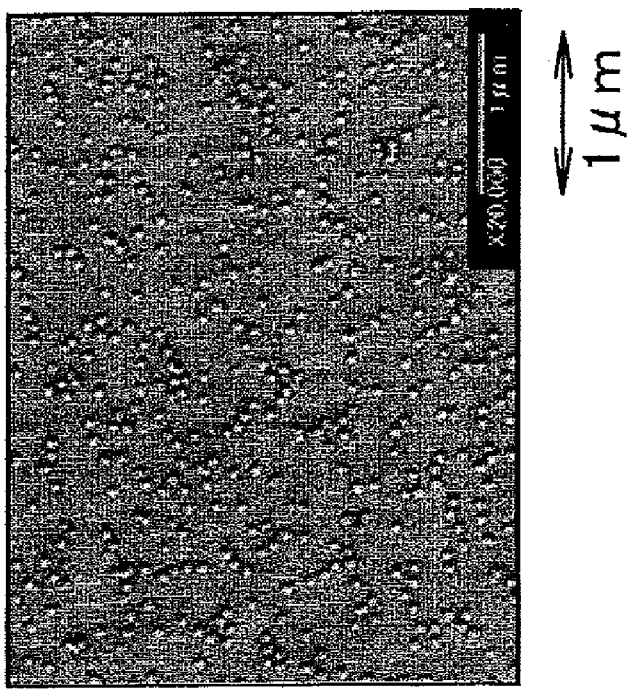
FIG. 6A shows a view of a state in which the metal fine particles are immobilized in a relatively small distribution density.
Figure 7A:
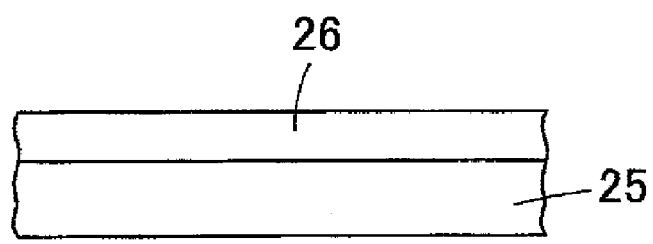
FIGS. 7A to 7F show views describing a method of manufacturing a metal nano configuration in which the metal fine particles are evenly arrayed using an electron beam.
Figure 7B:
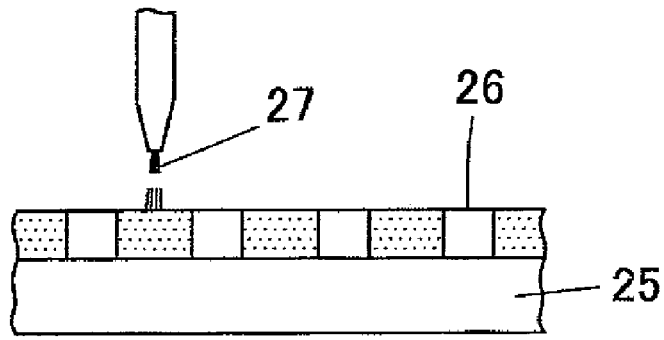
Figure 7C:
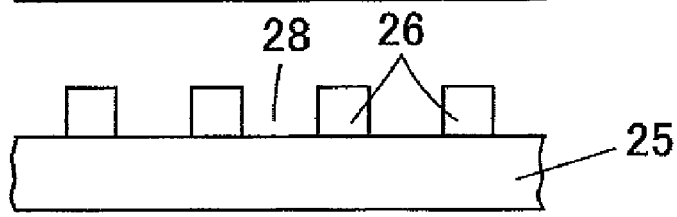
Figure 7D:
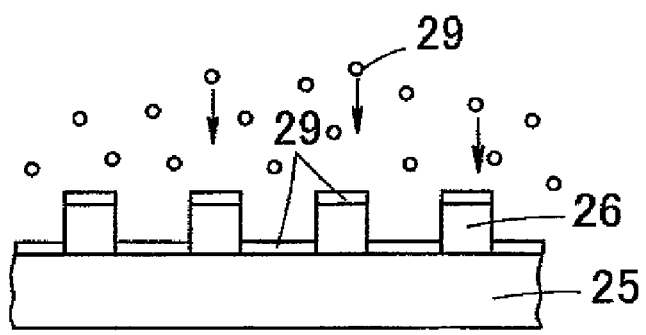
Figure 7E:
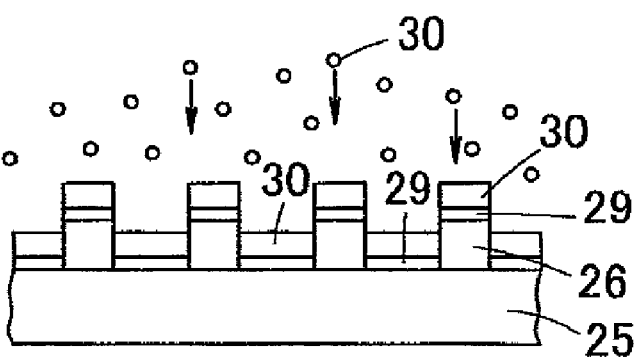
Figure 7F:
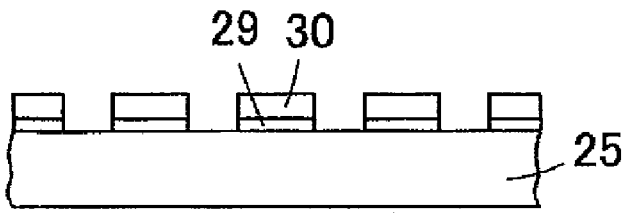
Figure 8:
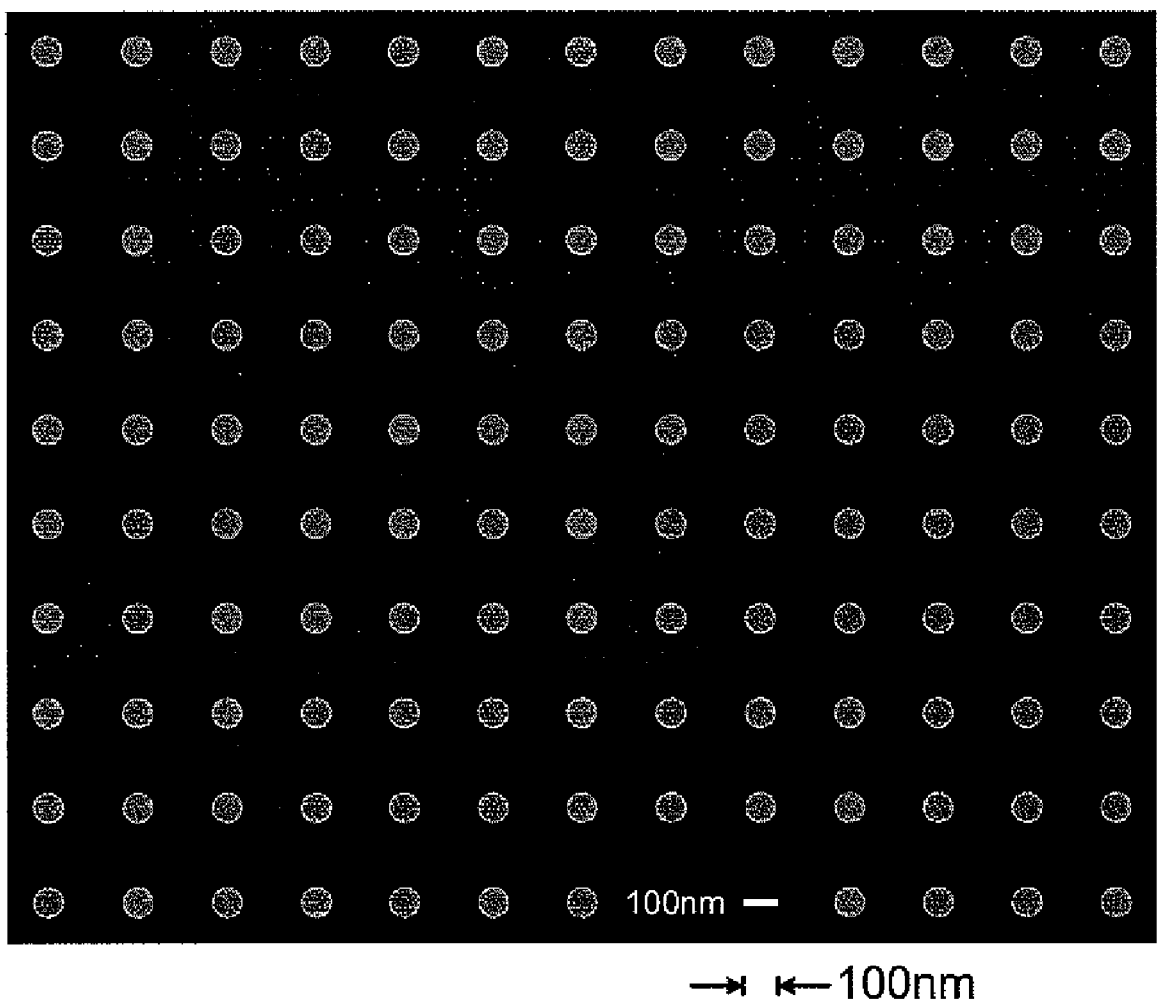
FIG. 8 shows a view of a pattern of the metal fine particles obtained by the method of FIG. 7.

Many reports on arranging concave-convex parts on the metal surface as diffraction grating for generating propagation SPR have been made. One example has been described in FIG. 2. On the other hand, not many reports have been made on the local surface plasmon resonance sensor generated inside the concave structure arranged on the surface of the metal layer, and the present invention is the first report to actually review the same as a sensor. However, the aspect of including the concave structure is common between the diffraction grating type propagation surface plasmon resonance sensor and the sensor chip of the present invention, and thus the difference between the propagation surface plasmon resonance sensor (hereinafter referred to as diffraction grating type propagation SPR sensor) including the diffraction grating, and the local surface plasmon resonance sensor (hereinafter referred to as concave structure local SPR sensor) including the concave structure will be described below.

Regarding the pattern shape, the concave part which side wall face is perpendicular is preferable in the concave structure local SPR sensor. In the concave structure local SPR sensor, the concave structure is not provided to serve as a diffraction grating but to generate local SPR therein, and thus the width (Wm) of the concave part is desirably smaller than one half with respect to the array pitch (P) of the concave part, and the flat plane between the adjacent concave parts is wider than the width of the concave part.

Since the concave structure of the concave structure local SPR sensor does not serve as diffraction grating, the pitch P is desirably smaller than or equal to ½ of the wavelength of the light. When the light of visible light region is used, the period of the concave part is preferably less than or equal to 400 nm to be separated from the diffracted light. In particular, diffraction does not occur on light of any wavelength of the visible light region if the period is less than or equal to 200 nm.

In the concave structure local SPR sensor, the light is preferably entered perpendicularly to enhance the sensitivity.

In the concave structure local SPR sensor of the present invention, the sensing area is narrow or a few dozen nm, and only a specific substance very close to the metal layer can be detected at high accuracy. Furthermore, a very high sensitivity can be obtained since SPR can be trapped within the concave part in the concave structure local SPR sensor.

(Variant)

Figure 31:
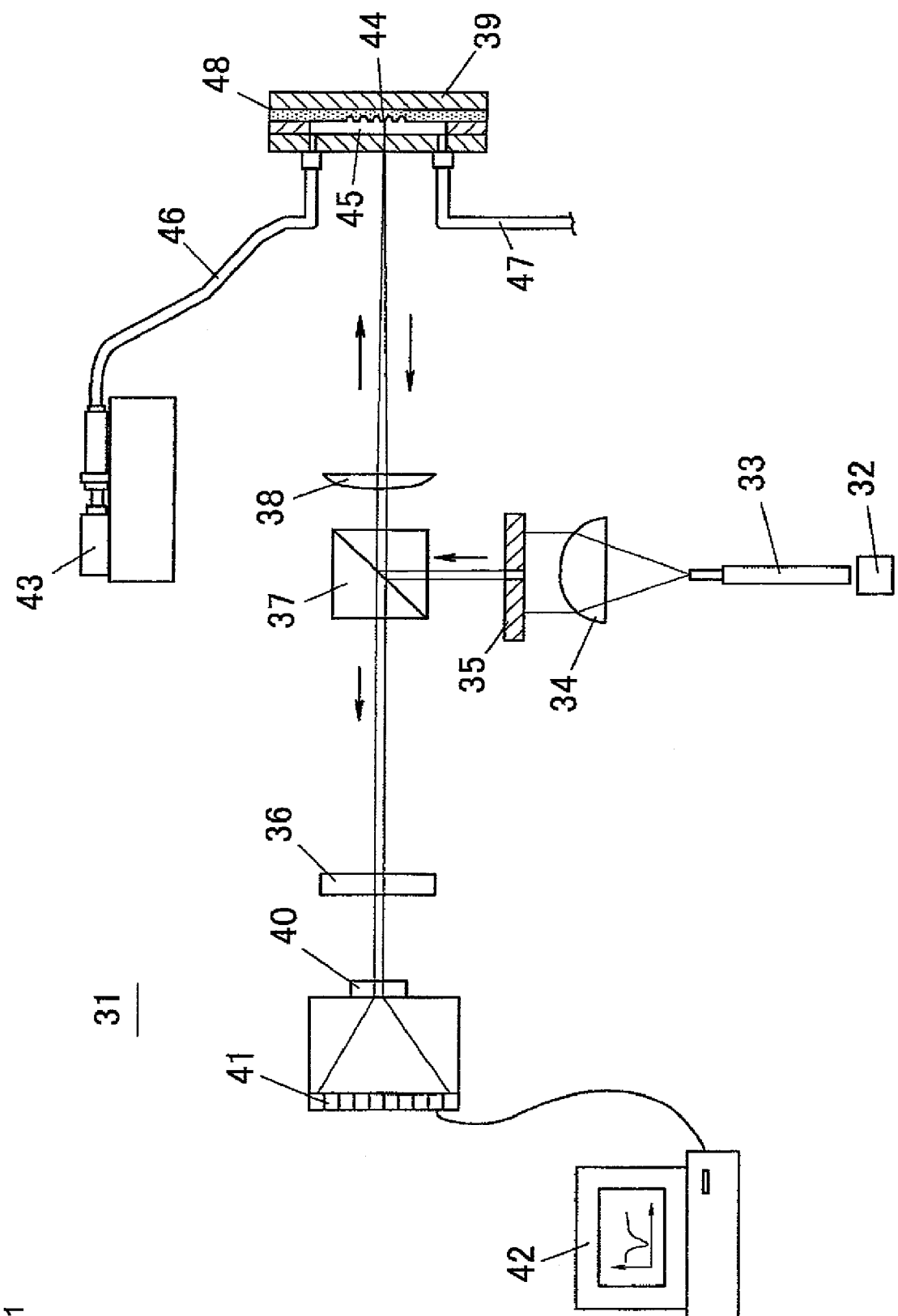
FIG. 31 shows a schematic view of a variant of a local SPR sensor of the embodiment.

FIG. 31 shows a schematic view showing a variant of the local SPR sensor 31 of the first embodiment. The light of linear polarization is irradiated on the sensor chip 39 in the embodiment of FIG. 9, but the light of specific polarizing surface is retrieved from the light reflected at the sensor chip 39 in the variant of FIG. 31. That is, in the variant, white light narrowed by the collimator lens 34 and the collimator plate 35 is entered to the beam splitter 37, and the light reflected in a direction of 90 degrees by the beam splitter 37 is collected in the measurement region 44 of the sensor chip 39 by the objective lens 38. The non-polarized white light reflected by the measurement region 44 is again transmitted through the objective lens 38 and converted to parallel light, and thereafter, entered to the beam splitter 37. The polarization plate 36 is arranged between the beam splitter 37 and the spectroscope 40, where the light straightly transmitted through the beam splitter 37 becomes light of linear polarization by passing through the polarization plate 36, and is divided by the spectroscope 40 and received by the photodetector 41.

In this case, the polarization plate 36 is arranged in a direction in that the polarizing direction is orthogonal to the longitudinal direction of the concave part 57 arranged in the sensor chip 39. That is, the polarization plate 36 is arranged so as to transmit only the linear polarization component having a polarizing surface orthogonal to the longitudinal direction of the concave part 57 of the light reflected at the measurement region 44. When the longitudinal direction of the concave part 57 is facing a direction perpendicular to the plane of drawing of FIG. 31, the polarization plate 36 is arranged so that the polarizing direction is perpendicular to the optical axis and is parallel to the plane of drawing. Therefore, in the variant as well, only the light of polarizing surface perpendicular to the longitudinal direction of the concave part 57 can be detected by the photodetector 41 and high detection sensitivity can be realized.

In this variant, the position of the light projecting side and the light receiving side is the opposite of that of FIG. 9 due to the following reasons. From the arrangement of FIG. 9 or the arrangement of FIG. 31, by interchanging the positions of the light receiving system and the light projecting system, the light having the polarizing surface tilted from the direction perpendicular to the longitudinal direction of the concave part 57 enters the photodetector 41 when the angle of the beam splitter 37 is tilted, which lowers the sensor sensitivity.

In the case of the local SPR sensor 31 of FIG. 9, since the light projecting system and the polarization plate are at positions in the perpendicular direction of the sensor chip 39, the light of linear polarization that has passed through the polarization plate 36 straightly passes through the beam splitter 37. Therefore, the polarizing surface of the light of linear polarization that enters the concave part 57 will not tilt even if the arrangement angle of the beam splitter 37 contains error by arranging so that the polarizing direction of the polarization plate 36 and the longitudinal direction of the concave part 57 become orthogonal.

Similarly, in the case of the variant of FIG. 31, since the light receiving system and the polarization plate are at positions in the perpendicular direction of the sensor chip 39, the light that has straightly passed through the beam splitter 37 becomes light of linear polarization by passing through the polarization plate. Therefore, the polarizing surface of the light of linear polarization that enters the concave part 57 will not tilt even if the arrangement angle of the beam splitter 37 contains error by arranging so that the polarizing direction of the polarization plate 36 and the longitudinal direction of the concave part 57 become orthogonal.

In the local SPR sensor 31 of example 1 and the variant, the light that resonates the strongest with the metal layer 52 in the concave part 57 is detected with the photodetector using the polarization plate, but in some cases, the polarization plate may not be used. In the local SPR sensor 31 of the present invention, the sensor sensitivity becomes the highest when the polarizing surface of the light of linear polarization detected by the photodetector 41 is perpendicular to the longitudinal direction of the concave part 57, and sensitivity is not provided when the polarizing surface becomes parallel to the longitudinal direction of the concave part 57. Therefore, when the polarization plate is not used, the sensitivity of the local SPR sensor 31 lowers. However, the polarization plate can be used for measurement objects with large reactive quantity that can be measured at low sensitivity, depending on the measurement target. The polarization plate also does not need to be used when the concave part 57 has a shape that is isotropic and which longitudinal direction cannot be defined such as circular column or cylinder.

Second Embodiment

The sensor chip 39 according to a second embodiment of the present invention will be described. The sensor chip 39 of the second embodiment has a feature in that the central part of the bottom surface of the concave part 57 is raised towards the opening side.

Figure 32A:
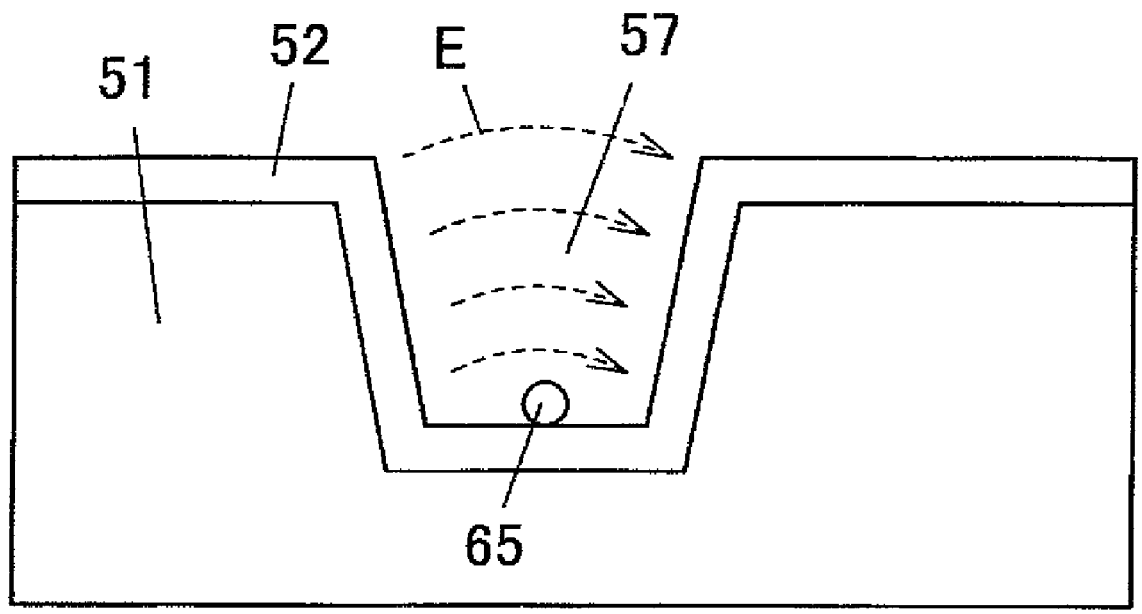
FIG. 32A shows a view of a cross section of a concave part according to the first embodiment of the present invention; 32B shows a view of a cross section of a concave part according to a second embodiment.

Looking at the electric field distribution generated inside the concave part 57 shown in FIG. 17 in detail, it can be seen that the electric field intensity is not as strong in the vicinity of the bottom part of the concave part 57. This is because the electric force line in the concave part 57 is raised to the opening side. Thus, when the bottom surface of the concave part 57 is a flat plane as in the first embodiment, even if a specific substance such as protein bonds to the bottom surface of the concave part 57 as shown in FIG. 32A, such specific substance is positioned in a region of small electric field intensity, and thus change in index of refraction by the specific substance does not greatly contribute to signal change.

Figure 32B:
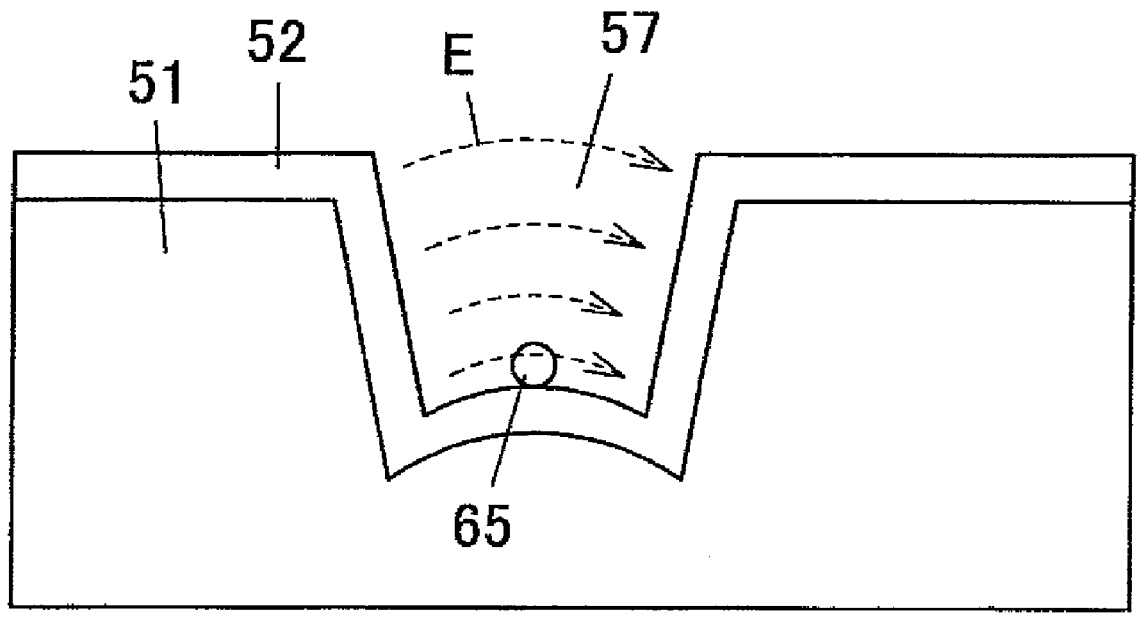

As shown in FIG. 32B, in the sensor chip of the second embodiment, the central part of the bottom surface of the concave part 57 is made slightly shallower than both ends at a cross section perpendicular to the longitudinal direction of the concave part 57, so that the central part of the bottom surface rises towards the opening side. Accordingly, when a specific substance such as protein bonds to the bottom surface of the concave part 57, such specific substance is lifted by the bottom surface of the concave part 57 and positioned in a region of relatively large electric field intensity, and thus signal change by change in index of refraction is made large and the sensitivity enhances.

Figure 33A:
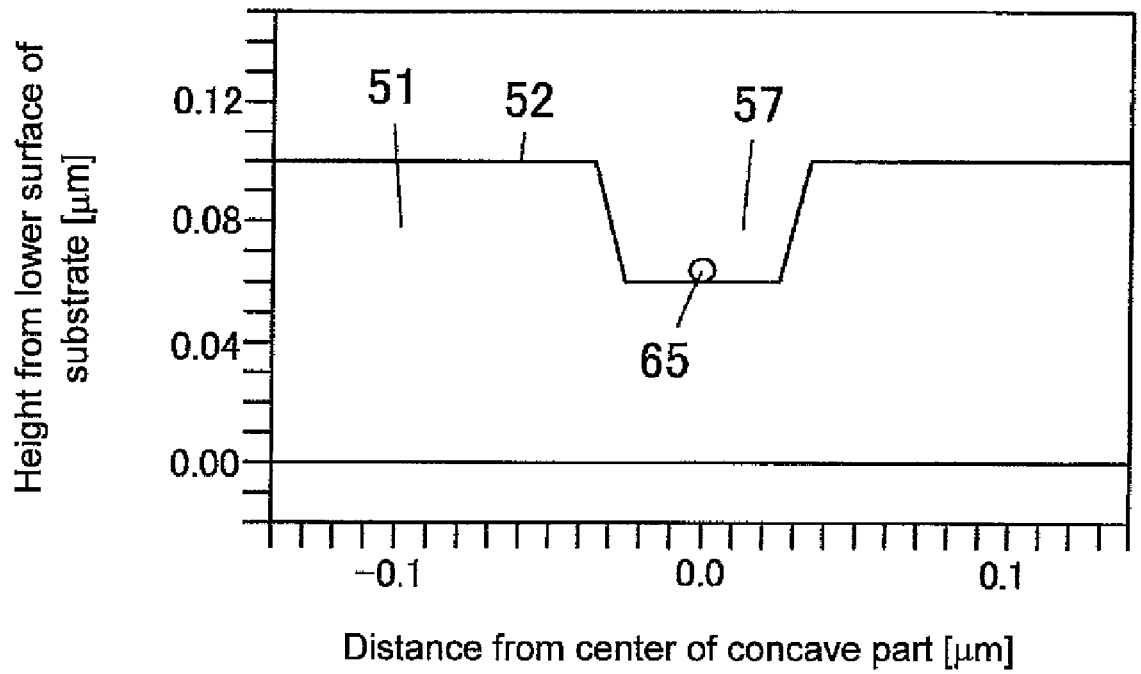
FIG. 33A shows a view of a cross section of a concave part in a prototype of the first embodiment of the present invention, and 33B shows a view of a cross section of a concave part in a prototype of the second embodiment of the present invention.
Figure 33B:
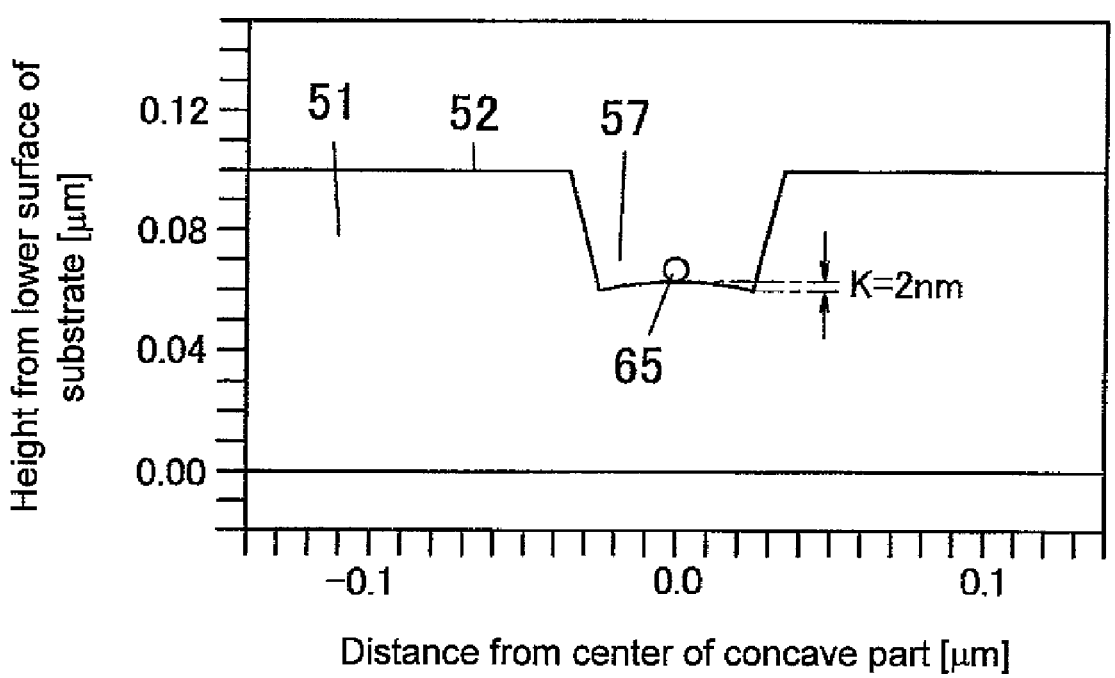

The effect of raising the bottom surface of the concave part 57 was checked through simulation. As shown in FIG. 33A one of the concave structure model used in checking has a concave part 57 having an average pattern width of (Wm+Bm)/2=60 nm, a depth of Dm=40 nm, an inclination angle of the side wall face of β=75 degrees and a pitch of P=300 nm, and the bottom surface thereof is flat. The other concave structure model is, as shown in FIG. 33B, has an average pattern width of (Wm+Bm)/2=60 nm, a depth of Dm=40 nm, an inclination angle of the side wall face of β=75 degrees and a pitch of P=300 nm, and the central part of the bottom surface thereof is raised by K=2 nm than both ends.

The change in resonance wavelength of before and after the substance 65 (assume BSA (bovine serum albumin)) having a diameter of 3.8 nm and an index of refraction of 1.57 was attached to the central part of the bottom surface of the concave part 57 was examined. In the model in which the bottom surface is a flat plane as shown in FIG. 33A, the resonance wavelength before the attachment of the substance 65 is 630.0852 nm, and the resonance wavelength after the attachment is 630.0873 nm, and thus the signal shifted by $\Delta\lambda=0.0021$ nm. In the model in which the central part of the bottom surface is raised by K=2 nm as shown in FIG. 33B, the resonance wavelength before the attachment of the substance 65 assuming BSA is 628.4540 nm, and the resonance wavelength after the attachment is 628.4615 nm, and thus the signal shifted by $\Delta\lambda=0.0075$ nm. Therefore, the amount of signal change enhanced to about 3.6 times by raising the central part of the bottom surface of the concave part 57 by 2 nm from both ends.

Figure 34:
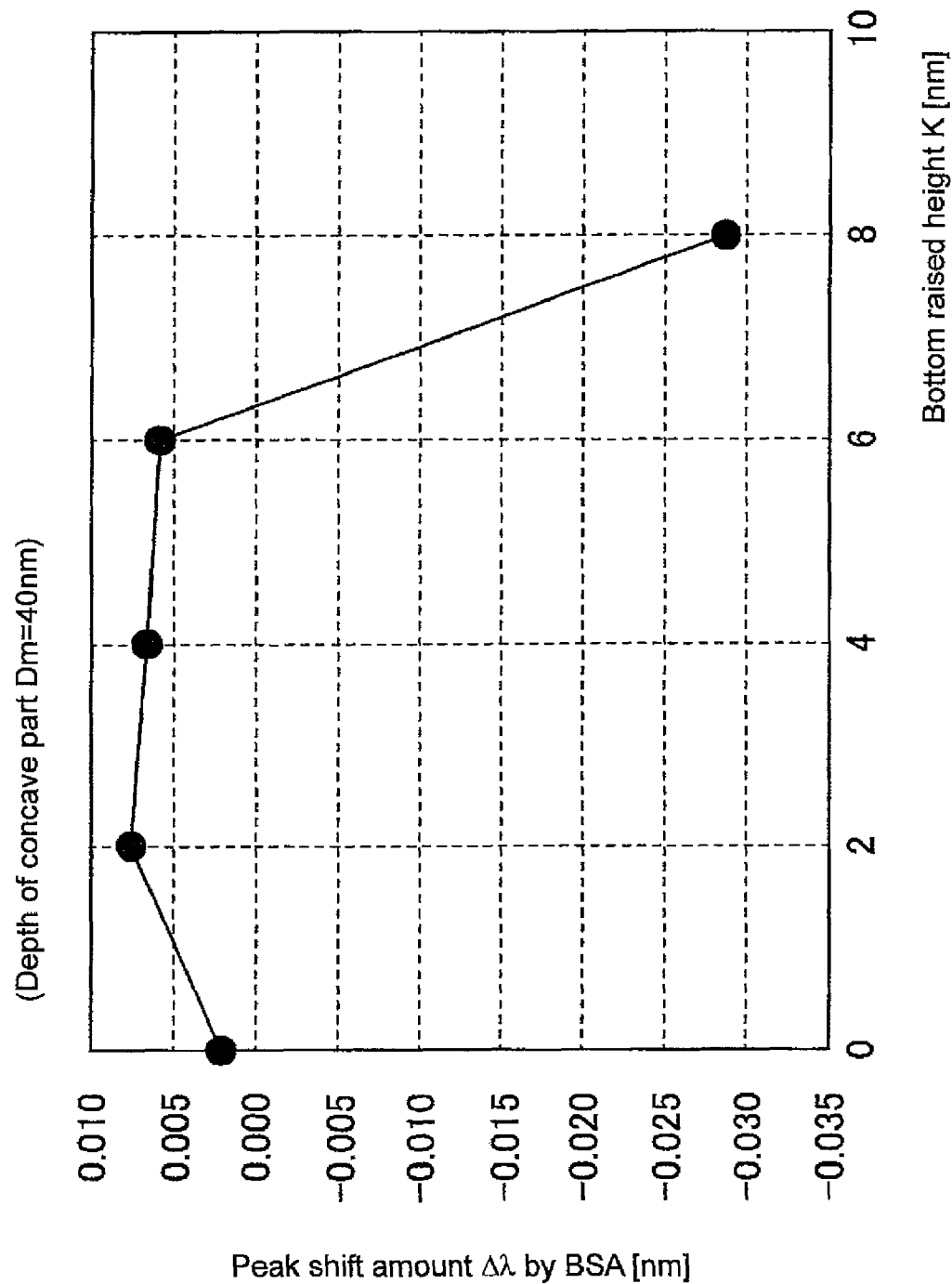
FIG. 34 shows a view of a correlation between a bottom raised height K of the bottom surface of the concave part and the shifted amount AA of the resonance wavelength.
Figure 36A:
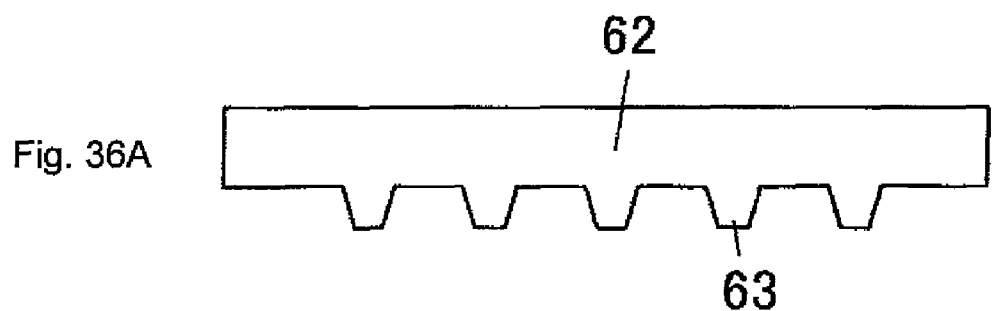
FIGS. 36A to 36D show views describing another manufacturing steps of the sensor chip of the second embodiment.
Figure 36B:
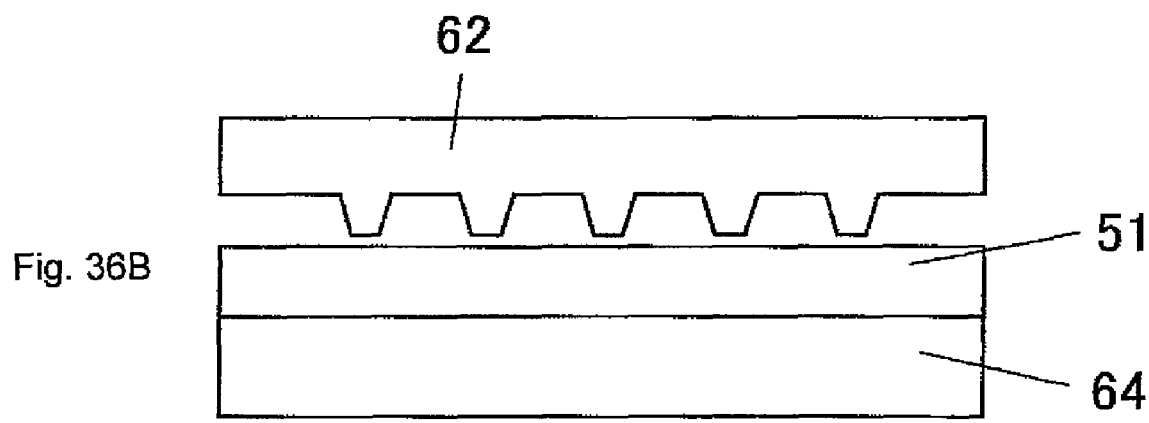
Figure 36C:
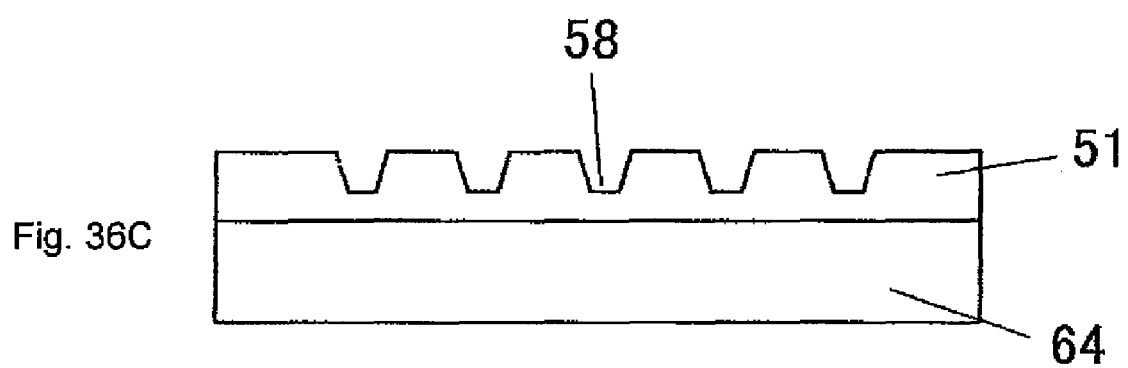
Figure 36D:
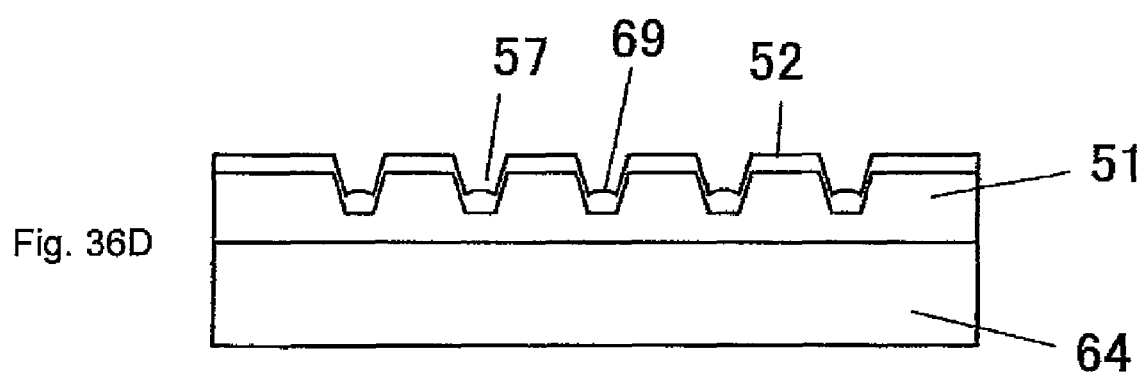

The amount of shift in the resonance wavelength when the height of raising the bottom surface (hereinafter referred to as bottom raised height K) is changed was examined. This result is shown in FIG. 34. As apparent from FIG. 34, the amount of shift in the resonance wavelength increases by raising the central part of the bottom surface of the concave part 57 up to the bottom raised height K of 6 nm, but the resonance wavelength changes to negative side when the bottom raised height K becomes 8 nm. This is because the electric field distribution generated inside the concave part 57 becomes disordered as a result of having an excess amount of raise at the bottom surface, and the resonance phenomenon itself changes. From such results, the amount of raising the central part of the bottom surface is found to be greater than or equal to 5% and less than or equal to 20% with respect to the entire depth of the concave part 57.

(Manufacturing Method)

The method of manufacturing the sensor chip according to the second embodiment will now be described with FIG. 35. This manufacturing method is substantially the same as the manufacturing method of the first embodiment described in FIG. 29, and thus the different aspects will be mainly described. First, when manufacturing the master, a concave pattern 61 is formed on the photoresist 60 applied on the Si substrate 59 using the semiconductor manufacturing process, and a convex part 66 raised to a circular arc form is formed at the bottom surface of each concave pattern, as shown in FIG. 35A.

Ni is then deposited on the master to form the die 62, as shown in FIG. 35B, and a concave part 67 is formed at the lower surface of the inverted shape 63 of the lower surface of the die 62, as shown in FIG. 35C. Thereafter, as shown in FIG. 35D, nanoimprinting is performed on the PMMA (polymethyl methacrylate) applied on the glass substrate 64 using the die 62. As shown in FIG. 35E, the concave pattern of the master is transferred to the surface of the substrate 51 where PMMA is cured, a depression 58 is molded at the surface of the substrate 51, and a convex part 68 is formed at the bottom surface of the depression 58.

Metals such as Au or Ag is deposited on the surface of the substrate 51 of a duplicate copy obtained in this manner through sputtering to form a metal layer 52 reflecting the shape of the depression 58, whereby a concave part 57 and a raised part 69 of circular arc shape at the bottom surface thereof are formed in the metal layer 52 by the depression 58 and the convex part 68 at the bottom surface thereof, as shown in FIG. 35F.

Figure 37:
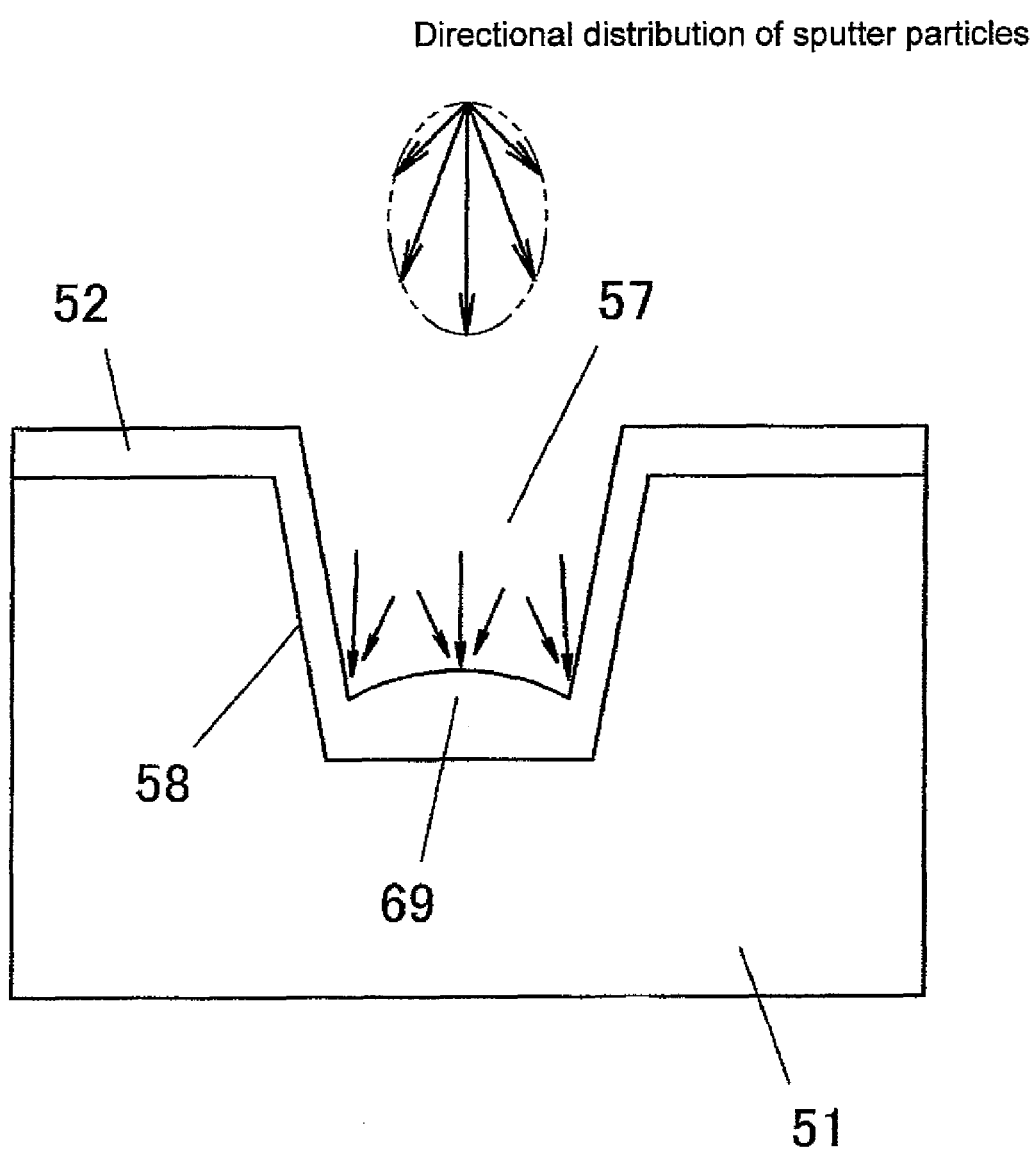
FIG. 37 shows a view describing a sputtering step of the manufacturing steps of FIG. 36.

A different method of manufacturing the sensor chip according to the second embodiment is shown in FIGS. 36 and 37. FIG. 36A shows the die 62 manufactured similar to FIGS. 29A to 29C of the first embodiment, and FIGS. 36B and 36C show steps same as FIGS. 29D and 29E. When the substrate 51 shown in FIG. 36C is molded through the nanoimprinting method, sputter particles such as Au and Ag are deposited on the surface of the substrate 51 through sputtering to form the metal layer 52. In the sputtering step, the spread of angular distribution of the sputter particles is adjusted by adjusting the degree of vacuum inside the chamber and the rotation number of the substrate. In the sputtering step, if the angular distributing in the incoming direction of the sputter particles has a spread of a certain extent, as shown in FIG. 37, the film thickness of the metal layer 52 becomes thick at the central part of the bottom surface where there are no shielding objects on both sides since the metal particles enter from both sides, and the film thickness of the metal layer 52 becomes thin at the ends of the bottom surfaces where one side is shielded since the metal particles enter only from one side. As a result, the central part of the bottom surface of the concave part 57 rises naturally by performing sputtering, whereby a raised part 69 forms at the bottom surface of the concave part 57, as shown in FIG. 36D.

Figure 38:
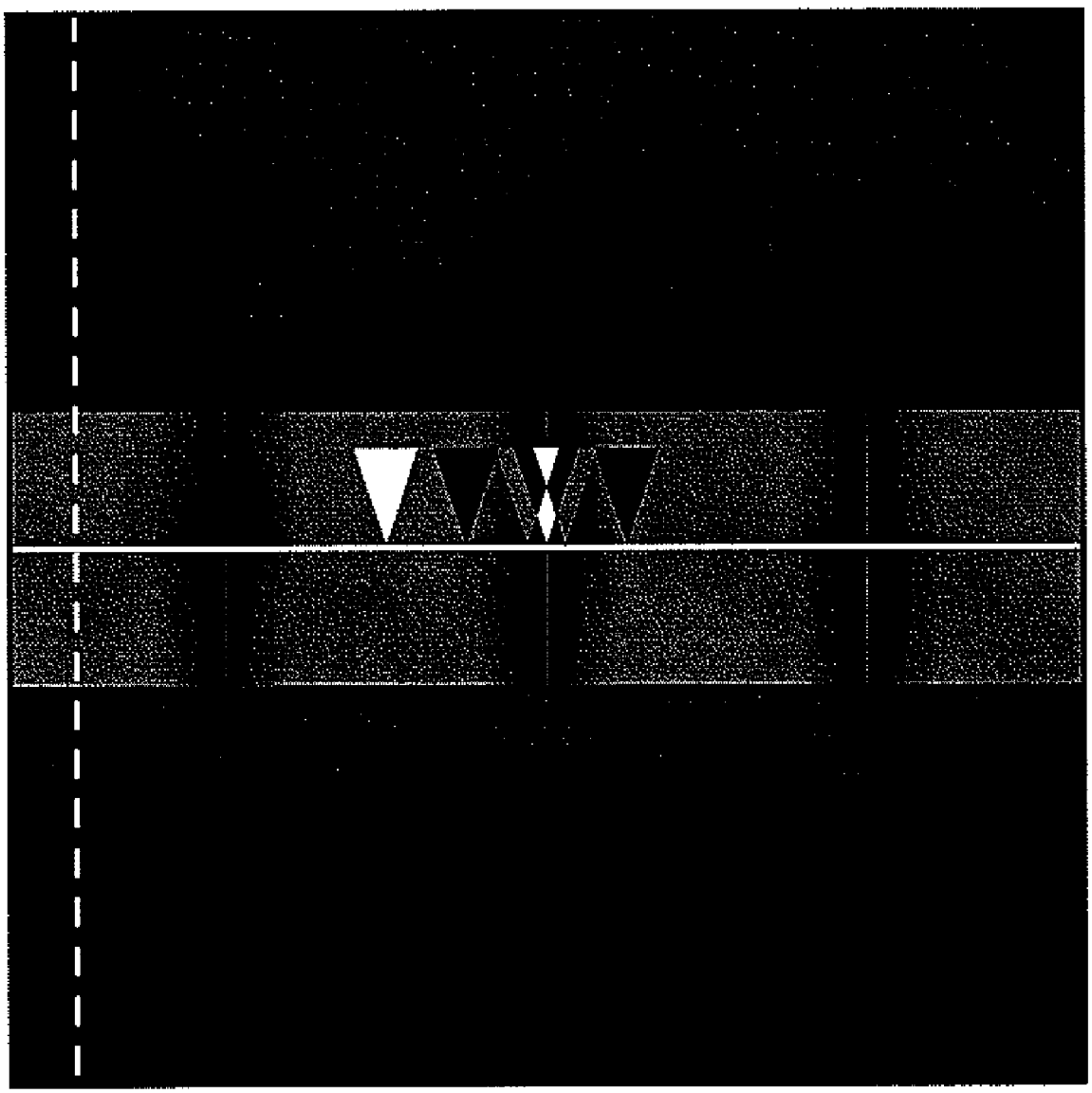
FIG. 38 shows a view of an AFM image of the sensor chip actually manufactured with the manufacturing method shown in FIGS. 36 and 37.
Figure 39:
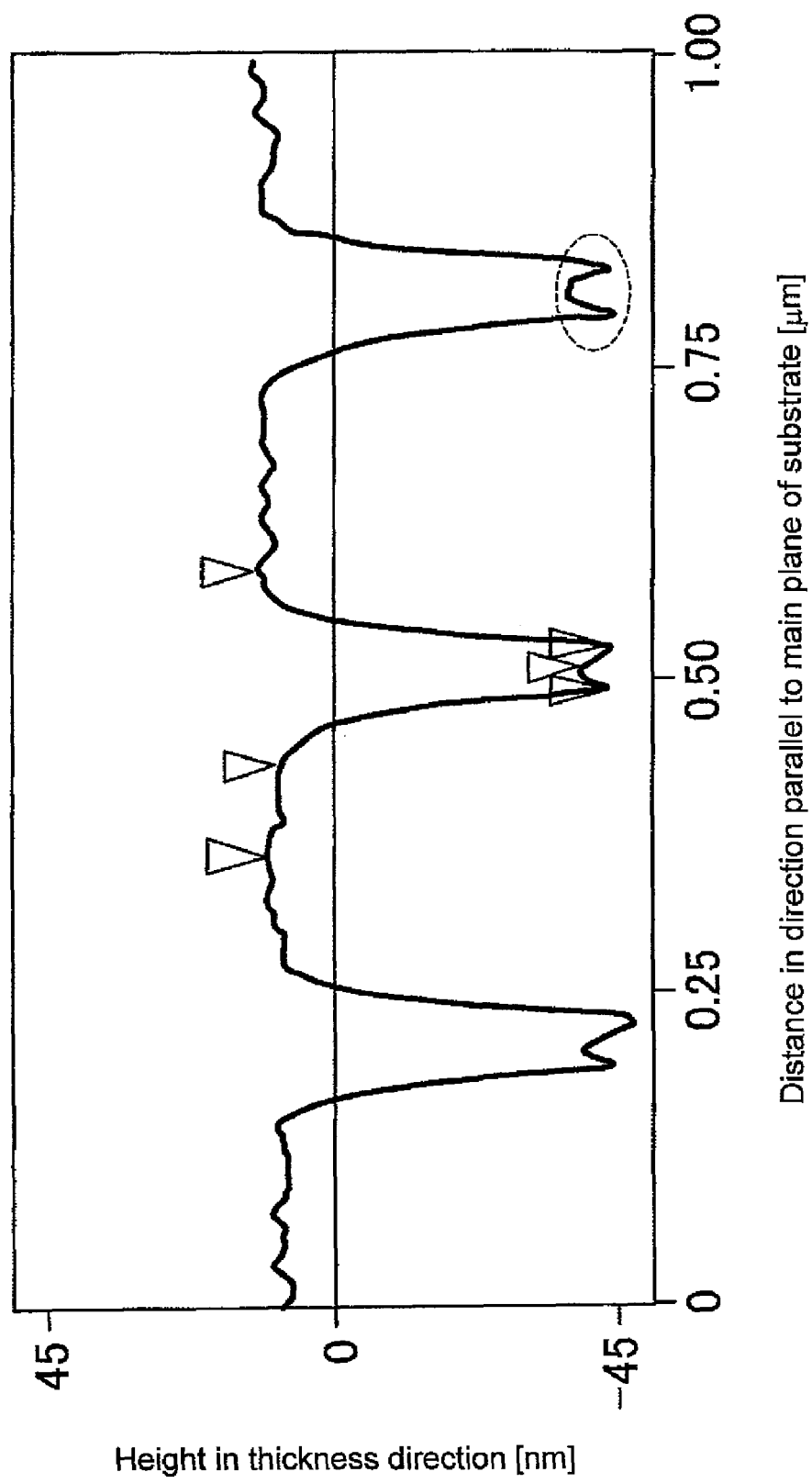
FIG. 39 shows a view of a cross sectional profile of the sensor chip of FIG. 38.

An AFM image of the sensor chip 39 actually manufactured through the manufacturing method described in FIGS. 36 and 37 is shown in FIG. 38. The portion that appears black in FIG. 38 is the concave part 57. FIG. 39 shows a view of a profile of the metal layer surface at the cross section of the sensor chip 39. The position with a triangular mark in FIG. 39 corresponds to the position with a triangular mark in FIG. 38. It can be recognized from FIGS. 38 and 39 that the central part of the bottom surface of the concave part 57 is higher than both ends by about a few nm by performing sputtering as in FIG. 39.

Third Embodiment

Figures 40A, 40B:
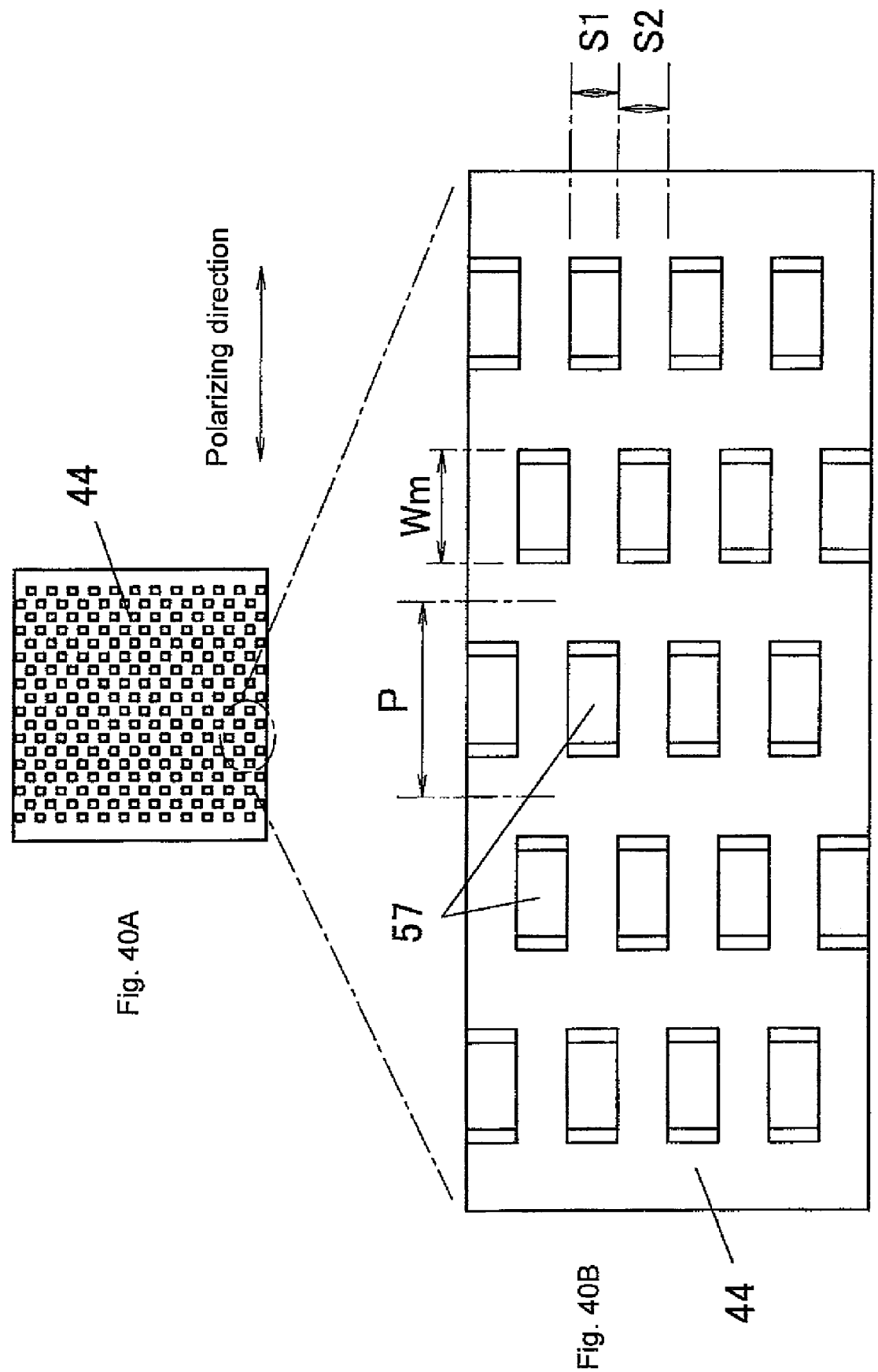
FIG. 40A show a plan view of a measurement region 44 in a sensor chip according to a third embodiment of the present invention.
FIG. 40B shows a view of one part of FIG. 44A in an enlarged manner.

The concave structure of the sensor chip according to the second embodiment of the present invention will now be described. In the sensor chip of the third embodiment, the concave part 57 is divided into plurals in the longitudinal direction, as shown in FIG. 40, as opposed to the concave part 57 extending in a groove form from end to end of the measurement region 44 as in the first embodiment. Consequently, the concave part 57 has a substantially rectangular concave structure, and is lined along two directions orthogonal to each other.

The manner of arraying the concave part 57 may be rectangular array (manner of arraying in a grid form) or delta array (manner of arraying in a staggering manner as in FIG. 40B), and the case of delta array will be described herein. The concave part 57 is lined at a constant pitch P similar to the first embodiment in a direction parallel to the polarizing surface of the incident light, but the width S1 of the concave part 57 and width S2 of the flat portion between the concave parts 57 are equal in a direction perpendicular to the polarizing surface. Furthermore, the width S1=S2 is greater than or equal to 60 nm.

Figure 41A:
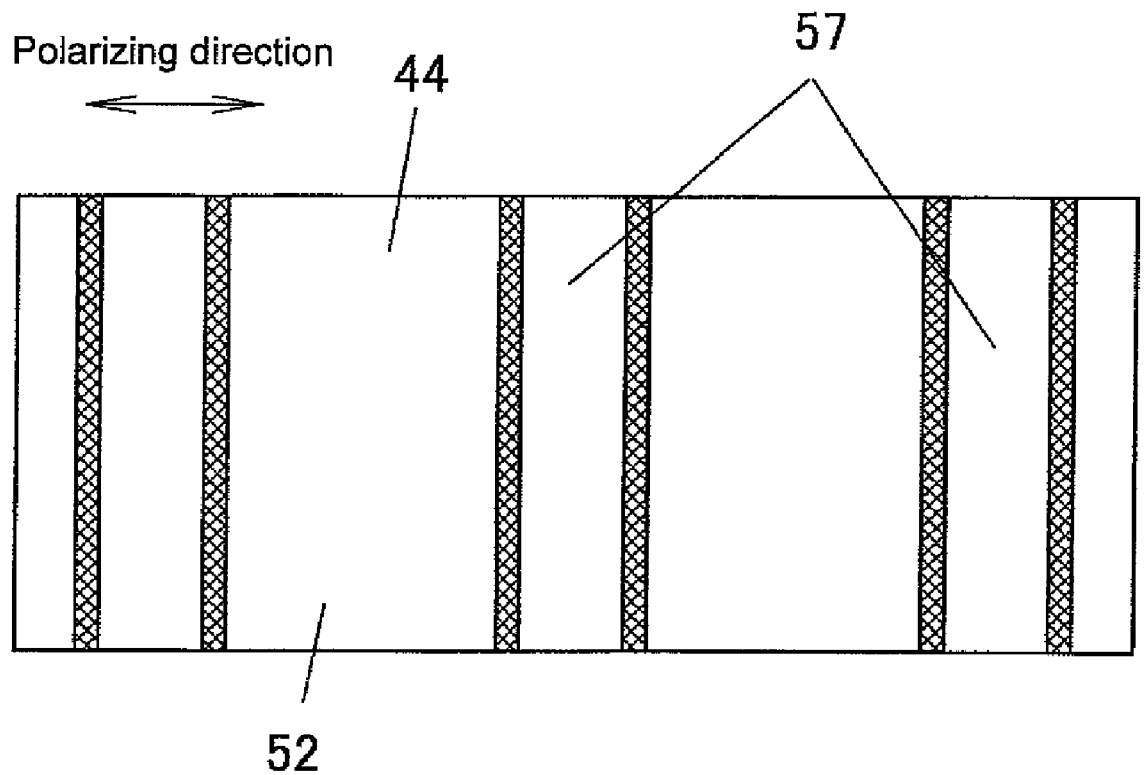
FIGS. 41A and 41B show a plan view and a cross sectional view of an immobilizing region such as immobilizing layer in the case of the first embodiment.
Figure 41B:
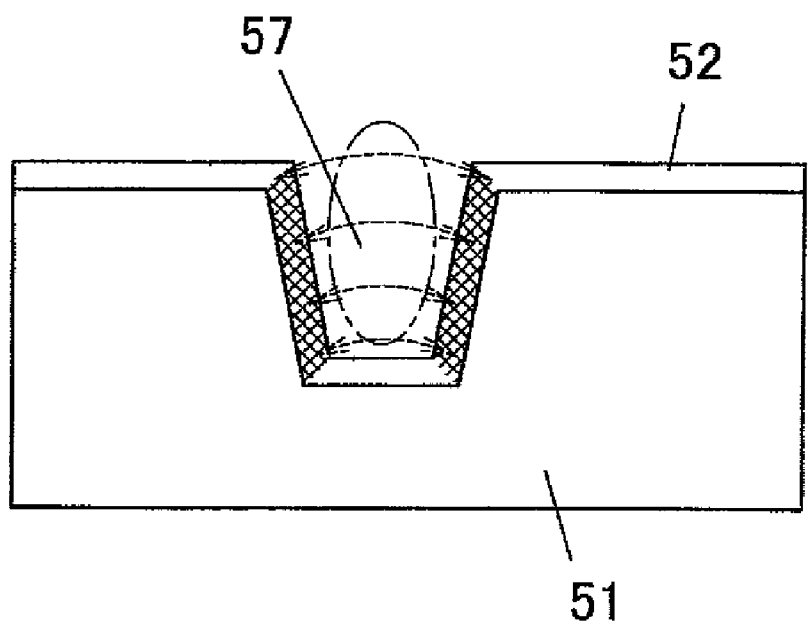

The features of the third embodiment will be described in comparison with the first embodiment. In the first embodiment, since the concave part 57 is extended to a concave groove form, when detecting the specific substance with organic molecular layer (e.g., immobilizing layer in the biosensor to be hereinafter described) for immobilizing the specific dielectric substance fixed, the organic molecular layer is fixed to the side wall face subjected to hatching of mesh form as in FIGS. 41A and 41B to contribute to the test of the specific substance. However, the organic molecular layer cannot be fixed to the region at the central part surrounded with an ellipse in FIG. 41B, and such region is extended along the longitudinal direction of the concave part 57.

Figure 42A:
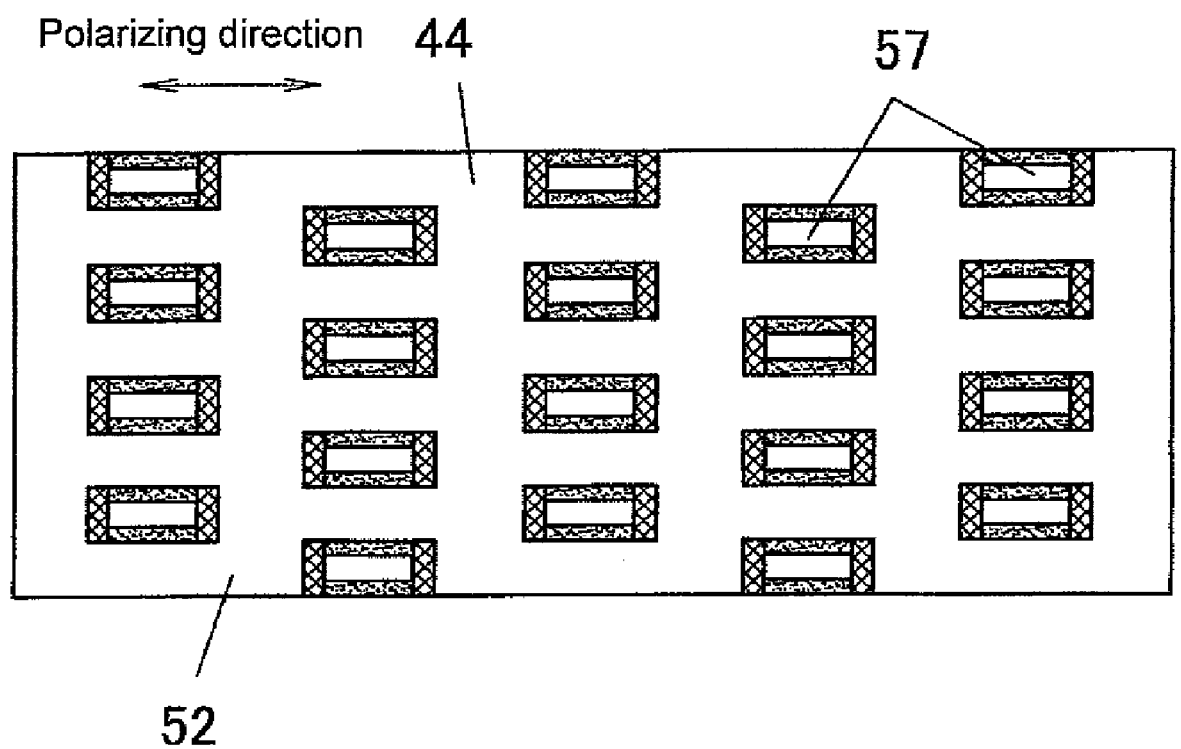
FIGS. 42A and 42B show a plan view and a cross sectional view of an immobilizing region such as immobilizing layer in the case of the third embodiment.
Figure 42B:
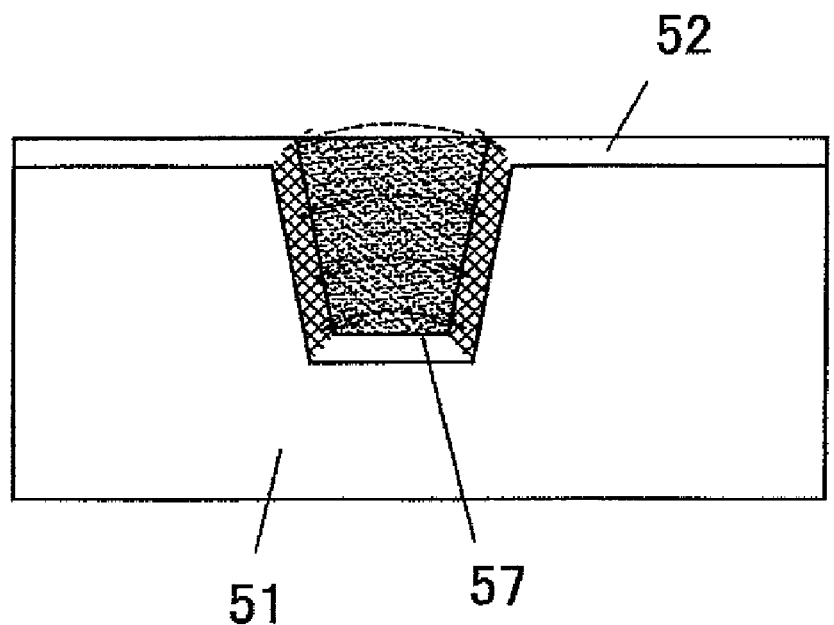

In the third embodiment, on the other hand, the concave part 57 of the first embodiment is divided into plurals, and thus the organic layer can be fixed only to the side wall face subjected to hatching of mesh form as in FIGS. 42A and 42B, but also the side wall face subjected to pear skin form, whereby the area of the side wall face contributing to the detection of the specific substance can be increased and the amount of change in resonance wavelength can be increased. Therefore, higher sensitivity of the local SPR sensor 31 is realized while maintaining the light usage efficiency.

Since the width S1 of the concave part 57 and the width S2 of the flat plane between the concave parts are equal in the direction perpendicular to the polarizing surface of the incident light, the concave parts 57 may be sufficiently spaced apart to prevent the generation of a mode caused by interaction of the adjacent concave parts 57.

Figure 43:
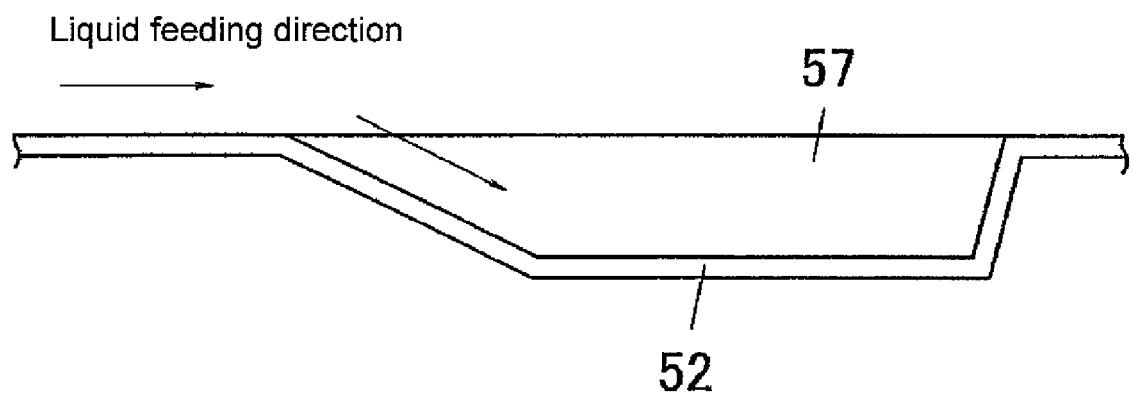
FIG. 43 shows a cross sectional view showing a concave part 57 in which an inclination angle of the side wall face on the side the test sample solution flows in is made small.

As shown in FIG. 43, the concave part 57 may be arranged parallel to the liquid feeding direction, and the inclination angle of the side (upstream side) the test sample solution flows in may be made smaller than the inclination angle of the side (downstream side) the solution flows out so that the flow-in of the test sample solution into the concave part 57 is promoted.

Fourth Embodiment

The local SPR sensor according to the present invention can be used as a biosensor for detecting protein. The protein was detected using the prototype having the configuration described in FIG. 20 to actually check the function as a biosensor. BSA (bovine serum albumin) was used as an antigen to be detected.

Figure 44:
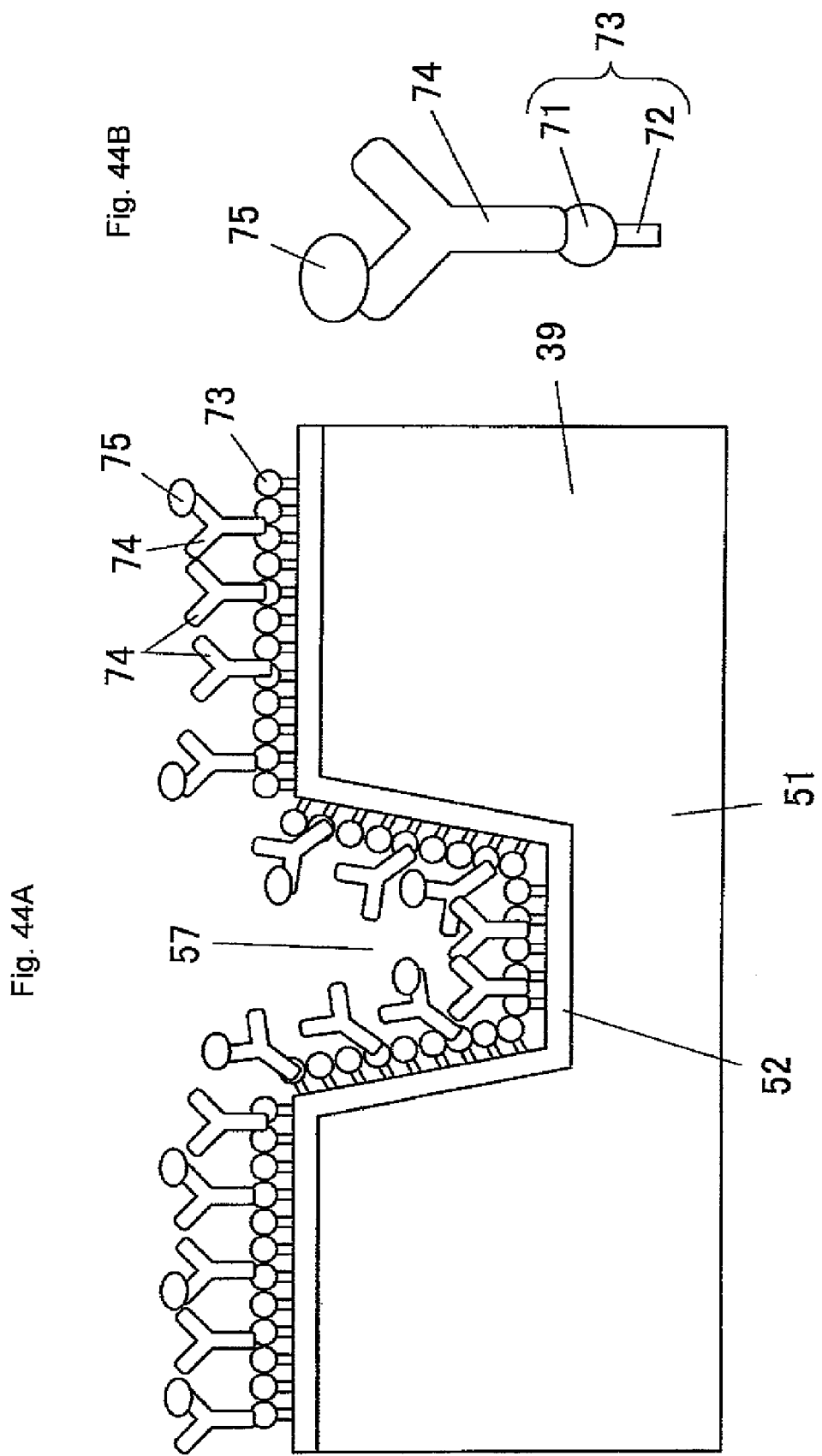
FIG. 44A shows a partial cross sectional view showing a sensor chip immobilized with an antibody and an antigen by way of the immobilizing layer.
FIG. 44B shows a view of an antibody immobilized to the immobilizing layer, and an antigen uniquely bound to an antibody.

First, the BSA antibody must be immobilized in the measurement region 44 to uniquely detect the BSA antigen. Since the sensitivity region is narrow or a few dozen nm in the local SPR sensor 31, as thin as possible immobilizing layer (organic layer for immobilizing the biological molecules) is required. The immobilizing layer sold from Orla Protein Technologies Co. (UK) was used. As shown in FIG. 44B, the immobilizing layer 73 is a protein in which a "protein A" 71 that binds with the antibody and a site "self-organized part 72) that forms the self-organized film at the Au surface are fused, and forms a surface for immobilizing the antibody with a thin film.

First the immobilizing layer 73 was formed on the measurement region 44, and liquid was fed at a speed of 20 μl/min to flow the BSA antibody (0.03 mg/ml) and the BSA antigen (0.1 mg/ml). As a result, as shown in FIG. 44A, the antibody 74 (BSA antibody) bound to the immobilizing layer 73 fixed at the surface of the metal layer 52, the antigen 75 (BSA antigen) uniquely bound to the antibody 74, and the index of refraction near the metal layer 52 changed, whereby change in resonance wavelength was measured using the local SPR sensor shown in FIG. 9.

Figure 45:
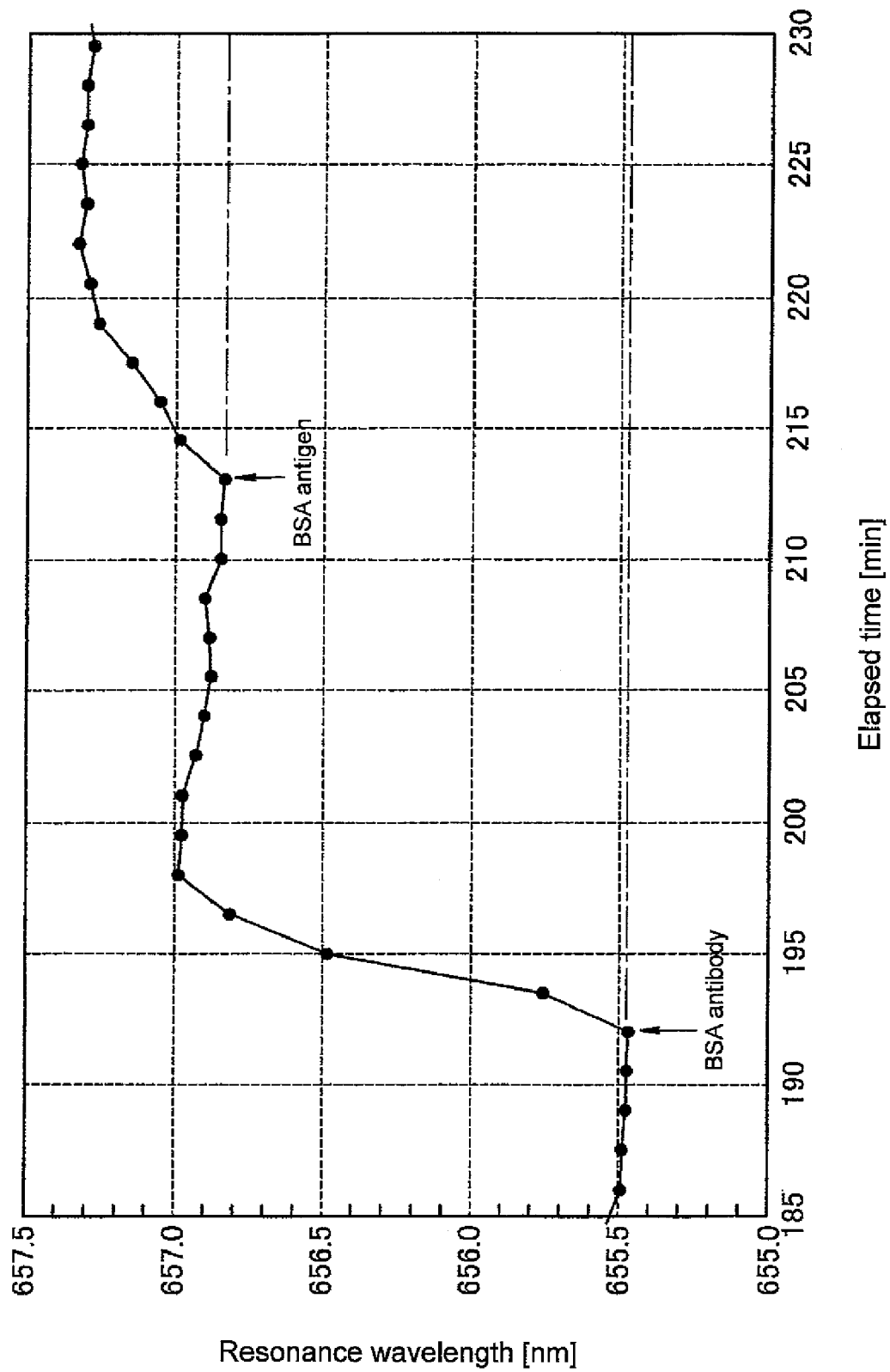
FIG. 45 shows a view of change in resonance wavelength when a test sample solution containing antibody and antigen is flowed to the sensor chip immobilized with the immobilizing layer.

The shifted amount of the resonance wavelength in this case is shown in FIG. 45. The horizontal axis of FIG. 45 is the elapsed time and the vertical axis is the resonance wavelength. As shown in FIG. 44A, it is assumed that first the BSA antibody binds to the immobilizing layer 73, and then the BSA antigen binds to the BSA antibody, and thus the resonance wavelength shift of about 1.4 nm at the beginning in FIG. 45 is due to the BSA antibody, and the resonance wavelength shift of about 0.5 nm thereafter is due to the BSA antigen. Thus, the protein can be detected by the local SPR sensor 31 of the present invention.

As shown in FIG. 46B, when protein in which a self-organized film forming site 76 and a single chain part of the antibody 74 are fused is used, the immobilizing layer can be further thinned and the surface formation process can be easily and conveniently performed as in FIG. 46A. A specific antibody can be detected by immobilizing an antigen at the measurement region.

Through the use of the local SPR sensor of the present invention application to food sensor for performing measurement of allergen, environment sensor, taste sensor, smell sensor, explosive sensor, and the like are also possible in addition to biosensor such as protein chip and DNA chip by changing the biological molecules to be immobilized.

Fifth Embodiment

A method of greatly raising the detection sensitivity of the biosensor includes a sandwich method as shown in FIG. 47. This methods raises the sensitivity to a few times by reacting an antibody 74 to an antigen 75 bound to an antibody 74 and causing great change in index of refraction.

Such method is known, but in the known method, the operation of flowing antibody solution again after flowing specimen such as blood is complicating, and is not realistic in a general household biosensor. Furthermore, in this method, the antibody of an excessive amount than the actual reaction amount needs to be flowed for a constant time, which arises problems of cost, measuring time, and the like.

Figure 48A:
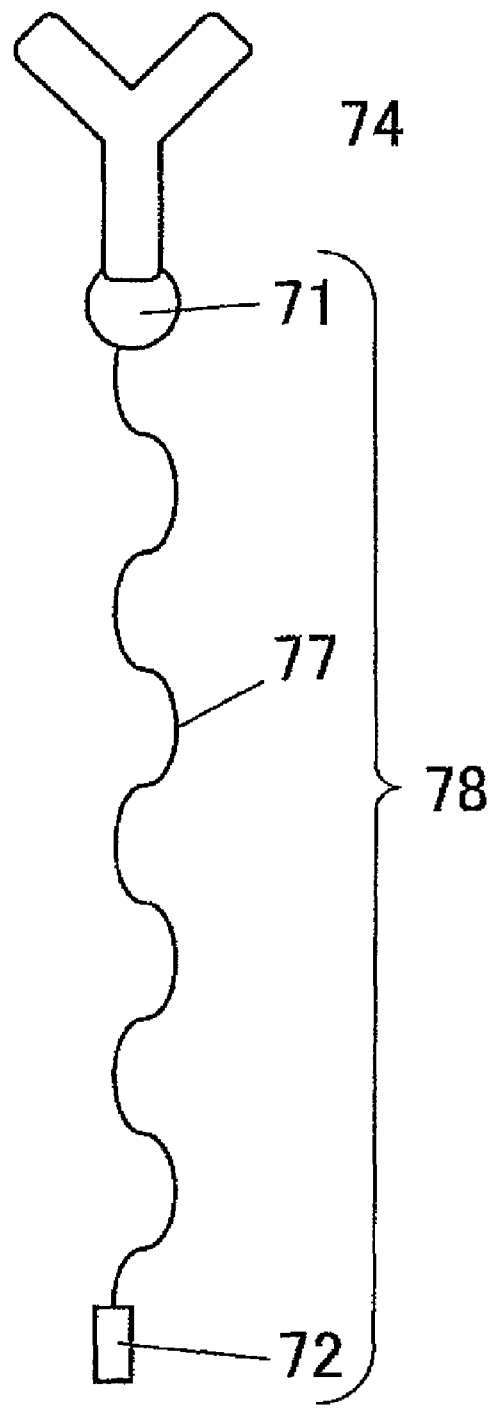
FIG. 48A shows a view of a substantially straightly extended linker part.

In the case of the sensor chip 39 of the present invention, on the other hand, the electric field is barely enhanced to greater than or equal to the electric field of the incident light at the region of greater than or equal to a few dozen nm of the surface of the metal layer 52 as the electric field distribution is as shown in FIG. 17. That is, the change in index of refraction of the protein existing in the relevant region barely contributes to signal change. Using such feature, an automatic sensitivity raise by the sandwich method can be performed in the sensor chip 39. That is, an antibody 74 for sensitivity enhancement can be "hidden" in a region that does not contribute to signal change, as shown in FIG. 49 by arranging an immobilizing layer 78 including a linker part 77 (having a length of greater than or equal to a few dozen nm) between the "protein A" 71 and the self-organized part 72 at a constant proportion in the immobilizing layer 73 as in FIG. 48A.

Figure 48B:
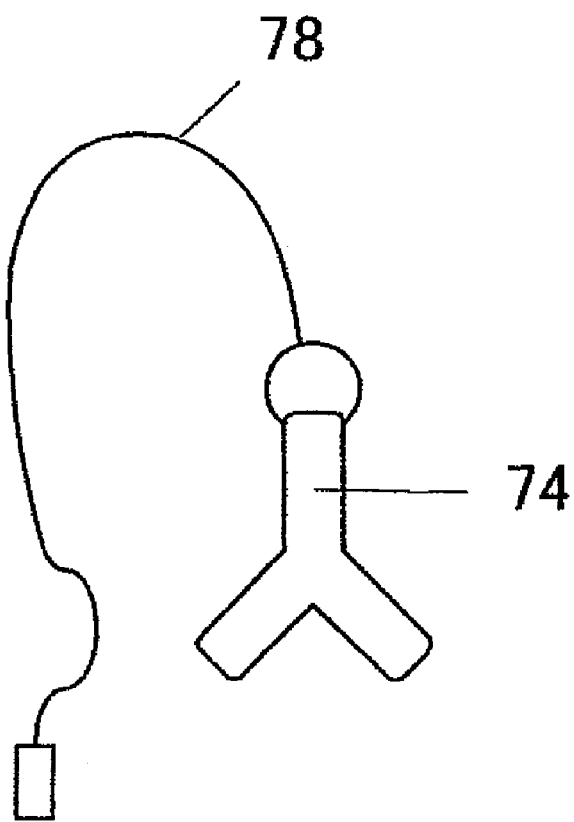
FIG. 48B shows a view of a curved linker part.

The raw material of the linker part 77 is suitably that which can be adjusted to a length of greater than or equal to a few dozen nm, and that can be curved in a free direction as shown in FIG. 48B, and that does not inhibit the movement of the antibody molecule in the solution. Specifically, a flexible peptide linker such as polyglycine and $(Gly-Gly-Gly-Ser)_n$ is used. These materials can appear in the coil bacteria as fused protein with the protein A and the protein (Orla protein etc.) configuring the self-organized part, and thus the manufacturing process and the cost can be reduced. Furthermore, sugar chain such as polyethylene glycol chain (PEG) and dextran having small non-unique attraction, DNA and the like can be chemically bonded with the functional group of the protein to be used as a linker.

Figure 49:
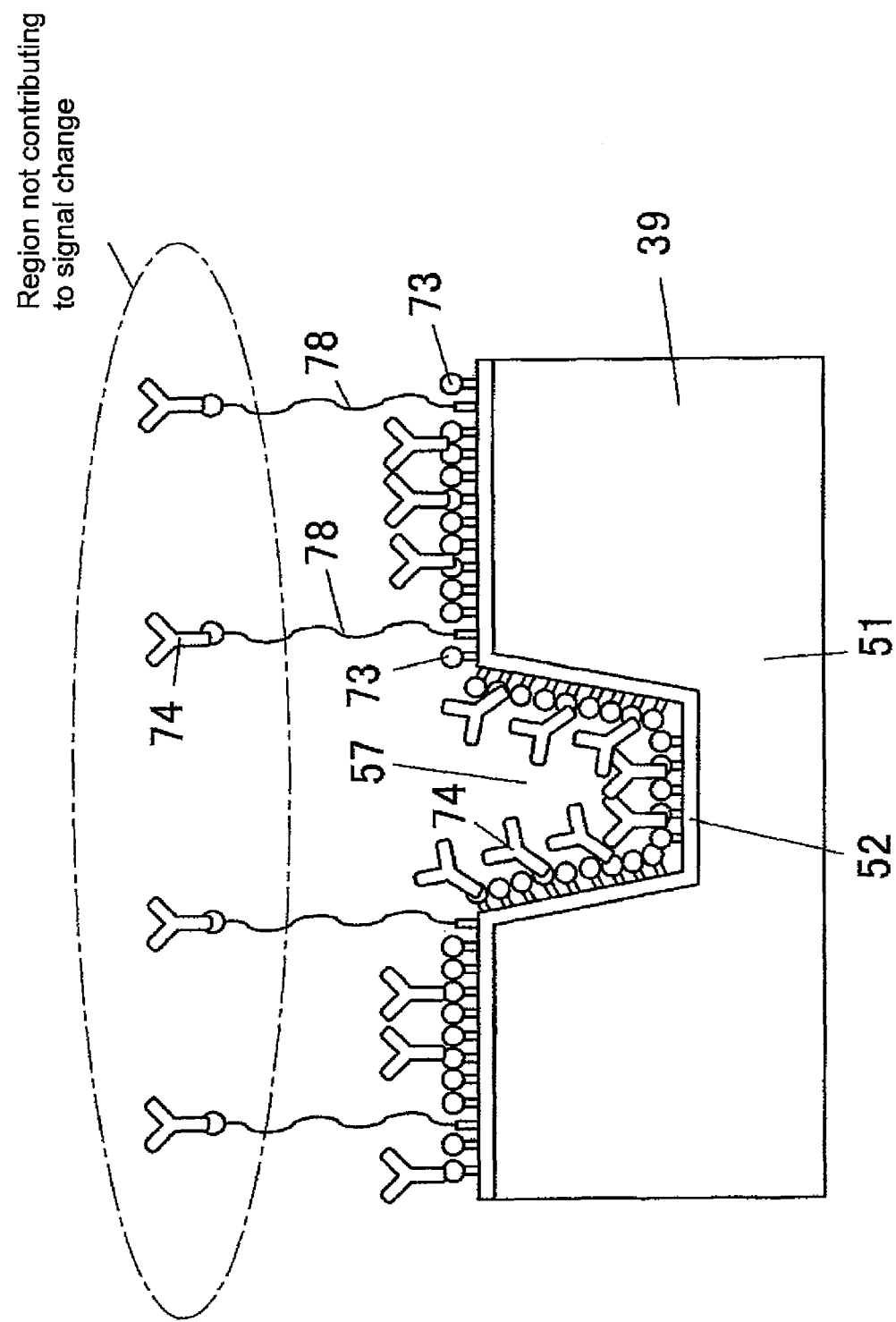
FIG. 49 shows a view of a state in which the linker part immobilized to the metal layer of the sensor chip is extended.
Figure 50:
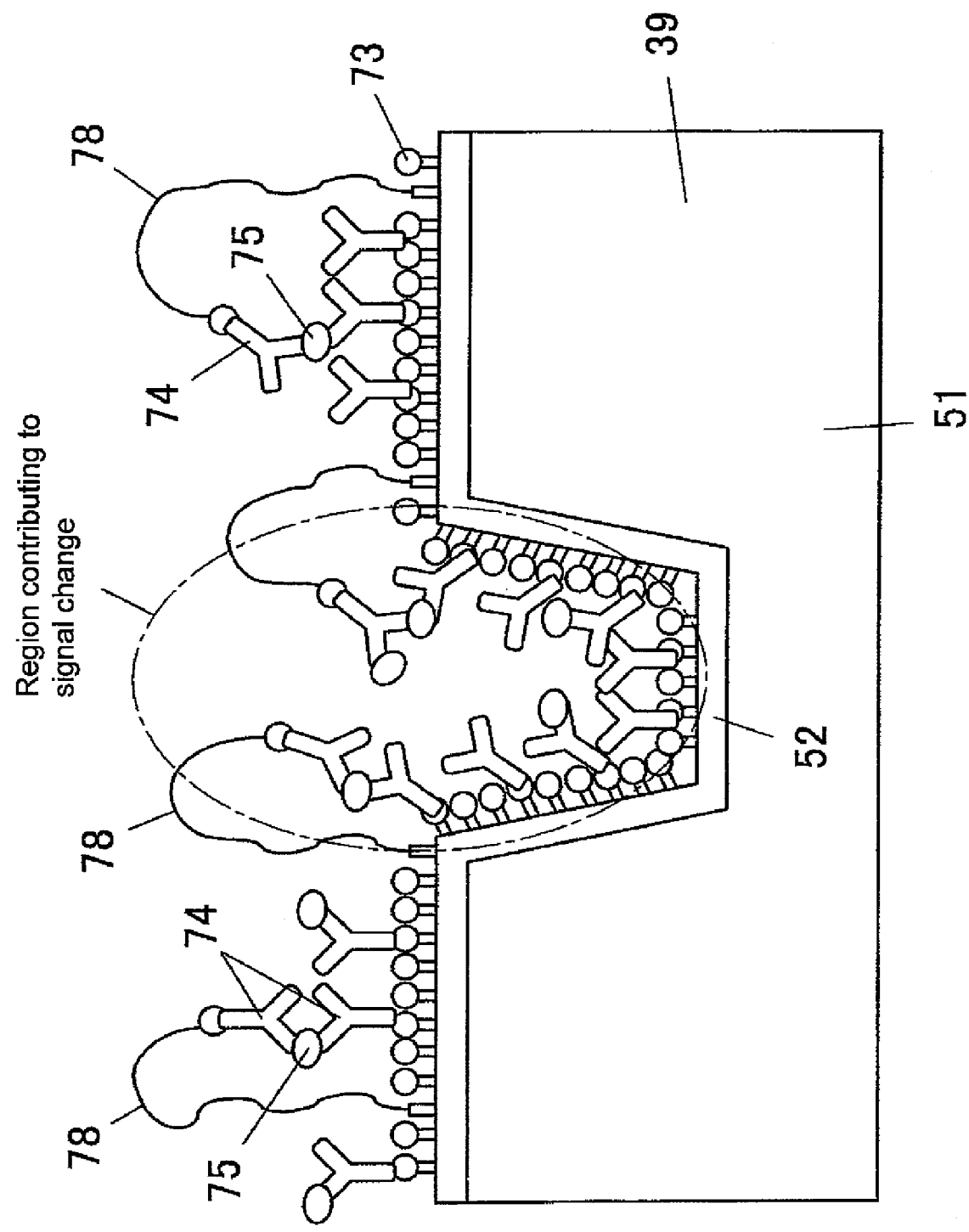
FIG. 50 shows a view of a state in which the linker part immobilized to the metal layer of the sensor chip is curved, and an antibody at the tip of the linker part is bound to an antigen uniquely bound to another antibody.

When using the biosensor, the immobilizing layer 73 to be directly immobilized with the antibody 74 and the immobilizing layer 78 for immobilizing the antibody 74 for sensitivity enhancement by way of the linker part 77 are fixed to the surface of the metal layer 52, as shown in FIG. 49. When the test sample solution containing the antigen 75 is flowed to the relevant surface, the antigen 75 binds to the antibody 74 of the immobilizing layer 73. The antigen 75 serves as an adhesive, and when the linker part 77 curves, the antibody 74 for sensitivity enhancement trapped at the tip of the linker part 77 binds with the antigen 75 thus automatically causing the sandwich reaction, as shown in FIG. 50. The antibody 74 for sensitivity enhancement thereby moves to the region where enhancement of the electric field is strongly occurring shown in FIG. 14, whereby high signal change occurs.

After the antigen liquid feeding, the liquid feeding speed and the liquid feeding direction are changed pulse-wise, so that the long linker part 77 curves and the antibody 74 for sensitivity enhancement trapped at the tip of the linker part 77 causes the sandwich reaction.

By using the linker part 77 in this manner, an automatic sandwich reaction, which was difficult in the conventional propagation surface plasmon resonance sensor, now becomes possible, and significant rise in sensitivity is realized.

Sixth Embodiment

In the actual clinical use and the like, there are needs for making the diagnosis at high throughput and enhancing the accuracy by performing the detection of a plurality of biological molecules once.

Figure 51:
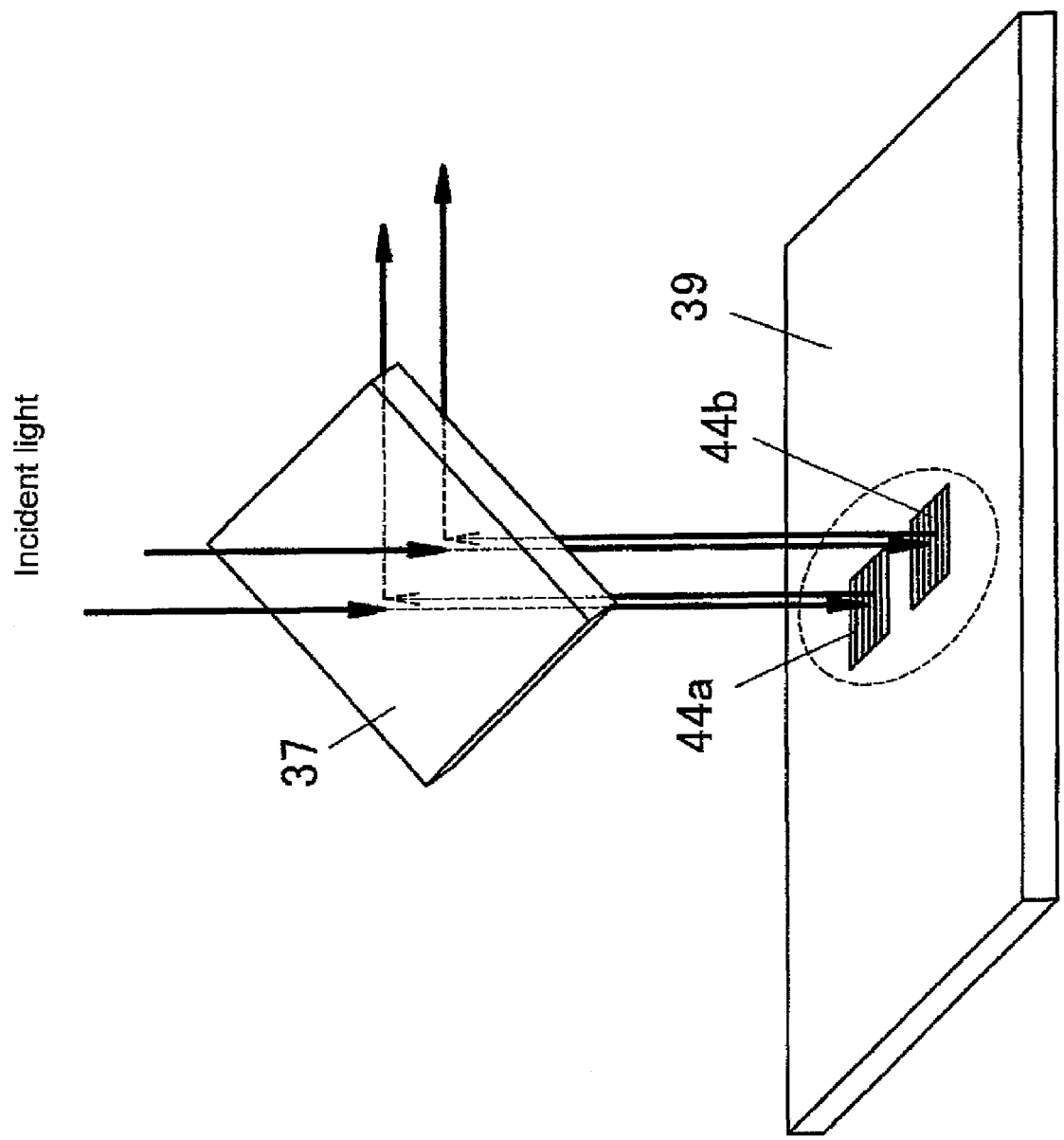
FIG. 51 shows a view describing a local SPR sensor according to a sixth embodiment of the present invention.

In order to respond to such needs, a plurality of measurement regions 44, that is, measurement regions 44a, 44b are formed in the sensor chip 39, as shown in FIG. 51, and the incident light is irradiated onto a region including the plurality of measurement regions 44a, 44b (e.g., region surrounded by an ellipse of broken line in FIG. 51).

Each measurement region 44a, 44b has the same configuration, and different probes (e.g., antibody) are immobilized to the respective measurement region 44a, 44b, so that a plurality of biological molecules can be detected all at once. A spotter etc. is used to immobilize different probes.

Alternatively, the width, the depth, the pitch, the direction of the groove, and the like of the concave part 57 at each measurement region 44a, 44b can differ.

Figure 52:
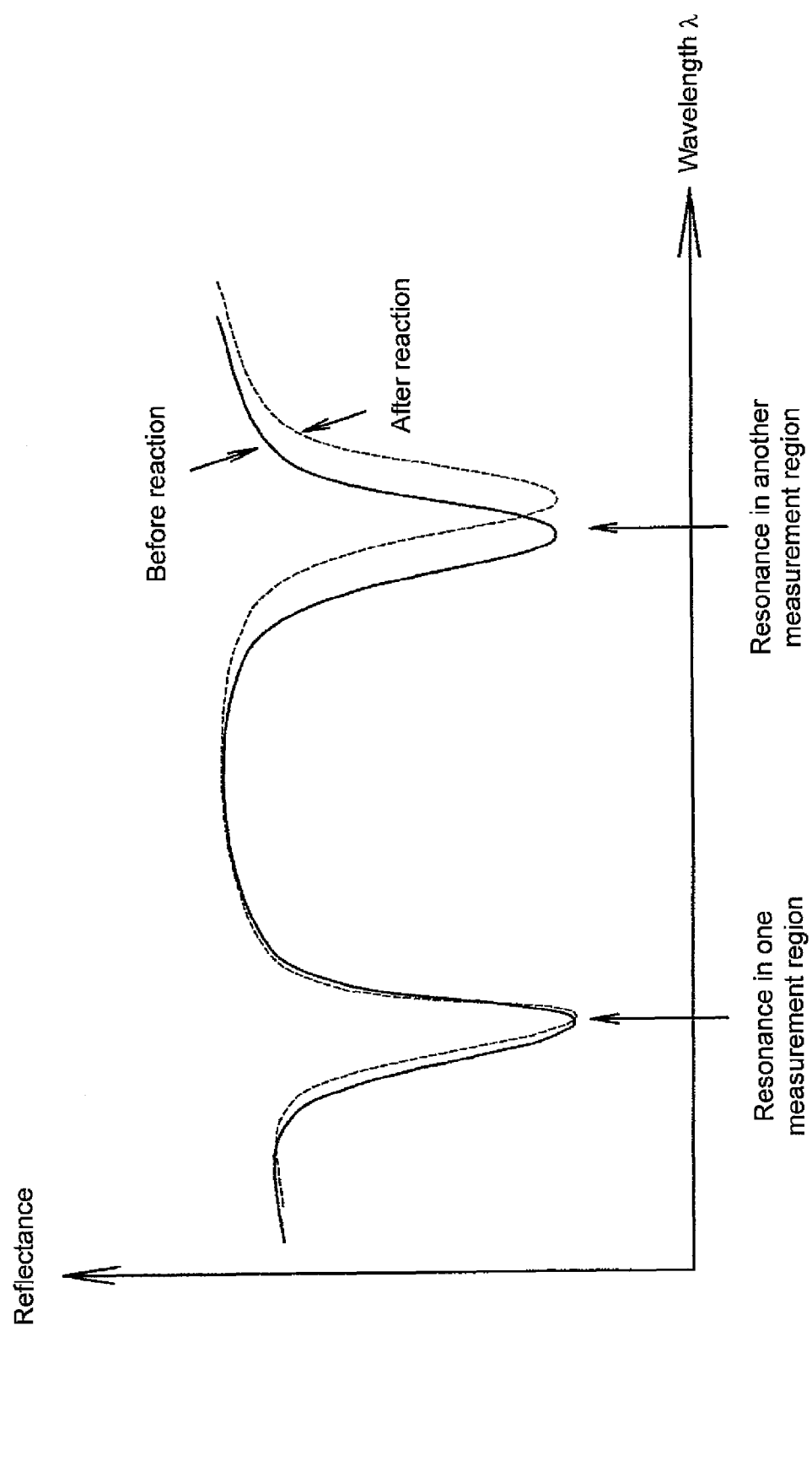
FIG. 52 shows a view describing a reflectance spectrum measured by the local SPR sensor of FIG. 51.

When incident light is irradiated onto the region including a plurality of measurement regions 44a, 44b, the resonance wavelength differs for each measurement region 44a, 44b if the probes differ for each measurement region 44a, 44b, or if the width, the depth, or the like of the concave part 57 differ, and thus the peak (resonance wavelength) of a plurality of reflectance can be observed as shown in FIG. 52.

The respective peak originates from the SPR in each measurement region 44a, 44b, and thus the reaction at each measurement region 44 can be measured all at once by detecting the shift of each peak.

The region of the plurality of measurement regions 44a, 44b can be detected in one irradiation without scanning the measurement region 44a, 44b one at a time with the incident light by differing the structure of the concave part 57 or the probe for each measurement region 44a, 44b. Therefore, mechanisms etc. for scanning the light become unnecessary, and the local SPR sensor is miniaturized and inexpensive.

In the conventional propagation surface plasmon resonance sensor, the generated SPR propagates the metal surface with a spread of a few μm to a few mm, and thus the adjacent measurement regions must be spaced apart by greater than or equal to a few hundred μm, whereby higher density of the sensor chip cannot be achieved. However, in the local surface plasmon resonance sensor of the present invention, since the generated SPR only locally exists, the interval with the adjacent measurement region probe can be approached to about a few μm, and a plurality of measurement regions can be arranged at high density.

Seventh Embodiment

Figure 53:
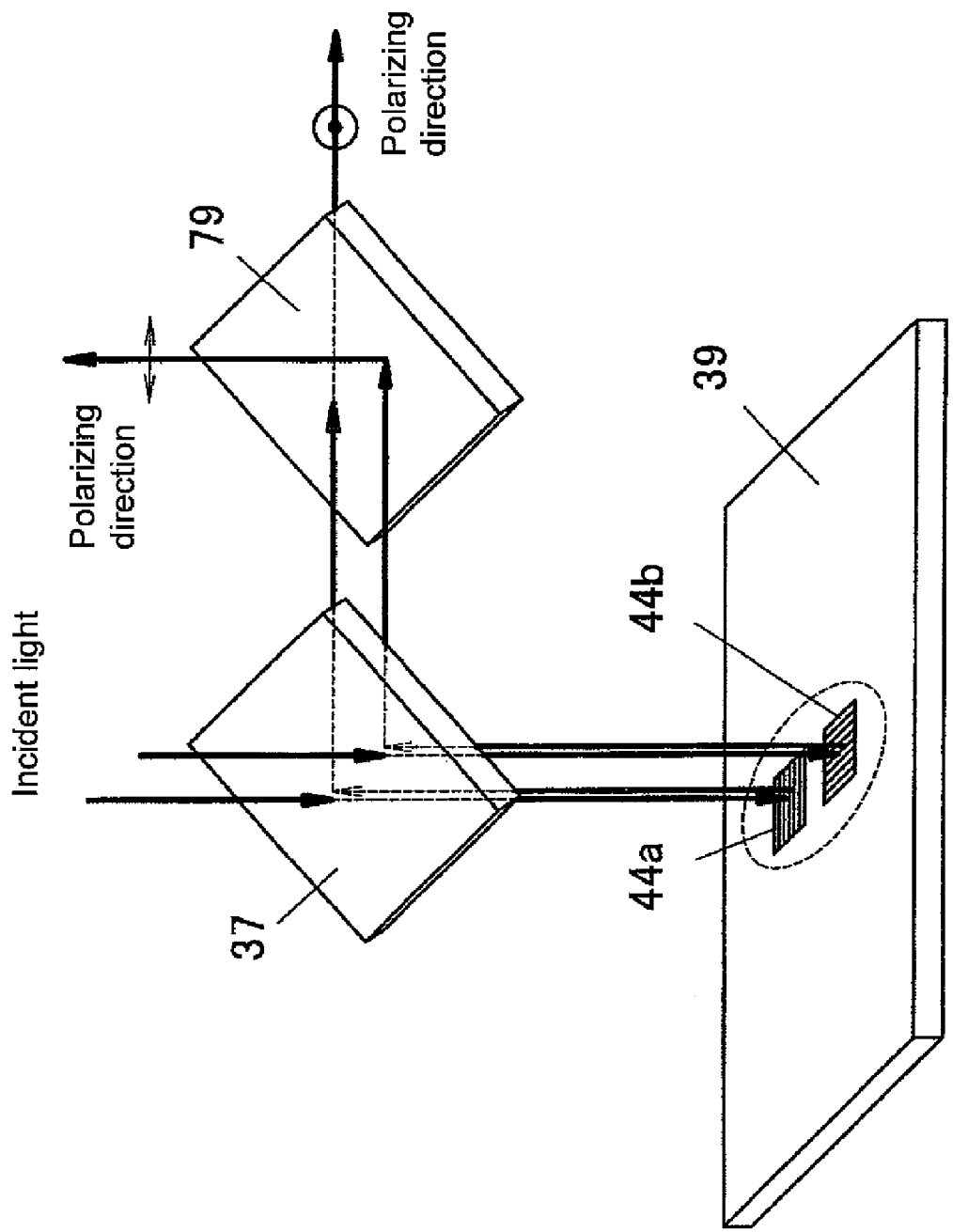
FIG. 53 shows a view describing a local SPR sensor according to a seventh embodiment of the present invention.

FIG. 53 shows a case where the directions of the longitudinal direction of the concave part 57 are differed by 90 degrees from each other at two measurement regions 44a, 44b arranged in the sensor chip 39. Regarding the light of linear polarization entering the measurement regions 44a, 44b, the light having a polarizing surface perpendicular to the length direction of the concave part 57 has a large sensitivity, and the light having a polarizing surface perpendicular to the length direction of the concave part 57 barely has sensitivity, and thus by irradiating light of no polarization to the measurement regions 44a, 44b and separating the light reflected by the measurement regions 44a, 44b to each polarizing direction by means of a polarization beam splitter 79 so as to be detected by the respective photodetector, the reaction at each measurement region 44a, 44b can be individually detected.

Eighth Embodiment

In the actual measurement, air bubbles sometimes mix into the sample solution. When air bubbles retain in the measurement region, large change in index of refraction occurs, and the measurement error occurs. Air bubbles tend to be trapped particularly at the boundary of the measurement region 44 through experiment.

In order to avoid errors caused by air bubbles, the measurement region can be enlarged to separate the boundary of the measurement region and the region contributing to the measurement, but with this method, the time for manufacturing the master for creating the sensor chip takes a long time pointlessly.

Figure 54:
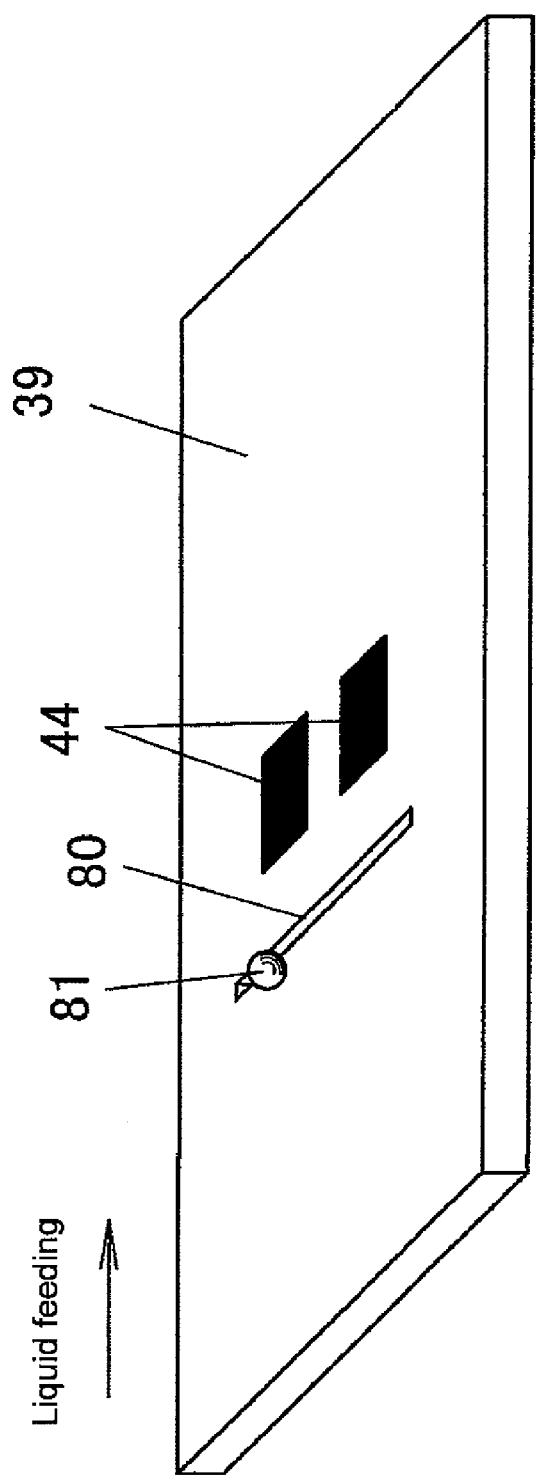
FIG. 54 shows a view describing a local SPR sensor according to an eighth embodiment of the present invention.

FIG. 54 shows a view where a trap 80 for trapping the air bubbles 81 is arranged on the upstream side of liquid feeding from the measurement region in order to resolve such problem. The trap 80 may be one or a plurality of concave grooves or projections that is long in a direction orthogonal to the liquid feeding direction, or may be a pattern same as the measurement region. If the size of the air bubbles is large or a few mm size, the trap 80 and the measurement region 44 are preferably spaced apart by greater than or equal to 1 mm.

Ninth Embodiment

Figure 55:
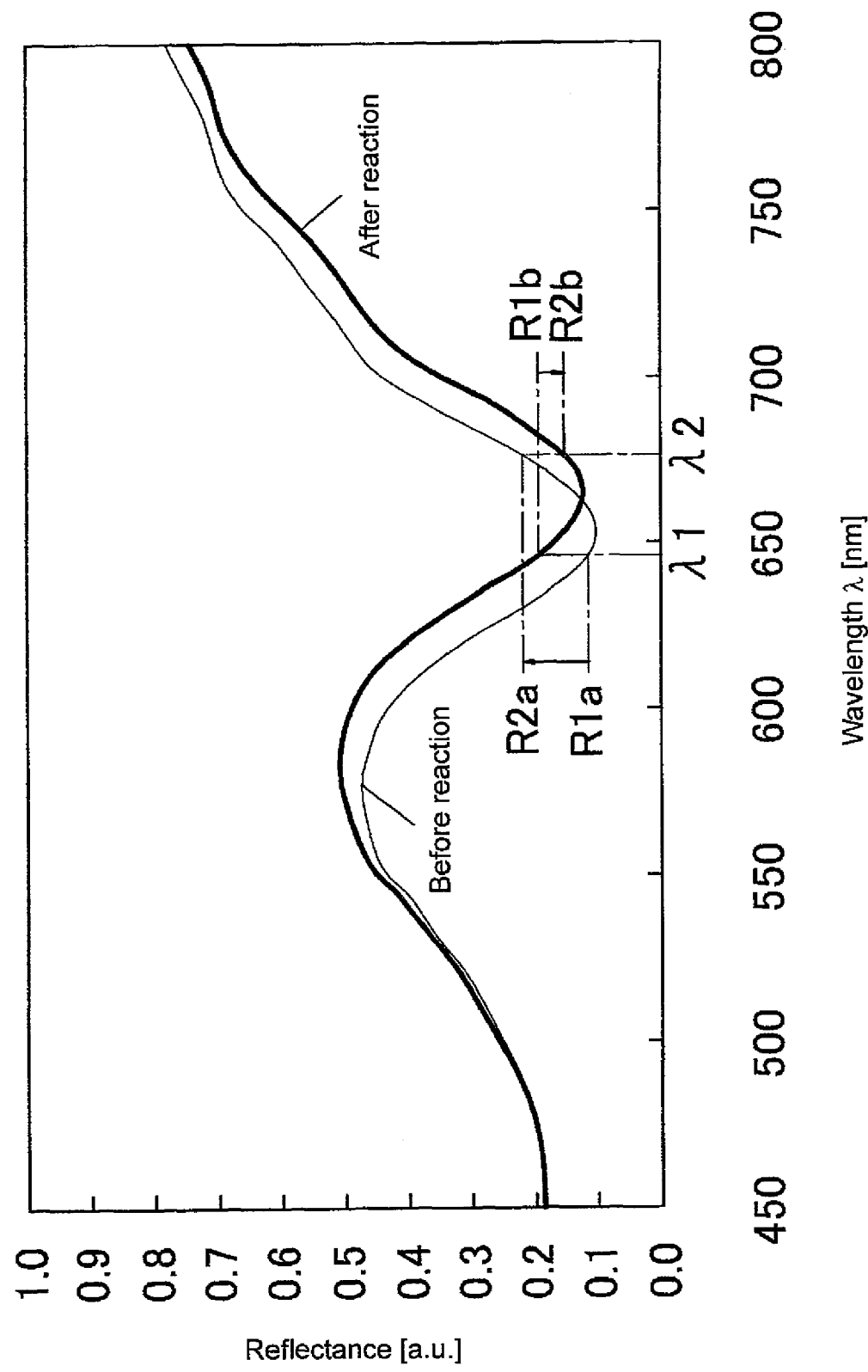
FIG. 55 shows a view describing a local SPR sensor according to a ninth embodiment of the present invention.

FIG. 55 shows a view explaining a local SPR sensor according to the embodiment of the present invention. In this embodiment, light having two specific wavelengths $\lambda 1$, $\lambda 2$ are irradiated instead of irradiating the white light to the measurement region 44. As shown in FIG. 55, the two wavelengths $\lambda 1$, $\lambda 2$ are selected so that the reflectance $R1a$ at wavelength $\lambda 1$ is smaller than the reflectance $R2a$ at the wavelength $\lambda 2$ ($R1a<R2a$) before reaction, and the reflectance $R1b$ at wavelength $\lambda 1$ is larger than the reflectance $R2b$ at the wavelength $\lambda 2$ ($R1b>R2b$) after reaction. The light receiving amount of the photodetector 41 may be compared.

According to the relevant embodiment, the test can be easily performed in the application of detecting the presence of a specific substance since the reflectance or the light receiving amount at two specific wavelengths merely needs to be compared.

In the surface plasmon resonance sensor of the present invention, when light enters the region including a concave part of nano size formed in the metal layer, bonding occurs between the free electrons at the opposing metal side faces in the concave part and the incident light, strong electric field concentrates at the inside of the concave part, and a strong local surface plasmon resonance generates. When surface plasmon resonance generates, the energy of the light is absorbed by the surface plasmon wave of the metal layer, and thus the reflectance of light or the light intensity received by the photodetector lowers at a certain wavelength (resonance wavelength). Such resonance wavelength changes by index of refraction of a medium in the concave part, and thus according to the relevant surface plasmon sensor, attachment of a dielectric substance in the concave part, change in attachment amount, and the like can be detected. In particular, use can be made as a biosensor to detect a specific protein.

Furthermore, in the surface plasmon resonance sensor of the present invention, strong surface plasmon resonance can be triggered since a large electric field enhancement is seen in the concave part, and sensing of very high sensitivity can be performed compared to the conventional propagation surface plasmon resonance sensor and local surface plasmon resonance sensor. Moreover, since the surface plasmon resonance sensor of the present invention has sensitivity in a narrow region of about a few dozen nm from the surface of the metal layer, the noise caused by substance of the region distant from the metal layer is small, and a surface plasmon resonance sensor having a satisfactory S/N ratio can be manufactured.

In the local surface plasmon resonance sensor up to now, the metal nano structures (metal fine particles) exist discontinuously (island shape), and thus is difficult to be efficiently manufactured. In the surface plasmon resonance sensor of the present invention, however, the metal layer is continuously formed, and thus the concave part can be formed by forming a metal film through processes such as vapor deposition and sputtering on a substrate formed with a depression through nanoimprinting technique etc. using a stamper. Therefore, since the sensor of the present invention excels in mass productivity, the sensor of high accuracy can be produced at low cost.

In another embodiment of the surface plasmon resonance sensor of the present invention, the concave part has a shape long in one direction when seen from a direction perpendicular to the main plane of the substrate, the light perpendicularly entered to the surface of the sensor chip is light of non-linear polarization, and the light received by the photodetector and reflected at the surface of the metal layer becomes linear polarization component entering the metal layer with the polarizing surface orthogonal to the longitudinal direction of the concave part. According to such embodiment, only the component that caused the largest surface plasmon resonance in the concave part is extracted and detected by the photodetector, and thus the sensitivity of the surface plasmon resonance sensor becomes very high.

In another further embodiment of the surface plasmon resonance sensor of the present invention, the concave parts are arrayed at a constant pitch at the surface of the metal layer, in particular, preferably formed to a periodic shape. In the relevant embodiment, the peak half value width in the reflectance spectrum can be narrowed, and the measurement accuracy can be enhanced.

In another further embodiment of the surface plasmon resonance sensor of the present invention, the depth of the concave part is greater than or equal to 20 nm and less than or equal to 100 nm, and the width of the concave part in a direction parallel to the polarizing surface of the light entering the surface of the metal layer is greater than or equal to 20 nm and less than or equal to 100 nm. If the depth of the concave part is deeper than 100 nm, the resonance absorption occurs at the wavelength of greater than or equal to 1000 nm, which may overlap the strong resonance absorption by water, and the peak half value width may also widen. If the depth of the concave part is shallower than 20 nm, the sensor sensitivity becomes small. Since the size of a general protein is about 10 nm, the width of the concave part must be at least about 20 nm in view of being used as a biosensor, and the effect of electric field enhancement in the concave part degrades if the width of the concave part becomes wider than greater than or equal to 100 nm.

In another further embodiment of the surface plasmon resonance sensor of the present invention, the interval (distance between the centers of the concave part) between the concave parts adjacent to each other is less than or equal to one half the wavelength of the light entering the surface of the metal layer. According to the relevant embodiment, the light entering the measurement region will not cause diffraction phenomenon by the concave part, and thus influence of diffraction can be eliminated. In particular, if the incident light is light of visible light region, the interval between the concave parts adjacent to each other is desirably less than or equal to 400 nm.

In another further embodiment of the surface plasmon resonance sensor of the present invention, the light having two or more wavelengths is perpendicularly entered to the sensor chip, and the reflectance of light of each wavelength or the light intensity of the light of each wavelength reflected by the sensor chip is measured by the photodetector. According to the relevant embodiment, the change in resonance wavelength can be evaluated by comparing the reflectance or the light intensity at the wavelength of two or more specific wavelengths. Application to testing the presence of a known specific substance, and the like is desirable.

The surface plasmon resonance sensor chip of the present invention is a surface plasmon resonance sensor chip including a substrate, and a metal layer formed so as to cover at least one part of the surface of the substrate, the light being received at the surface of the metal layer, where a plurality of concave parts is formed in the surface of the metal layer, an inner wall face of the concave part has at least a set of opposing metal layer surfaces, and a local resonance electric field is generated at the opposing metal layer surfaces.

In the surface plasmon resonance sensor chip of the present invention, when light perpendicularly enters the region including a concave part of nano size formed in the metal layer, bonding occurs between the free electrons at the opposing metal side faces in the concave part and the incident light, strong electric field concentrates at the inside of the concave part, and a strong local surface plasmon resonance generates. When surface plasmon resonance generates, the energy of the light is absorbed by the surface plasmon wave of the metal layer, and thus the reflectance of light or the light intensity received by the photodetector lowers at a certain wavelength (resonance wavelength). Such resonance wavelength changes by index of refraction of a medium in the concave part, and thus according to the relevant surface plasmon resonance sensor chip, attachment of a dielectric substance in the concave part, change in attachment amount, and the like can be detected. In particular, use can be made as a biosensor to detect a specific protein.

Furthermore, in the surface plasmon resonance sensor chip of the present invention, strong surface plasmon resonance can be triggered since a large electric field enhancement is seen in the concave part, and sensing of very high sensitivity can be performed compared to the conventional propagation surface plasmon resonance sensor and local surface plasmon resonance sensor. Moreover, since the surface plasmon resonance sensor chip of the present invention has sensitivity in a narrow region of about a few dozen nm from the surface of the metal layer, the noise caused by substance of the region distant from the metal layer is small, and a surface plasmon resonance sensor chip having a satisfactory S/N ratio can be manufactured.

In the local surface plasmon resonance sensor up to now, the metal nano structures (metal fine particles) exist discontinuously (island shape), and thus is difficult to be efficiently manufactured. In the surface plasmon resonance sensor chip of the present invention, however, the metal layer is continuously formed, and thus the concave part can be formed by forming a metal film through processes such as vapor deposition and sputtering on a substrate formed with a depression through nanoimprinting technique etc. using a stamper. Therefore, since the sensor chip of the present invention excels in mass productivity, the sensor chip of high accuracy can be produced at low cost.

In an embodiment of the surface plasmon resonance sensor chip of the present invention, the substrate includes a plurality of depressions at the surface, and the metal layer is formed on the surface of the substrate so as to form concave parts reflecting the shape of the depression formed at the surface of the substrate. According to the relevant embodiment, the concave part is formed along the depression by the metal layer by forming the metal layer on the surface of the substrate formed with depressions. Therefore, fine concave parts can be formed in the metal layer with a simple step.

The metal layer in another embodiment of the surface plasmon resonance sensor chip is formed by a metal thin film having a film thickness of greater than or equal to 40 nm and less than or equal to 100 nm in the depression of the substrate. If the film thickness of the metal layer is thinner than 40 nm, the light quantity of the reflected light becomes insufficient, and if the metal layer becomes too thick or has a film thickness of greater than or equal to 100 nm, the film forming time becomes long, and the manufacturing cost as well as the manufacturing throughput degrade.

In another further embodiment of the surface plasmon resonance sensor chip of the present invention, the inclination angle of the inner wall face of the concave part is greater than or equal to 75 degrees and less than or equal to 90 degrees with respect to the main plane of the substrate. The surface of the substrate refers to the surface of the substrate including the inside of the depression if depressions for forming the concave parts are formed in the substrate, and the main plane of the substrate refers to the surface of the substrate not including depressions if depressions for forming the concave parts are formed in the substrate. If the depressions for forming the concave parts are not formed in the substrate, the surface and the main plane of the substrate coincide. The sensor sensitivity is the best when the inclination angle of the side wall face of the concave part is 90 degrees, and as the inclination angle becomes smaller than 75 degrees, the sensor sensitivity becomes lower than or equal to half of at the time of 90 degrees, and thus has no practicability. If the inclination angle of the side wall face exceeds 90 degrees, it becomes difficult to form the depressions of the substrate using a stamper etc.

In another further embodiment of the surface plasmon resonance sensor chip of the present invention, the central part of the bottom surface of the concave part is raised towards the opening side of the concave part. According to the relevant embodiment, the substance attached to the bottom surface of the concave part can be lifted to a region of high electric field intensity, and thus the sensor sensitivity enhances.

In particular, the raised height of the bottom surface of the concave part is preferably greater than or equal to 5% and less than or equal to 20% with respect to the depth of the concave part. That is because the degree of enhancing the sensor sensitivity lowers if smaller than 5% or greater than 20%.

In another further embodiment of the surface plasmon resonance sensor chip of the present invention, the concave part has grooves parallel to each other. According to the relevant embodiment, the region for generating the surface plasmon resonance can be made long and wide, thereby enhancing the sensor sensitivity.

In another further embodiment of the surface plasmon resonance sensor chip of the present invention, the concave parts are arrayed along two directions, and the concave parts are arranged in a staggering manner. According to the relevant embodiment, the area for forming the organic molecular layer is made large in an application of forming an organic molecular layer etc. for immobilizing a specific molecule on the side wall face of the concave part, and the sensor sensitivity can be enhanced.

In such embodiment, the pitch in one array direction of the concave part is desirably larger than twice the width of the concave part in the relevant direction. According to such embodiment, the lights reflected at each concave part are less likely to interfere.

In another further embodiment of the surface plasmon resonance sensor chip of the present invention, a plurality of measurement regions formed with the concave part are arranged, and the depth, the width, or the array pitch of the concave part is differed for each measurement region. According to the relevant embodiment, a plurality of types of tests can be performed all at once since a plurality of measurement regions is arranged, and thus the test can be efficiently performed. Different resonance wavelengths can be provided to each measurement region, whereby the signal generated at each measurement region can be individually detected even if the light is irradiated to the entire plurality of measurement regions at once. Therefore, the light does not need to be sequentially scanned on each measurement region, and the configuration of the surface plasmon resonance sensor is simplified.

In another further embodiment of the surface plasmon resonance sensor chip of the present invention, an organic molecular layer for immobilizing the biological molecule is formed on the surface of the metal layer. According to the relevant embodiment, the biological molecules can be immobilized to the organic molecular layer, and thus a specific biological molecule can be detected, and use can be made as a biosensor.

In another further embodiment of the surface plasmon resonance sensor chip of the present invention, the organic molecular layer in the relevant embodiment is made of molecular which length from the surface of the substrate is greater than or equal to 50 nm and molecules which length from the surface of the substrate is shorter than 50 nm. If the organic molecular layer is formed by long molecules and short molecules, the short molecules bind with the biological molecules near the metal layer, the long molecules bind with the biological molecules distant from the metal layer, and the biological molecules are brought closer to the vicinity of the metal layer as the long molecules bound to the biological molecules bend, whereby great number of biological molecules can be collected in a region near the metal layer, and the sensor sensitivity can be further enhanced. A so-called linker part, for example, can be used as the long molecule. The linker part has a length of a few dozen nm, and is easily bent if the length is greater than or equal to 50 nm.

In another further embodiment of the surface plasmon resonance sensor chip of the present invention, Au or Ag is used as a material of the metal layer. Such metal layer material is chemically stable, and is able to generate a strong surface plasmon resonance.

A method of manufacturing a surface plasmon resonance sensor chip according to the present invention is a method of manufacturing a surface plasmon resonance sensor chip including steps of manufacturing a stamper with a convex pattern, transferring the convex pattern of the stamper to a resin by pressing the stamper to a non-cured resin, molding a substrate by curing the resin and forming a depression at the surface of the substrate by an inverted shape of the convex pattern, and depositing a metal on the surface of the substrate to form the metal layer, and forming a concave part with the metal layer formed reflecting the shape of the depressions.

According to the method of manufacturing the surface plasmon resonance sensor chip of the present invention, the depression is formed in the substrate using the stamper, and the metal layer is formed so as to reflect the shape of the depression thereby forming the concave part, and thus the surface plasmon resonance sensor chip including concave parts of the same shape can be stably manufactured without variation. Furthermore, the surface plasmon resonance sensor chip can be easily mass produced, and manufactured at low cost.

What is claimed is:

1. A surface plasmon resonance sensor comprising:
   a surface plasmon resonance sensor chip;
   a light source for irradiating light onto the surface plasmon resonance sensor chip; and
   a photodetector for receiving light reflected by the surface plasmon resonance sensor chip;
   wherein
   the surface plasmon resonance sensor chip comprises:
   a substrate,
   a metal layer formed so as to cover at least one part of a surface of the substrate, and
   a plurality of concave parts being formed in the metal layer,
   wherein the metal layer has a bottom surface in contact with the substrate and a top surface opposite to the bottom surface, and
   wherein the concave parts have at least one set of opposing side wall faces causing a local resonance electric field to be generated between the side wall faces when light is received at the top surface of the metal layer;
   the light is exited from the light source, entered to the surface of the sensor chip, reflected at a measurement region of the top surface of the metal layer including the concave parts, and received by the photodetector to measure a reflectance in the sensor chip or a light intensity received at the photodetector.

2. The surface plasmon resonance sensor according to claim 1, wherein the concave part has a shape that is long in one direction when seen from a direction perpendicular to a main surface of the substrate, the light perpendicularly entering the surface of the sensor chip is a light of linear polarization, and a polarizing surface of the light of linear polarization is orthogonal to a longitudinal direction of the concave part.

3. The surface plasmon resonance sensor according to claim 1, wherein the concave part has a shape that is long in one direction when seen from a direction perpendicular to a main surface of the substrate, the light perpendicularly entering the surface of the sensor chip is a light of nonlinear polarization, and the light received by the photodetector is a linear polarization component entering the metal layer at a polarizing surface orthogonal to a longitudinal direction of the concave part of the light reflected at the top surface of the metal layer.

4. The surface plasmon resonance sensor according to claim 1, wherein the concave part is arrayed at a constant pitch at the surface of the metal layer.

5. The surface plasmon resonance sensor according to claim 2, wherein a depth of the concave part is greater than or equal to 20 nm and less than or equal to 100 nm, and a width of the concave part in a direction parallel to the polarizing surface of the light entering the surface of the metal layer is greater than or equal to 20 nm and less than or equal to 100 nm.

6. The surface plasmon resonance sensor according to claim 1, wherein an interval between concave parts adjacent to each other is less than or equal to one half of a wavelength of the light entering the surface of the metal layer.

7. The surface plasmon resonance sensor according to claim 6, wherein an interval between concave parts adjacent to each other is less than or equal to 400 nm.

8. The surface plasmon resonance sensor according to claim 1, wherein the a light having two or more wavelengths is perpendicularly entered to the sensor chip, and a reflectance of the light of each wavelength or a light intensity of the light of each wavelength reflected at the sensor chip are measured with the photodetector.

9. A surface plasmon resonance sensor chip comprising:
a substrate; and
a metal layer formed so as to cover at least one part of a surface of the substrate;
wherein
the metal layer has a bottom surface in contact with the substrate and a top surface opposite the bottom surface;
a plurality of concave parts is formed in the metal layer;
the concave parts have at least one set of opposing side wall faces causing a local resonance electric field to be generated between the side wall faces when light is received at the top surface of the metal layer.

10. The surface plasmon resonance sensor chip according to claim 9, wherein the substrate includes a plurality of depressions on the surface; and the metal layer is formed on the surface of the substrate so as to form the concave part reflecting a shape of the depression formed at the surface of the substrate.

11. The surface plasmon resonance sensor chip according to claim 10, wherein the metal layer is formed by a metal thin-film having a thickness of greater than or equal to 40 nm and less than or equal to 100 nm in the depression of the substrate.

12. The surface plasmon resonance sensor chip according to claim 9, wherein an inclination angle of the inner wall face of the concave part is greater than or equal to 75 degrees and smaller than or equal to 90 degrees with respect to a main plane of the substrate.

13. The surface plasmon resonance sensor chip according to claim 9, wherein a central part of a bottom surface of the concave part is raised towards an opening side of the concave part.

14. The surface plasmon resonance sensor chip according to claim 13, wherein a height of the raise is greater than or equal to 5% and smaller than or equal to 20% with respect to a depth of the concave part.

15. The surface plasmon resonance sensor chip according to claim 9, wherein the concave parts form grooves parallel to each other.

16. The surface plasmon resonance sensor chip according to claim 9, wherein the concave parts are arrayed along two directions, and the concave parts are arranged in a staggering manner.

17. The surface plasmon resonance sensor chip according to claim 16, wherein the concave part has a pitch in one arraying direction greater than twice a width of the concave part in the arraying direction.

18. The surface plasmon resonance sensor chip according to claim 9, wherein a plurality of measurement regions formed with the concave parts are arranged, and a depth, a width, or an array pitch of the concave part differs for every measurement region.

19. The surface plasmon resonance sensor chip according to claim 9, wherein an organic molecular layer for immobilizing a biological molecule is formed on the surface of the metal layer.

20. The surface plasmon resonance sensor chip according to claim 19, wherein the organic molecular layer includes a molecule having a length from the surface of the substrate of greater than or equal to 50 nm and a molecule having a length from the surface of the substrate of shorter than 50 nm.

21. The surface plasmon resonance sensor chip according to claim 9, wherein a material of the metal layer is Au or Ag.

22. A method of manufacturing the surface plasmon resonance sensor chip according to claim 9, the method comprising the steps of:
manufacturing a stamper having a convex pattern;
transferring the convex pattern of the stamper onto a resin by pressing the stamper to a non-cured resin, and curing the resin to mold a substrate and form a depression at a surface of the substrate by an inverted shape of the convex pattern; and
depositing metal on the surface of the substrate to form a metal layer and concave parts reflecting the shape of the depression.

23. The surface plasmon resonance sensor according to claim 3, further comprising a polarization plate, wherein the light reflected from the top surface of the metal layer is transmitted through the polarization plate before being received by the photodetector, and wherein the polarization plate is arranged such that the polarizing surface of the transmitted light is orthogonal to the longitudinal direction of the concave part.

24. The surface plasmon resonance sensor according to claim 9, wherein the surface plasmon resonance sensor chip includes two measurement regions formed with the concave parts, wherein a longitudinal direction of the concave parts is orthogonal to each other in the measurement regions, the sensor further comprising a polarizing beam splitter, wherein the light reflected from the top surface of the metal layer is transmitted through the polarizing beam splitter before being received by respective photodetectors, and wherein the polarizing beam splitter is arranged such that the polarizing surface of the transmitted light is orthogonal to the longitudinal direction of the concave parts for the two measurement regions.

25. The surface plasmon resonance sensor according to claim 9, further comprising:
an immobilizing layer on the top surface of the measurement region;
an antibody is bound to the immobilizing layer; and
an antigen is bound to the antibody;
wherein the surface plasmon resonance sensor is adapted to detect the antigen.

26. The surface plasmon resonance sensor according to claim 25, wherein the immobilizing layer further comprises a linker part, wherein the antibody is bound to the linker part or to the immobilizing layer, and wherein the antigen is bound to the antibody bound to the immobilizing layer and to the antibody bound to the linker part.

* * * * *